United States Patent
Remaley et al.

(10) Patent No.: US 11,872,261 B2
(45) Date of Patent: Jan. 16, 2024

(54) LIPOPROTEIN TARGETING PROTEASE INHIBITORS AND USES

(71) Applicant: The United States of America, as represented by the Secretary, Dept. of Health and Human Services, Bethesda, MD (US)

(72) Inventors: Alan T. Remaley, Bethesda, MD (US); Scott M. Gordon, Lexington, KY (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/673,361

(22) Filed: Feb. 16, 2022

(65) Prior Publication Data
US 2022/0168379 A1 Jun. 2, 2022

Related U.S. Application Data

(60) Continuation of application No. 16/692,849, filed on Nov. 22, 2019, now abandoned, which is a division of application No. 15/297,054, filed on Oct. 18, 2016, now abandoned.

(60) Provisional application No. 62/332,277, filed on May 5, 2016.

(51) Int. Cl.
| | | |
|---|---|---|
| A61K 38/00 | (2006.01) | |
| A61K 38/07 | (2006.01) | |
| A61K 38/10 | (2006.01) | |
| A61K 38/58 | (2006.01) | |
| A61K 38/17 | (2006.01) | |
| A61K 47/54 | (2017.01) | |
| A61K 47/60 | (2017.01) | |
| A61K 38/08 | (2019.01) | |

(52) U.S. Cl.
CPC ............ *A61K 38/005* (2013.01); *A61K 38/07* (2013.01); *A61K 38/08* (2013.01); *A61K 38/10* (2013.01); *A61K 38/1767* (2013.01); *A61K 38/58* (2013.01); *A61K 47/545* (2017.08); *A61K 47/60* (2017.08)

(58) Field of Classification Search
CPC ...... A61K 38/005; A61K 38/07; A61K 38/08; A61K 38/10; A61K 38/1767; A61K 38/58; A61K 47/545; A61K 47/60
See application file for complete search history.

(56) References Cited

U.S. PATENT DOCUMENTS

| | | |
|---|---|---|
| 4,665,053 A | 5/1987 | Robert et al. |
| 8,658,604 B2 | 2/2014 | Demarco et al. |
| 2009/0156507 A1 | 6/2009 | Livnah et al. |
| 2011/0300199 A1 | 12/2011 | Sanz et al. |
| 2012/0177626 A1 | 7/2012 | Meilhac |

FOREIGN PATENT DOCUMENTS

| | | |
|---|---|---|
| WO | WO 01/00247 A1 | 1/2001 |
| WO | WO 2010/091893 A1 | 8/2010 |
| WO | WO 2011/006994 A1 | 1/2011 |
| WO | WO 2013/187673 | 12/2013 |

OTHER PUBLICATIONS

Armstead et al. "PAI-1-derived peptide EEIIMD prevents impairment of cerebrovasodilation by augmenting p38 MAPK upregulation after cerebral hypoxia/ischemia." *American Journal of Physiology—Heart and Circulatory Physiology* 299(1): H76-H80, 2010.

Barros et al. "Influence of secretory leukocyte protease inhibitor-based peptides on elastase activity and their incorporation in hyaluronic acid hydrogels for chronic wound therapy." *Peptide Science* 98(6): 576-590, 2012.

Carr et al., "Interrelationships of a-tocopherol with plasma lipoproteins in African green monkeys: effects of dietary fats," *Journal of Lipid Research*, 34: 1863-1871, 1993.

Ding et al. "A new Kunitz-type plasmin inhibitor from scorpion venom." *Toxicon* 106: 7-13, 2015.

Dodt et al. "The complete amino acid sequence of hirudin, a thrombin specific inhibitor." *FEBS letters* 165(2): 180-184, 1984.

Gibbons et al., "Delivery of rSLPI in a liposomal carrier for inhalation provides protection against cathepsin L degradation," *Journal of Microencapsulation*, 26(6): 513-522, 2009.

Gordon et al. "Proteomic characterization of human plasma high density lipoprotein fractionated by gel filtration chromatography." *J Proteome Res* 9(10): 5239-5249, 2010.

Gordon et al. "Rosuvastatin Alters the Proteome of High Density Lipoproteins: Generation of alpha-1-antitrypsin Enriched Particles with Anti-inflammatory Properties." *Molecular & Cellular Proteomics* 14(12): 3247-3257, Oct. 19, 2015.

(Continued)

*Primary Examiner* — Julie Ha
*Assistant Examiner* — Erinne R Dabkowski
(74) *Attorney, Agent, or Firm* — Klarquist Sparkman, LLP

(57) ABSTRACT

Described herein is the design and construction of a class of lipoprotein targeting protease inhibitors. Small peptides with protease inhibitor activity are conjugated to hydrophobic, lipoprotein targeting molecules using, for instance, amine reactive chemistry. Methods of use of the resultant lipoprotein targeting protease inhibitor (antiprotease) molecules are also described. Also described is the production and use of protease inhibitor enriched HDL particles, as well as A1AT-peptide-enriched HDL particles, and their use in various therapeutic contexts.

8 Claims, 15 Drawing Sheets
Specification includes a Sequence Listing.

(56) References Cited

OTHER PUBLICATIONS

Greinacher et al. "The direct thrombin inhibitor hirudin." *Thrombosis and Haemostasis-Stuttgart*—99(5):819, 2008.
Guo et al., "The applications of Vitamin E TPGS in drug delivery," *European Journal of Pharmaceutical Sciences*, doi: http//dx.doi.org/10.1016/j.ejps.2013.02.006, 2013 (36 pages).
Hazen et al. "HDL structure, function, therapeutics, and imaging." *Arteriosclerosis, thrombosis, and vascular biology* 30(2): 138-138, 2010.
Hazen et al. "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV." *Antimicrobial agents and chemotherapy* 51(9): 3147-3154, 2007.
Henriksen et al., "Adenoviral Gene Delivery of Elafin and Secretory Leukocyte Protease Inhibitor Attenuates NF-KB-Dependent Inflammatory Responses of Human Endothelial Cells and Macrophages to Atherogenic Stimuli," *The Journal of Immunology*, 172: 4535-4544, 2004.
Ingallinella et al. "Addition of a cholesterol group to an HIV-1 peptide fusion inhibitor dramatically increases its antiviral potency." *Proceedings of the National Academy of Sciences* 106(14): 5801-5806, 2009.
Kotani et al., "The association between adiponectin, HDL-cholesterol and a 1-antitrypsin-LDL in female subjects without metabolic syndrome," *Lipids in Health and Disease*, 9:147, 2010 (5 pages).
Lee et al. "Direct thrombin inhibitors." *British journal of clinical pharmacology* 72(4): 581-592, 2011.
Meilhac. "High-density lipoproteins in stroke." *Handbook of Experimental Pharmacology* 224:509-526, 2015.
Moreno et al. "High-density lipoproteins potentiate α1-antitrypsin therapy in elastase-induced pulmonary emphysema." *American journal of respiratory cell and molecular biology* 51(4): 536-549, 2014.
Mutharasan et al. "High-density lipoproteins for therapeutic delivery systems." *Journal of Materials Chemistry B* 4(2): 188-197, 2016.
Namjoshi et al., "Enhanced Transdermal Peptide Delivery and Stability by lipid Conjugation: Epidermal Permeation, Stereoselectivity and Mechanistic Insights," *Pharm Res*, vol. 31, pp. 3304-3312, 2014.
Ndinguri et al. "Peptide-based selective inhibitors of matrix metalloproteinase-mediated activities." *Molecules* 17(12): 14230-14248, 2012.
Oritz-Muñoz et al. "HDL antielastase activity prevents smooth muscle cell anoikis, a potential new antiatherogenic property." *The FASEB Journal* 23(9): 3129-3139, 2009.
Schaschke et al. "Epoxysuccinyl peptide-derived cathepsin B inhibitors: modulating membrane permeability by conjugation with the C-terminal heptapeptide segment of penetratin." *Biological chemistry* 383(5): 849-852, 2002.
Sigma-Aldrich (Product No. 0398, published online 2002), 1 page. Sigma-Aldrich Product Information, Product No. M 0398, "MeOSuc-Ala-Ala-Pro-Val Chloromethyl Ketone," (at sigmaaldrich.com/content/dam/sigma-aldrich/docs/Sigma/Datasheet/4/m0398dat.pdf; one page), downloaded Apr. 19, 2016.
Simon et al. "Targeting Proteases in Atherosclerosis Hitting the Nail With the Hammer." *Circulation* 124(3): 2480-2482, 2011.
Stone et al., "The Moderation of Elastase-Induced Emphysema in the Hamster by Intratracheal Pretreatment or Post-Treatment With Succinyl Alanyl Alanyl Prolyl Valine Chloromethyl Ketone," *Respir. Dis.*, 124(1): 56-59, 1981.
Taggart et al. "Oxidation of either methionine 351 or methionine 358 in α1-antitrypsin causes loss of anti-neutrophil elastase activity." *Journal of Biological Chemistry* 275(35): 27258-27265, 2000.
Tan et al. "Plasminogen activator inhibitor type 1 derived peptide, EEIIMD, diminishes cortical infarct but fails to improve neurological function in aged rats following middle cerebral artery occlusion." *Brain research* 1281: 84-90, 2009.
Tran-Dinh et al. "HDL and endothelial protection." *British journal of pharmacology* 169(3): 493-511, 2013.
Tsai et al. "Neutrophil elastase inhibitors: a patent review and potential applications for inflammatory lung diseases (2010-2014)." *Expert opinion on therapeutic patents* 25(10): 1145-1158, 2015.
Tuhy et al. "Inhibition of human leukocyte elastase by peptide chloromethyl ketones." *FEBS letters* 50(3): 359-361, 1975.
Valsar et al., "Shotgun proteomic implicates protease inhibition and complement activation in the antiinflammatory properties of HDL," *The Journal of Clinical Investigation*, vol. 117, No. 3, pp. 746-756, 2007.
Zhu et al. "Z-Phe-Gly-NHO-Bz, an inhibitor of cysteine cathepsins, induces apoptosis in human cancer cells." *Clinical Cancer Research* 6(5): 2064-2069, 2000.

| Protein | Membrane Insertion Depth (Å) | $\Delta G_{transfer}$ (kcal/mol) | Embedded residues |
|---|---|---|---|
| A1AT | 3.3 ± 1.4 | -5.8 | 351,353,355,358 |
| A1AT Δ 346 | 1.1 ± 1.9 | -2.7 | 213 |

⬅ = Protein degradation fragments

FIG. 13A
FIG. 13B
FIG. 14
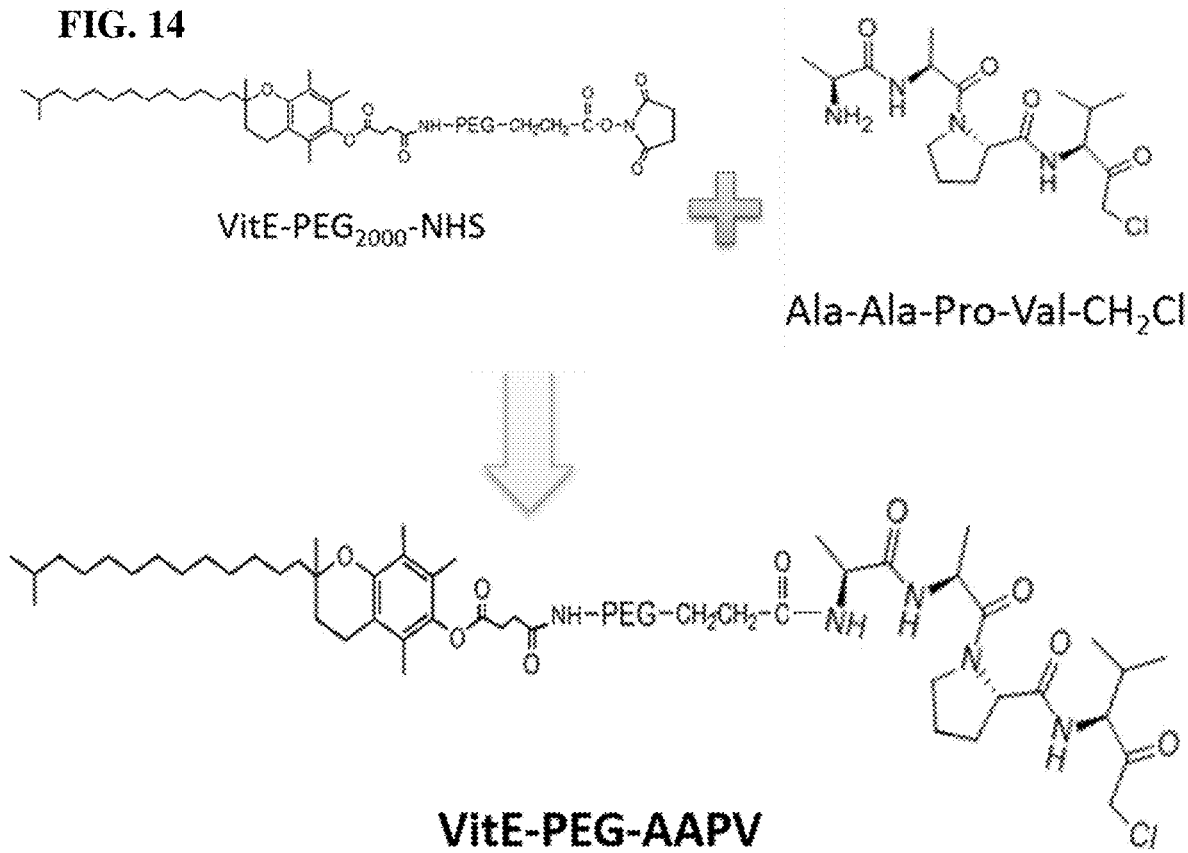

LIPOPROTEIN TARGETING PROTEASE INHIBITORS AND USES

CROSS REFERENCE TO RELATED APPLICATIONS

This application is a continuation of U.S. application Ser. No. 16/692,849, filed Nov. 22, 2019, which is a divisional of U.S. application Ser. No. 15/297,054, filed Oct. 18, 2016, which in turn claims the benefit of the earlier filing date of U.S. Provisional Application No. 62/332,277, filed May 5, 2016. The entire contents of each application is incorporated herein by reference.

FIELD

This disclosure relates to lipoprotein-targeting compounds, compositions, and systems employing a lipoprotein-targeting molecule, such as a naturally associating protein or fragment thereof, optionally included as part of a fusion molecule. Also disclosed are methods of using such compounds, compositions, and systems therapeutically, for instance to treat cardiovascular disease or protein deficiency-related diseases and conditions.

BACKGROUND

Cardiovascular disease (CVD) is the major cause of morbidity and mortality in developed countries and atherosclerosis is the major cause of CVD. Accumulation of cholesterol in the arterial wall and vascular inflammation are at the center of pathogenesis of atherosclerosis. Treatments controlling delivery of cholesterol and inflammation (statins) reduced incidence of CVD by 30-40%. There is, however, an urgent need for further reduction.

A most promising direction is complementing reduction in levels of the proatherogenic lipoproteins with increasing levels of the anti-atherogenic lipoprotein, high density lipoprotein (HDL), "HDL therapy". The success of HDL therapy depends on the method of elevation of HDL. Presently, the most successful approach is direct infusion of exogenous HDL. Infusion of reconstituted HDL (rHDL) however has considerable limitations due to high cost and requirement for intravenous delivery making it suitable mainly for acute treatment.

Epidemiological studies have clearly identified elevated plasma cholesterol as an independent risk factor for the development of CVD (Kannel et al., *Ann Intern Med* 90: 85-91, 1979). Plasma cholesterol is carried in emulsions of lipid and protein called lipoproteins. Lipoproteins exist as a polydisperse distribution of distinct particle classes most commonly classified by density as very low, low, intermediate and high-density lipoproteins. A likely overly simplistic but well accepted paradigm for the role of lipoproteins in the development CVD is that excess low density lipoproteins (LDL) promote CVD, by depositing cholesterol in atherosclerotic plaque, whereas high density lipoprotein (HDL) particles remove excess cholesterol and perhaps mediate other anti-atherogenic effects. The primary metric for assessment of CVD risk related to these lipoproteins is largely based on the cholesterol content of each of these lipoprotein particles (that is, LDL-C and HDL-C).

The major lipoprotein classes contain distinct subclasses, with different physical and chemical properties and differ in their relationship with CVD. For example, total LDL is composed of at least two subclasses: large buoyant and small dense LDL, which is particularly proatherogenic (Chapman et al., *Eur Heart J* 19 Suppl A: A24-30, 1998). The subclass distribution of HDL is much more complex; it consists of numerous distinct subclasses with varying lipid and protein compositions. Modern mass spectrometry (MS) techniques have allowed for thorough characterizations of the lipoprotein proteomes of both LDL and HDL. While LDL typically contains only a few prototypical proteins, such as apoB, apoE, apoC's etc., HDL particles may contain as many as 90 different proteins among its particle subclasses (Vaisar et al., *J Clin Invest* 117: 746-756, 2007; Karlsson et al., *Proteomics* 5: 551-565, 2005; Karlsson et al., *Proteomics* 5: 1431-1445, 2005; Davidson, The HDL Proteome Watch available online at homepages.uc.edu/~davidswm/HDLproteome.html, 2015; Gordon et al., *J Proteome Res* 9: 5239-5249, 2010). This proteomic diversity likely accounts for the dramatic functional diversity found in HDL, including numerous potential mechanisms for protection against inflammation and oxidation, as well as anti-coagulant and pro-vasodilatory functions, to name only a few (Gordon et al., *Trends Endocrinol Metab* 22: 9-15, 2011).

Alpha-1-antitrypsin (A1AT) deficiency occurs in about 1 in 2500 individuals in the United States and Europe. People with this condition develop severe liver disease and emphysema/chronic obstructive pulmonary disease (COPD). The current treatment for alpha-1-antitrypsin (A1AT) deficiency involves intravenous infusion of purified human A1AT protein. This treatment strategy is very expensive and only modestly effective. An improvement in A1AT treatment effectiveness in a mouse model of emphysema has been demonstrated by pre-incubating A1AT with high density lipoprotein (HDL) particles prior to infusion. This resulted in improvements in lung morphology and inflammatory markers in the lung compared to A1AT treatment alone. The mechanism for this improvement in function of A1AT when bound to HDL is believed to be increased trafficking of A1AT to the lung.

SUMMARY

Described herein is the development, design and construction of a class of lipoprotein targeting protease inhibitors. Peptides with protease inhibitor activity (antiprotease peptides) are conjugated to hydrophobic, lipoprotein targeting molecules using, for instance, amine reactive chemistry. Methods of use of the resultant lipoprotein targeting protease inhibitor (antiprotease) molecules are also described.

There is provided herein in a first embodiment a lipoprotein targeting protease inhibitor peptide having the generic structure: T-I, in which T is a hydrophobic entity comprising a vitamin E (VitE), an acyl chain, or cholesterol; and I is a peptide-based protease inhibitor; where T is covalently attached directly to I, or indirectly by way of a hydrophilic linker L (the latter resulting in the generic structure: T-L-I).

The protease inhibitor component I can be any of myriad peptide-based protease inhibitors (antiproteases), including peptide-based inhibitors of elastase, matrix metalloprotease (MMP), cathepsin, chymase, thrombin, coagulation factor IX, coagulation factor X, urokinase-type plasminogen activator (uPA), tissue-type plasminogen activator (tPA), and proteolytic components of the complement cascade (C1r, C1s, MASPs 1-3, C2, Factor B, Factor D or Factor I).

Optionally, the lipoprotein targeting protease inhibitor peptide may comprise a linker L, for instance which is a hydrophilic linker comprising polyethylene glycol (PEG) or succinimide. Inhibitor peptides with different length linkers are specifically contemplated.

Also provided herein are pharmaceutical compositions, comprising at least one lipoprotein targeting protease inhibitor peptide, and a pharmaceutically acceptable carrier. Optionally, the peptide in such a composition is contained in or part of a lipoprotein, such as a HDL. Methods comprising administering such a pharmaceutical composition to a subject are also provided.

Also provided are methods of producing HDL with enriched protease inhibitor (antiprotease) activity, comprising contacting HDL with a lipoprotein targeting protease inhibitor peptide as provided herein.

Yet additional embodiments are protease inhibitor enriched HDL, comprising HDL and a lipoprotein targeting protease inhibitor peptide as described herein. In examples of this embodiment, the protease inhibitor enriched HDL reconstituted HDL (rHDL).

The foregoing and other features and advantages will become more apparent from the following detailed description of several embodiments, which proceeds with reference to the accompanying figures.

BRIEF DESCRIPTION OF THE FIGURES

(FIG. 1A) Rosuvastatin effects on total plasma lipid levels (TC=total cholesterol; HDL-C=HDL cholesterol; LDL-C=LDL cholesterol; TG=triglyceride). The effect of rosuvastatin on LDL particle number (FIG. 1B) and HDL particle number (FIG. 1C) were measured by nuclear magnetic resonance. T0 and T28 are time points indicating baseline and after 28 days of rosuvastatin treatment, respectively. Data are mean±standard deviation. * indicates p<0.01.

(FIG. 5A) Individual patient spectral counts for alpha-1-antitrypsin (A1AT) in large HDL at baseline (T0) and after 28 days (T28) of rosuvastatin treatment, n=10 for each time point. The "n=5" indicator points to data from 5 subjects with a high degree of overlap. (FIG. 5B) Quantitative measurement of A1AT in large HDL by ELISA assay. (FIG. 5C) Time course of plasma A1AT concentrations during rosuvastatin treatment and after two-week washout period (Day 42 time point). * indicates p<0.05 and ** indicates p<0.01 compared to T0.

(FIG. 6A) Predicted binding of alpha-1-antitrypsin (A1AT) to a lipid surface (red spheres). Inset demonstrates that methionine residues (Met 351 and Met 358) are embedded in the lipid (white arrows) and indicates the cut site for neutrophil elastase (red arrow). (FIG. 6B) Predicted lipid binding of A1AT structure with the reactive center loop removed (A1AT Δ 346).

(FIG. 7A) Size exclusion chromatography on tandem Superdex 200 columns was used to isolate HDL bound A1AT from lipid free protein. (FIG. 7B) The ability of lipid free and rHDL bound A1AT to inhibit neutrophil elastase (NE) activity was measured by fluorometric assay.

(FIG. 9A) J774 mouse macrophages treated with increasing amounts of porcine pancreatic elastase (PPE) or heat inactivated elastase for 4 hours, TNF-α in the culture media was measured by ELISA. (FIG. 9B) J774 cells pretreated with PBS, isolated human HDL (nHDL), the same HDL enriched with alpha-1-antitrypsin (A1AT nHDL), or lipid free A1AT for 1 hour prior to PPE addition. (FIG. 9C) The ability of each of the cell treatments to inhibit elastase activity was measured in a cell-free assay. (FIG. 9D) Treatments were pre-incubated with PPE prior to addition to cells and TNF-α was measured in the culture media after 4 hours. (FIG. 9E) J774 cells were pre-incubated with each treatment for 1 hour; cells were then washed twice with PBS and placed in fresh media containing PPE and TNF-α was measured in the culture media after 4 hours. All experiments were repeated at least 3 times and were done in triplicates. Treatments were compared using one-way ANOVA and Tukey's multiple comparisons test, p<0.05 was considered significant. The letters above each treatment indicate statistical significance; within each graph, bars bearing different letters were statistically different from each other.

FIG. 13A-13B. FIG. 13A is a schematic representation of an example lipoprotein targeting protease inhibitor molecule, comprising vitamin E (VitE) linked to the elastase-inhibitory peptide AAPV-CMK (SEQ ID NO: 3). FIG. 13B is a drawing of how lipoprotein targeting protease inhibitor molecules described herein, exemplified by VitE-AAPV-CMK, interact with an HDL particle.

FIG. 14 is an overview of how the exemplary lipoprotein targeting protease inhibitor molecule VitE-AAPV is constructed from two components, VitE-PEG$_{2000}$-NHS (e.g., commercially available from NANOCS Inc., Catalog No. PG2-NSVE-2k) and the elastase inhibitor peptide, Ala-Ala-Pro-Val-CH$_2$Cl (SEQ ID NO: 2), and the resultant structure.

SEQUENCE LISTING

Figure 1A:
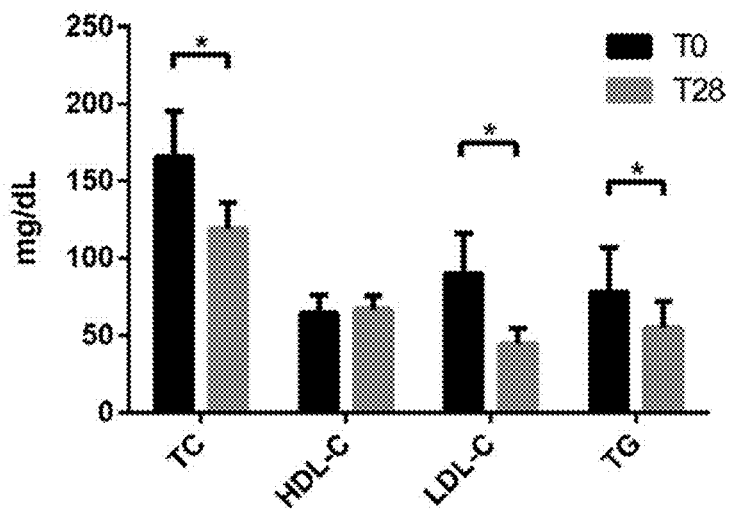
FIG. 1A-1C. Effect of rosuvastatin on plasma lipids and lipoprotein particle numbers.

The nucleic and/or amino acid sequences listed in the accompanying Sequence Listing are shown using standard letter abbreviations for nucleotide bases, and three letter code for amino acids, as defined in 37 C.F.R. 1.822. The Sequence Listing is submitted as an ASCII text file named Sequence_Listing, created on Feb. 16, 2022, and is 5955 bytes, which is incorporated by reference herein.

SEQ ID NO: 1 is the antiprotease peptide Ala-Ala-Pro-Val.

SEQ ID NO: 2 is the modified antiprotease peptide Ala-Ala-Pro-Val-CH$_2$Cl.

SEQ ID NO: 3 is the modified antiprotease peptide Ala-Ala-Pro-Val-CMK.

SEQ ID NO: 4 is the lipoprotein targeting protease inhibitor (antiprotease) molecule VitE-Ala-Ala-Pro-Val.

SEQ ID NO: 5 is the lipoprotein targeting protease inhibitor (antiprotease) molecule VitE-PEG-Ala-Ala-Pro-Val.

SEQ ID NO: 6 is the lipoprotein targeting protease inhibitor (antiprotease) molecule VitE-PEG-Ala-Ala-Pro-Val-CMK. Different versions of this molecule are contemplated and explicitly provided herein, with different length PEG moieties.

SEQ ID NO: 7 is the lipoprotein targeting protease inhibitor (antiprotease) molecule VitE-Ala-Ala-Pro-Val-CMK.

SEQ ID NO: 8 is the lipoprotein targeting protease inhibitor (antiprotease) molecule VitE-PEG-KRCCPDTCGIKCL. Different versions of this molecule are contemplated and explicitly provided herein, with different length PEG moieties SEQ ID NO: 9 is the lipoprotein targeting protease inhibitor (antiprotease) molecule VitE-PEG-KRMMPDTMGIKML. Different versions of this molecule are contemplated, with different length PEG moieties SEQ ID NO: 10 is the lipoprotein targeting protease inhibitor (antiprotease) molecule VitE-PEG-EEIIMD. Different versions of this molecule are contemplated, with different length PEG moieties SEQ ID NO: 11 is the thrombin and/or coagulation factors IX and X inhibitor peptide Hirudin (MTYTDCTESGQNLCLCEG-SNVCGQGNKCILGSDGEKNQCVTGEGTPKPQSHN DGDFEEIPEEYLQ).

SEQ ID NO: 12 is the plasminogen inhibitor peptide aprotinin (RPDFCLEPPYTGPCKARIIRYFYNAK-AGLCQTFVYGGCRAKRNNFKSAEDCMR TCGGA).

SEQ ID NO: 13 is the lipoprotein targeting protease inhibitor (antiprotease) molecule VitE-(PEG)$_2$-Lys-Gly-Ser-Gly-Ala-Ala-Pro-Val-CMK (VitE-PEG-KGSGAAPV-CMK), which serves as a non-fluorescent equivalent to SEQ ID NO: 14. Different versions of this molecule are contemplated, with different length PEG moieties SEQ ID NO: 14 is the fluorescently labeled lipoprotein targeting protease inhibitor (antiprotease) molecule VitE-(PEG)$_2$-Lys[FITC]-Gly-Ser-Gly-Ala-Ala-Pro-Val-CMK (VitE-PEG-K$^{(F)}$GSGAAPV-CMK). Different versions of this molecule are contemplated, with different length PEG moieties.

SEQ ID NO: 15 is a peptide inhibitor of (leukocyte) elastase R$_1$-W$_p$-X$_n$-AA$_1$-AA$_2$-AA$_3$-AA$_4$-Y$_m$-R$_2$ in which AA$_1$: -Arg-, -Phg- and -Nle- or is a bond; AA$_2$: -Ala-, -Phg-, -Cit- and -Nle-; AA$_3$: -Trp-, -Val- and -Tyr-; AA$_4$: -Phg- and -Gly-; W, X and Y are independently selected from the group consisting of coded or uncoded amino acids; p, n and m range between 0 and 1; R$_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—; R$_2$ is selected from the group consisting of —NR$_3$R4, —OR3 and —SR$_3$; wherein R$_3$ and R$_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl and substituted or unsubstituted aralkyl; wherein R$_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl; and provided that when AA$_1$ is a bond, AA$_2$ is -Phg- and AA$_3$ is -Trp-. R$_1$ and R$_2$ groups are bound to the amino-terminal (N-terminal) and carboxy-terminal (C-terminal) of the peptide sequences respectively.

DETAILED DESCRIPTION

I. Abbreviations

A1AT alpha-1-antitrypsin
CMK chloromethylketone

CVD cardiovascular disease
E-AAPV vitamin E fused to the antiprotease peptide AAP, with or without a linker
FDR false discovery rate
FPLC fast protein liquid chromatography
HDL high density lipoprotein
I protease inhibitor (antiprotease) moiety
L hydrophilic linker
LCAT lecithin cholesterol acyltransferase
LDL low density lipoprotein
NE neutrophil elastase
NHS N-hydroxysuccinimide
nHDL native HDL
PPE porcine pancreatic elastase
PVD peripheral vascular disease
RCL reactive center loop
rHDL reconstituted HDL
SERPIN serine protease inhibitor
T hydrophobic, lipoprotein targeting moiety
TNF-α tumor necrosis factor alpha
VLDL very low density lipoprotein
VitE vitamin E (also, in some instances, simply "E")

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Alpha-1-antitrypsin (A1AT): A protease inhibitor belonging to the SERPIN (serum trypsin inhibitor) superfamily. Alpha 1-antitrypsin is also referred to as alpha-1 proteinase inhibitor (A1PI) because it inhibits a wide variety of proteases. It protects tissues from enzymes of inflammatory cells, especially neutrophil elastase; it also inhibits plasmin, thrombin, trypsin, chymotrypsin, and plasminogen activator. In its absence (such as in A1AT deficiency), neutrophil elastase is free to break down elastin, which contributes to the elasticity of the lungs, resulting in respiratory complications such as emphysema, or COPD (chronic obstructive pulmonary disease) in adults and cirrhosis in adults or children. Synonyms: SERPINA1, serpin peptidase inhibitor, AAT, PI, PI1, A1A, PRO2275.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, mice, rates, rabbits, horses, and cows.

Apolipoprotein A-I (apoA-I): A major protein component of high density lipoprotein (HDL) complex in plasma. Apolipoprotein A-I can promote cholesterol efflux from tissues and transport to the liver for excretion. It is a cofactor for lecithin cholesterol acyltransferase (LCAT) which is responsible for the formation of most plasma cholesteryl esters. In addition, apoA-I has many other pleiotropic effects, such as anti-inflammatory, anti-thrombotic, and improving insulin sensitivity, which mechanistically are not understood but may contribute to the anti-atherogenic effect of HDL.

In particular examples, an apoA-I protein, fragment or variant thereof is capable of promoting cholesterol efflux. For example, an apoA-I protein, fragment or variant thereof is administered to a subject to promote cholesterol efflux. Unless the context clearly indicates otherwise, the term apoA-I includes any apoA-I gene, cDNA, mRNA, or protein from any organism and is capable of promoting cholesterol efflux.

Nucleic acid and protein sequences for apoA-I are publicly available. For example, GenBank Accession Nos. NM_144772.2 (human) and NM_009692 (mouse) disclose an apoA-I nucleic acid sequence, and GenBank Accession Nos. NP_658985 (human), AAB21444 (bovine) and NP_033822 (mouse) disclose apoA-I protein sequences, all of which are incorporated by reference as provided by GenBank on May 3, 2016.

Apolipoprotein C-II (apoC-II): A 79 amino acid protein, which plays a role in plasma lipid metabolism as an activator of lipoprotein lipase (LPL). This protein includes three amphipathic helices: helix 1, residues 16-38; helix 2, residues 45-58; and helix 3, residues 64-74. The lipase-activating region of apoC-II has previously been localized to the C-terminal domain of the sequence, from about residue 56, whereas the N-terminal domain (residues 1-50) of the sequence is involved in lipid binding.

Unless the context clearly indicates otherwise, the term apoC-II includes any apoC-II gene, cDNA, mRNA, or protein from any organism and is capable of activating lipoprotein lipase. Nucleic acid and protein sequences for apoC-II are publicly available. For example, GenBank Accession No. NM_009695 (human) discloses an apoC-II nucleic acid sequence, and GenBank Accession Nos. AAH05348 (human), NP_001078821 (rat), NP_001095850 (bovine), and NP_033825 (mouse) disclose additional apoC-II protein sequences, all of which are incorporated by reference as provided by GenBank on May 3, 2016.

Atherosclerosis: The progressive narrowing and hardening of a blood vessel over time. Atherosclerosis is a common form of arteriosclerosis in which deposits of yellowish plaques (atheromas) containing cholesterol, lipoid material and lipophages are formed within the intima and inner media of large and medium-sized arteries. Treatment of atherosclerosis includes reversing or slowing the progression of atherosclerosis, for example as measured by the presence of atherosclerotic lesions and/or functional signs of the disease, such as improvement in cardiovascular function as measured by signs (such as peripheral capillary refill), symptoms (such as chest pain and intermittent claudication), or laboratory evidence (such as that obtained by EKG, angiography, or other imaging techniques).

Cardiovascular: Pertaining to the heart and/or blood vessels.

Cardiovascular disease (CVD): A group of diseases that includes, but is not limited to, angina pectoris (commonly known as "angina"), arteriolosclerosis, atherosclerosis (AS-CVD), cerebrovascular disease (such as stroke), intermittent claudication, congestive heart failure, coronary artery disease (CAD), coronary insufficiency, elevated cholesterol, ischemic heart disease, myocardial infarction, peripheral vascular disease, small vessel disease, thrombosis, transient ischemic attack, and hypertension. Atherosclerosis usually results from the accumulation of fatty material, inflammatory cells, extracellular matrices and plaque. Clinical symptoms and signs indicating the presence of CVD may include one or more of the following: chest pain and other forms of angina, shortness of breath, sweatiness, Q waves or inverted T waves on an EKG, a high calcium score by CT scan, at least one stenotic lesion on coronary angiography, and heart attack. Subclinical ASCVD can be identified by imaging tests (such as CT measures of coronary calcification, or MRI measures of coronary or aortic plaque, and/or ultrasound evidence of carotid plaque or thickening).

Cholesterol absorption inhibitor: A class of cholesterol lowering drugs that block absorption of cholesterol at the brush border of the intestine without affecting absorption of tri-glycerides or fat soluble vitamins. These drugs are not systemically absorbed and can lower cholesterol on their own (i.e. without the use of additional drugs). An exemplary cholesterol absorption inhibitor is ezetimibe (EZETROL™)

Cholesterol lowering agent: An agent that lowers the level of cholesterol in a subject, such as a pharmaceutical, vitamin, or small molecule. One of skill in the art can readily identify assays, such as blood screening, to determine the effect of cholesterol. Agents include, but are not limited to, niacin, the statins (e.g., ZOCOR™ (simvastatin), LIPITOR™ (atorvastatin), PRAVACHOL™ (pravastatin), LESCOL™ (fluvastatin), MEVACOR™ (lovastatin)), bile acid binding resins (e.g., QUESTRAN™ (cholestyramine)), and fibrates (e.g. LOPID™ (gemfibrozil), LIPIDIL MICRO™ (fenofibrate)).

Complex (complexed): Two compounds/molecules (e.g., two proteins, a protein and a lipid; a protein and a lipid particle, etc.), or fragments or derivatives thereof, are said to form a complex when they measurably associate with each other in a specific manner. Such association can be measured in any of various ways, both direct and indirect. Direct methods may include co-migration in non-denaturing fractionation conditions, for instance. Indirect measurements of association will depend on secondary effects caused by the association of the two components in the complex. Representative methods for detecting, characterizing, and measuring formation of certain complex(es) are presented herein; additional methods will be recognized by those of ordinary skill in the relevant art(s).

Coronary Artery Disease: In coronary artery disease, the coronary arteries become narrowed (stenosed) or blocked (occluded) by a gradual build-up of fat (cholesterol) within or on the artery wall, which reduces blood flow to the heart muscle. This build-up is called atherosclerotic plaque or simply plaque.

If plaque narrows the lumen or channel of the artery, it may make it difficult for adequate quantities of blood to flow to the heart muscle. If the build-up reduces flow only mildly, there may be no noticeable symptoms at rest, but symptoms such as chest pressure may occur with increased activity or stress. Other symptoms include heartburn, nausea, vomiting, shortness of breath and heavy sweating.

When flow is significantly reduced and the heart muscle does not receive enough blood flow to meet its needs (cardiac ischemia), severe symptoms such as chest pain (angina pectoris), heart attack (myocardial infarction), or rhythm disturbances (arrhythmias) may occur. A heart attack usually is the result of a completely blocked artery, which may damage the heart muscle.

There are three conventional ways to treat atherosclerotic disease: medication, surgery, and minimally invasive interventional procedures such as stent implantation, percutaneous transluminal coronary angioplasty (PTCA), intravascular radiotherapy, atherectomy and excimer laser. The purpose of these treatments is to eliminate or reduce atherosclerotic narrowing of the coronary blood vessels and hence eliminate or reduce symptoms, and in the case of coronary artery disease, decrease the risk of heart attack.

Domain: A domain of a protein or other molecule is a part of the molecule that shares common structural, physiochemical and functional features; for example hydrophobic, polar, globular, helical domains or properties, for example a DNA binding domain, an ATP binding domain, lipoprotein lipase activating domain, a membrane-inserting domain, and the like. In a particular example, a fusion molecule includes a first domain and a second domain (though they can occur in any order) one of which is hydrophobic and capable of associating with (and/or specifically targeted to) a lipoprotein (such as HDL or LDL), while the other domain ha protease activity. In embodiments described herein, the first and second domains are joined covalently to each other by way of a linker.

Dyslipidemic disorder: A disorder associated with any altered amount of any or all of the lipids or lipoproteins in the blood. Dyslipidemic disorders include, for example, hyperlipidemia, hyperlipoproteinemia, hypercholesterolemia, hypertriglyceridemia, HDL deficiency, apoA-I deficiency, and cardiovascular disease (i.e., coronary artery disease, atherosclerosis and restenosis).

Heart failure (HF): The physiological state in which cardiac output is insufficient in meeting the needs of the body and lungs. This condition is also called "congestive heart failure," and is most commonly caused when cardiac output is low and the lungs become congested with fluid due to an inability of heart output to properly match venous return. Heart failure can also occur in situations of high output, where the ventricular systolic function is normal but the heart can't process the augmentation of blood volume. This can occur in overload situation (blood or serum infusions), renal diseases, chronic severe anemia, beriberi (vitamin $B_1$/thiamine deficiency), thyrotoxicosis, Paget's disease, arteriovenous fistulae, or arteriovenous malformations. Heart failure includes left sided failure and right sided failure, wherein the left and right ventricles are affected, respectively, and biventricular failure. Ischemic heart disease (including myocardial infarction), cigarette smoking, hypertension, obesity, diabetes, and valvular heart disease are associated with increased risk of heart failure. Viral myocarditis, human immunodeficiency virus infections, connective tissue disease (such as systemic lupus erythematous), drug (cocaine) abuse, and some chemotherapeutic agents can cause heart failure.

High density lipoprotein (HDL): A class of heterogeneous lipoproteins containing lipid and protein characterized by high density (>1.063 g/mL) and small size (Stoke's diameter=5 to 17 nm). The various HDL subclasses vary in quantitative and qualitative content of lipids, apolipoproteins, enzymes, and lipid transfer proteins, resulting in differences in shape, density, size, charge, and antigenicity. Apolipoprotein A-I (Apo-AI) is the predominant HDL protein, although other apolipoproteins such as Apo-AII and those referenced in the HDL Proteome Watch (Davidson, The HDL Proteome Watch. available online at homepages.uc.edu/~davidswm/HDLproteome.html, 2015) may be present.

Epidemiological and clinical studies have established an inverse association between levels of high-density lipoprotein cholesterol (HDL-C) and risk of cardiovascular disease. More particularly, clinical administration of reconstituted HDL (rHDL) formulations has been shown to confer beneficial effects to hypercholesterolemic patients suffering from recent acute coronary syndromes (ACS).

HDL can be isolated by a number of different methods, including for instance ultracentrifugation (e.g., double-step ultracentrifugation in a potassium bromide (KBr) density gradient, interval of 1.063-1.210 g/ml) and immunosorption (e.g., using anti-Apo A-I column prepared by crosslinking polyclonal antibodies directed against Apo A-I to Sepharose beads or another column matrix). Methods of isolating natural/native HDL are within the ability of an ordinarily skilled artisan.

Alternatively, HDL can be synthesized using defined components, to provide "reconstituted" or "synthetic" HDL. Typically, reconstituted HDL formulations comprise a protein such as Apo-AI, a lipid such as phosphatidylcholine, and a detergent such as cholate or deoxycholate. In addition, cholesterol or other lipids may be included; synthetic or naturally-occurring lipids, or combinations thereof, are appropriate. Additional proteins may also be included; they may be isolated from natural or engineered biological sources, or chemically synthesized. As discussed in U.S. Pat. No. 5,652,339 (which is hereby incorporated by reference in its entirety), it may be advantageous to produce reconstituted HDL formulations without using organic solvents, which in some cases are used for dissolving the lipid component when producing rHDL formulation.

Injectable composition: A pharmaceutically acceptable fluid composition comprising at least one active ingredient, e.g. a lipoprotein targeted compound, such A1AT or a lipoprotein targeting protease inhibitor fusion molecule. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this invention are conventional; formulations are well known in the art.

Inhibiting or treating a disease: Inhibiting the full development of a disease, disorder or condition, for example, in a subject who is at risk for a disease such as atherosclerosis and cardiovascular disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Implant: A support device. For example, an implant is a device that is employed to enhance and support existing passages, channels, and conduits such as the lumen of a blood vessel. In an example, an implant is an endovascular support. In a particular example, an implant is a stent. In one example, an implant is effective to maintain a vessel open. In the present disclosure, an implant can be coated with or impregnated with one or more of the disclosed peptides to assist with the treatment of a dyslipidemic or vascular disorder.

Isolated: An "isolated" biological component (such as a nucleic acid molecule, protein or organelle) is one that has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linker: A molecule that joins two other molecules, either covalently, or through ionic, van der Waals or hydrogen bonds. In particular examples, a linker comprises polyethylene glycol (PEG), or succinimide, or another hydrophilic compound.

Lipid: A class of water-insoluble, or partially water insoluble, oily or greasy organic substances, that are extractable from cells and tissues by nonpolar solvents, such as chloroform or ether. The most abundant kinds of lipids are fats or triacylglycerols, which are major fuels for most organisms. Another class of lipids is the polar lipids, which are major components of cell membranes. The following table (Table 1) provides one way of grouping major types of lipids; these have been grouped according to their chemical structure:

TABLE 1

| Lipid type | Representative examples or sub-groups |
|---|---|
| Triacylglycerols | |
| Waxes | |
| Phosphoglycerides | phosphatidylethanolamine |
| | phosphatidylcholine |
| | phosphatidylserine |
| | phosphatidylinositol |
| | cardiolipin |
| Sphingolipids | sphingomyelin |
| | cerebrosides |
| | gangliosides |
| Sterols and their fatty acid esters | (see Table 3) |

Lipids and related molecules may also be broken down into other recognized classes, such as those shown in Table 2:

TABLE 2

| Scientific Name | Abbreviation |
|---|---|
| Lyso-Phosphatidylcholine | LY |
| Sphingomyelin | SP |
| Phosphatidylcholine | PC |
| Phosphatidylserine | PS |
| Phosphatidylinositol | PI |

TABLE 2-continued

| Scientific Name | Abbreviation |
| --- | --- |
| Phosphatidylethanolamine | PE |
| Phosphatidylglycerol | PG |
| Cardiolipin | CL |
| Free Fatty Acids | FFA |
| Monoacylglycerides | MAG |
| Diacylglycerides | DAG |
| Triacylglycerides | TAG |
| Cholesterol Esters | CE |

Also included in the term lipid are the compounds collectively known as sterols. Table 3 shows representative sterols.

TABLE 3

| Scientific Name | Molecular Formula | Common Name |
| --- | --- | --- |
| 5b-cholestan-3b-ol | $C_{27}H_{48}O$ | coprostanol |
| 5a-cholestan-3b-ol | $C_{27}H_{48}O$ | dihydrocholesterol |
| 5-cholesten-3b-ol | $C_{27}H_{46}O$ | cholesterol |
| 5,24-cholestadien-3b-ol | $C_{27}H_{44}O$ | desmosterol |
| 5-cholestan-25a-methyl-3b-ol | $C_{28}H_{42}O$ | campesterol |
| 5-cholestan-24b-methyl-3b-ol | $C_{28}H_{42}O$ | dihydrobrassicasterol |
| 5-cholesten-24b-ethyl-3b-ol | $C_{29}H_{50}O$ | b-sitosterol |
| 5,22-cholestadien-24b-ethyl-3b-ol | $C_{29}H_{48}O$ | stigmasterol |

In specific embodiments, the lipids are functional, biologically active component(s) of naturally-occurring HDL or of reconstituted high density lipoprotein (rHDL). Such lipids include phospholipids, cholesterol, cholesterol-esters, fatty acids and/or triglycerides. Preferably, the lipid is a phospholipid. Non-limiting examples of phospholipids include phosphatidylcholine (PC) (lecithin), sphingosine-1-phosphate (SiP), phosphatidic acid, phosphatidylethanolamine (PE) (cephalin), phosphatidylglycerol (PG), phosphatidylserine (PS), phosphatidylinositol (PI) and sphingomyelin (SM) or natural or synthetic derivatives thereof. Natural derivatives include egg PC, egg PG, soy bean PC, hydrogenated soy bean PC, soy bean PG, brain PS, sphingolipids, brain SM, galactocerebroside, gangliosides, cerebrosides, cephalin, cardiolipin, and dicetylphosphate. Synthetic derivatives include dipalmitoylphosphatidylcholine (DPPC), didecanoylphosphatidylcholine (DDPC), dierucoylphosphatidylcholine (DEPC), dimyristoylphosphatidylcholine (DMPC), distearoylphosphatidylcholine (DSPC), dilaurylphosphatidylcholine (DLPC), palmitoyloleoylphosphatidylcholine (POPC), palmitoylmyristoylphosphatidylcholine (PMPC), palmitoylstearoylphosphatidylcholine (PSPC), dioleoylphosphatidylcholine (DOPC), dioleoylphosphatidylethanolamine (DOPE), dilauroylphosphatidylglycerol (DLPG), distearoylphosphatidylglycerol (DSPG), dimyristoylphosphatidylglycerol (DMPG), dipalmitoylphosphatidylglycerol (DPPG), distearoylphosphatidylglycerol (DSPG), dioleoylphosphatidylglycerol (DOPG), palmitoyloleoylphosphatidylglycerol (POPG), dimyristoylphosphatidic acid (DMPA), dipalmitoylphosphatidic acid (DPPA), distearoylphosphatidic acid (DSPA), dimyristoylphosphatidylethanolamine (DMPE), dipalmitoylphosphatidylethanolamine (DPPE), dimyristoylphosphatidylserine (DMPS), dipalmitoylphosphatidylserine (DPPS), distearoylphosphatidylethanolamine (DSPE), dioleoylphosphatidylethanolamine (DOPE) dioleoylphosphatidylserine (DOPS), dipalmitoylsphingomyelin (DPSM) and distearoylsphingomyelin (DSSM). The phospholipid can also be a derivative or analogue of any of the above phospholipids.

Lipoprotein: A biochemical assembly that contains both proteins and lipids, bound to the proteins, which allow fats to move through the water inside and outside cells. There are five major groups of lipoprotein particles, which, in order of molecular size, largest to smallest, are chylomicrons, very low-density lipoprotein (VLDL), intermediate-density lipoprotein (IDL), low-density lipoprotein (LDL), and HDL. HDL contains the highest proportion of protein to cholesterol; its most abundant apolipoproteins are apo A-I and apo A-II. LDL contains apolipoprotein B, and has a core consisting of linoleate and includes esterified and non-esterified cholesterol molecules. LDL particles are approximately 22 nm in diameter and have a mass of about 3 million Daltons. Lipoprotein a, (Lp(a)) is a lipoprotein subclass; lipoprotein a consists of an LDL-like particle and the specific apolipoprotein(a) [apo(a)], which is covalently bound to the apolipoprotein B of the LDL like particle.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peripheral Vascular Disease (PVD): A condition in which the arteries and/or veins that carry blood to and from the arms, legs, soft tissues and vital organs of the body, including the heart and brain, become narrowed or occluded. This interferes with the normal flow of blood, sometimes causing pain but often causing no readily detectable symptoms. With progression of PVD, significant loss of blood flow to tissue and organs can lead to tissue death, necrosis and organ death.

The most common cause of PVD is atherosclerosis, a gradual process in which cholesterol and scar tissue build up, forming plaques that occlude the blood vessels. In some cases, PVD may be caused by blood clots that lodge in the arteries and restrict blood flow.

PVD affects about one in 20 people over the age of 50, or 8 million people in the United States. More than half the people with PVD experience leg pain, numbness or other symptoms, but many people dismiss these signs as a normal part of aging and do not seek medical help.

The most common symptom of PVD is painful cramping in the leg or hip, particularly when walking. This symptom, also known as claudication, occurs when there is not enough blood flowing to the leg muscles during exercise, such that ischemia occurs. The pain typically goes away when the muscles are rested.

Other symptoms may include numbness, tingling or weakness in the leg. In severe cases, people with PVD may experience a burning or aching pain in an extremity such as the foot or toes while resting, or may develop a sore on the leg or foot that does not heal. People with PVD also may experience a cooling or color change in the skin of the legs or feet, or loss of hair on the legs. In extreme cases, untreated PVD can lead to gangrene, a serious condition that may require amputation of a leg, foot or toes. People with PVD are also at higher risk for heart disease and stroke.

Typically most symptomatic PVD is ascribed to peripheral artery disease (PAD) denoting the above described pathology predominantly in arteries. The term PVD includes this symptomology and pathology in all classes of blood vessels.

Polyethylene glycol (PEG) and PEG linkers: Polyethylene glycol [structurally, poly(ethylene) glycol] is a chemical compound composed of repeating ethylene glycol units. PEG is a typically biologically inert, non-immunogenic chemical that confers greater water solubility to proteins, labeling tags and crosslinkers into which it is incorporated as constituent chemical group. Depending on how the constituent monomer or parent molecule(s) are defined (as ethylene glycol, ethylene oxide or oxyethylene), PEG compounds are also known as PEO (polyethylene oxide) and POE (polyoxyethylene). Purified PEG is most commonly available commercially as mixtures of different oligomer sizes in broadly or narrowly defined molecular weight (MW) ranges. For example, "PEG 600" typically denotes a preparation that includes a mixture of oligomers having an average MW of 600. Likewise, "PEG 10000" denotes a mixture of PEG molecules (n=195 to 265) having an average MW of 10,000 g/mol.

The wide selection of commercially available crosslinking reagents includes those that contain discrete-length polyethylene glycol spacers. Such PEG groups increase reagent and conjugate solubility, minimize toxic and immunological effects compared to non-PEG spacers, and provide several options for accommodating specific crosslinking distances. Commercially available PEG compounds include: Amine-reactive Pegylation Reagents (which contain an NHS ester group at one end); Amine-reactive Pegylated Crosslinkers; Sulfhydryl-reactive Pegylated Crosslinkers; and Bifunctional Pegylated Crosslinkers (e.g., amine-to-sulfhydryl linkers that contain an NHS ester at one end and a maleimide group at the other).

Peptide: A polymer in which the monomers are amino acid residues which are joined together through amide bonds. When the amino acids are alpha-amino acids, either the L-optical isomer or the D-optical isomer can be used. The terms "peptide" or "polypeptide" as used herein are intended to encompass any amino acid sequence and include modified sequences such as glycoproteins. The term "peptide" is specifically intended to cover naturally occurring peptides, as well as those which are recombinantly or synthetically produced. The term "residue" or "amino acid residue" includes reference to an amino acid that is incorporated into a peptide, polypeptide, or protein.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phospholipid: A phospholipid consists of a water-soluble polar head, linked to two water-insoluble non-polar tails (by a negatively charged phosphate group). Both tails consist of a fatty acid, each about 14 to about 24 carbon groups long. When placed in an aqueous environment, phospholipids form a bilayer or micelle, where the hydrophobic tails line up against each other. This forms a membrane with hydrophilic heads on both sides. A phospholipid is a lipid that is a primary component of animal cell membranes.

Purified: The term purified does not require absolute purity; rather, it is intended as a relative term. Thus, for example, a purified compound preparation is one in which the compound is more enriched than the compound is in its generative environment, for instance within a cell or in a biochemical reaction chamber. In some embodiments, a preparation of compound is purified such that the compound represents at least 50% of the content of the preparation.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Serpins: A superfamily of proteins with similar structures that were first identified for their protease inhibition activity. The acronym serpin was originally coined because the first serpins to be identified act on chymotrypsin-like serine proteases (serine protease inhibitors). They have an unusual mechanism of action: they irreversibly inhibit their target protease by undergoing a large conformational change to disrupt its active site. This contrasts with the more common competitive mechanism for protease inhibitors that bind to and block access to the protease active site. Protease inhibition by serpins controls an array of biological processes, including coagulation and inflammation, and consequently these proteins are the target of medical research.

Most serpins are protease inhibitors, targeting extracellular, chymotrypsin-like serine proteases. These proteases possess a nucleophilic serine residue in a catalytic triad in their active site. Examples include thrombin, trypsin, and human neutrophil elastase. Serpins act as irreversible, suicide inhibitors by trapping an intermediate of the protease's catalytic mechanism. Although most serpins control proteolytic cascades, some proteins with a serpin structure are not enzyme inhibitors, but instead perform diverse functions such as storage (as in egg white-ovalbumin), transport as in hormone carriage proteins (thyroxine-binding globulin, cortisol-binding globulin), and molecular chaperoning (HSP47). The term serpin generally is used to describe these members as well, despite their non-inhibitory function, since they are evolutionarily related.

Statin: Any of a class of lipid-lowering drugs that reduce serum cholesterol levels by inhibiting a key enzyme involved in the biosynthesis of cholesterol, namely HMG-CoA reductase (3-hydroxy-3-methyl-glutaryl-CoA reductase). Example statins include atorvastatin (LIPITOR®), fluvastatin (LESCOL®), lovastatin (MEVACOR®, ALTOCOR®, not marketed in the UK), pravastatin (PRAVACHOL®, SELEKTINE®, LIPOSTAT®), rosuvastatin (CRESTOR®), simvastatin (ZOCOR®). There are two groups of statins: (1) Fermentation-derived: such as lovastatin, simvastatin and pravastatin, and (2) Synthetic statins: such as fluvastatin, atorvastatin, cerivastatin and rosuvastatin.

Statins also have indirect effects on cholesterol metabolism by upregulating hepatic expression of the LDL receptor and thus can lower circulating LDL-C by as much as 50% and provide significant protection against CVD (Baigent et al., *Lancet* 366: 1267-1278, 2005). There is also growing evidence that the statins provide cardiovascular protection by mechanisms that are independent of their LDL-C lowering effect, including anti-inflammatory and anti-apoptotic activities and also by improving endothelial cell function (Jain & Ridker, *Nat Rev Drug Discov* 4: 977-987, 2005). The mechanisms, however, by which statins mediate these so called pleiotropic effects on atherosclerosis are largely unknown.

Stroke (ischemic stroke): The rapidly developing loss of brain function due to a disturbance in the blood supply to the brain. There are two categories of stroke, "ischemic stroke" and "hemorrhagic stroke." Ischemic stroke refers to a condition that occurs when an artery to or in the brain is partially or completely blocked such that the oxygen demand of the tissue exceeds the oxygen supplied. Ischemic stroke is also referred to as "cerebral ischemia." Deprived of oxygen and other nutrients following an ischemic stroke, the brain suffers damage as a result of the stroke. Ischemic stroke is by far the most common kind of stroke, accounting for about 80% of all strokes.

Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism). Another cause of stroke is blood clots in the heart, which can occur as a result of irregular heartbeat (for example, atrial fibrillation), myocardial infarction, or abnormalities of the heart valves, such as aortic valvular insufficiency.

Therapeutically effective amount: A quantity of a specified agent (or combination of agents) sufficient to achieve a desired effect in a subject being treated with that agent.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vasculopathy: A disease of the blood vessels. An "age-related vasculopathy" is a disease of the blood vessels that is associated with advanced age. One specific, non-limiting vasculopathy is atherosclerosis. Other vasculopathies include, but are not limited to, diabetic associated vasculopathy, hypertension associated vasculopathy, Burger's disease associated vasculopathy and scleroderma associated vasculopathy. It is understood that "endothelial dysfunction" typically refers to an insufficiency in the production or response to nitric oxide.

Vasoconstriction: The diminution of the caliber or cross-sectional area of a blood vessel, for instance constriction of arterioles leading to decreased blood flow to a body part. This can be caused by a specific vasoconstrictor, an agent (for instance a chemical or biochemical compound) that causes, directly or indirectly, constriction of blood vessels. Such an agent can also be referred to as a vasohypertonic agent, and is said to have vasoconstrictive activity. A representative category of vasoconstrictors is the vasopressor (from the term pressor, tending to increase blood pressure), which term is generally used to refer to an agent that stimulates contraction of the muscular tissue of the capillaries and arteries.

Vasoconstriction also can be due to vasospasm, inadequate vasodilatation, thickening of the vessel wall, or the accumulation of flow-restricting materials on the internal wall surfaces or within the wall itself. Vasoconstriction is a major presumptive or proven factor in aging and in various clinical conditions including progressive generalized atherogenesis, myocardial infarction, stroke, hypertension, glaucoma, macular degeneration, migraine, hypertension and diabetes mellitus, among others.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Vitamin E: Term that refers to a group of compounds that include tocopherols and tocotrienols. The molecules that contribute α-tocopherol activity in a vitamin E preparation are four tocopherols and four tocotrienols, identified by the prefixes alpha-(α-), beta- (β-), gamma- (γ-), and delta- (δ-). Natural tocopherols occur in the RRR-configuration only; synthetic forms contain eight different stereoisomers and may be referred to as 'all-rac'-α-tocopherol. Of the many different forms of vitamin E, γ-tocopherol a common form found in the North American diet; γ-tocopherol can be found in corn oil, soybean oil, margarine, and dressings. α-tocopherol, the most biologically active form of vitamin E, is the second-most common form of vitamin E in the diet. This variant can be found most abundantly in wheat germ oil, sunflower, and safflower oils. Vitamin E preparations (either single compounds or mixtures) can readily be obtained commercially.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

There is provided herein in a first embodiment a lipoprotein targeting protease inhibitor peptide having the generic structure: T-I, in which T is a hydrophobic entity comprising a vitamin E (VitE), an acyl chain, or cholesterol; and I is a peptide-based protease inhibitor; where T is covalently attached directly to I, or indirectly by way of a hydrophilic linker L (the latter resulting in the generic structure: T-L-I).

In example embodiments of the lipoprotein targeting protease inhibitor peptide of, the hydrophobic lipoprotein targeting moiety T is a vitamin E selected from the group consisting of: alpha-tocopherol, beta-tocopherol, gamma-tocopherol, delta-tocopherol, alpha-tocotrienol, beta-tocotrienol, gamma-tocotrienol, or delta-tocotrienol. In additional example embodiments, T is an acyl chain 4 to 24 carbons in length, with any degree of hydrogen saturation.

The protease inhibitor component I can be any of myriad peptide-based protease inhibitors (antiproteases), including peptide-based inhibitors of elastase, matrix metalloprotease (MMP), cathepsin, chymase, thrombin, coagulation factor IX, coagulation factor X, urokinase-type plasminogen activator (uPA), tissue-type plasminogen activator (tPA), and proteolytic components of the complement cascade (C1r, C1s, MASPs 1-3, C2, Factor B, Factor D or Factor I). By way of example, in certain embodiments of the lipoprotein targeting protease inhibitor peptide, the peptide-based inhibitor I: inhibits elastase, and comprises the sequence Ala-Ala-Pro-Val (SEQ ID NO: 1); or inhibits elastase, and comprises the general structure $R_1$-W p-X n-$AA_1$-$AA_2$-$AA_3$-$AA_4$-Y m-$R_2$ (SEQ ID NO: 15), in which $AA_1$ is -Arg-, -Phg- and -Nle- or is a bond; $AA_2$ is -Ala-, -Phg-, -Cit- and -Nle-; $AA_3$ is -Trp-, -Val- and -Tyr-; and $AA_4$: -Phg- and -Gly-; or inhibits elastase, and comprises a constrained or β-hairpin peptide as shown in Tsai et al., Table 2 or U.S. Pat. No. 8,658,604; or inhibits elastase, and comprises Pep4 (KRCCPDTCGIKCL; positions 3-16 pf SEQ ID NO: 8) or Pep4M (KRMMPDTMGIKML; positions 3-16 of SEQ ID NO: 9); or inhibits matrix metalloprotease, and comprises the sequence of an inhibitory peptide in Ndinguri et al., *Molecules* 17:14230-14248, 2012; or inhibits cathepsin, and comprises the structure Z-Phe-Gly-NHO-Bz, in which Z=carboxybenzyl and Bz=benzyl; or inhibits cathepsin, and comprises the structure Z-Phe-Phe-DK or Z-Phe-Phe-$CHN_2$; or inhibits chymase, and comprises the structure Z-Arg-Glu-Thr-Phep$(OPh)_2$; or inhibits thrombin and/or coagulation factors IX and X, and is selected from Hirudin (SEQ ID NO: 11) or a derivative thereof, such as Lepirudin or Desirudin; or inhibits plasminogen activator, and comprises aprotinin (SEQ ID NO: 12) or the plasminogen activator inhibitor type 1 (PAI-1)-derived peptide EEIIMD (positions 3-8 of SEQ ID NO: 10). In yet another embodiment, the peptide-based inhibitor inhibits elastase and comprises Ala-Ala-Pro-Val-chloromethylketone (AAPV-CMK) (SEQ ID NO: 3).

Optionally, the lipoprotein targeting protease inhibitor peptide may comprise a linker L, for instance which is a hydrophilic linker comprising polyethylene glycol (PEG) (of any length, for instance of MW 1000, 2000, 2500, 5000, and so forth) or succinimide.

Specifically contemplated lipoprotein targeting protease inhibitor peptides comprising the structure: VitE-AAPV (SEQ ID NO: 4); VitE-PEG-AAPV (SEQ ID NO: 5); VitE-PEG-AAPV-CMK (SEQ ID NO: 6); VitE-AAPV-CMK (SEQ ID NO: 7); VitE-PEG-KRCCPDTCGIKCL (SEQ ID NO: 8); VitE-PEG-KRMMPDTMGIKML (SEQ ID NO: 9); VitE-PEG-EEIIMD (SEQ ID NO: 10); VitE-PEG-hirudin; VitE-PEG-lepirudin; VitE-PEG-desirudin; SEQ ID NO: 13; or SEQ ID NO: 14.

Also provided herein are pharmaceutical compositions, comprising at least one lipoprotein targeting protease inhibitor peptide, and a pharmaceutically acceptable carrier. Optionally, the peptide in such a composition is contained in or part of a lipoprotein, such as a HDL.

Methods comprising administering such a pharmaceutical composition to a subject are also provided. By way of example, such a method may be a method of treating a protease-mediated disease or defect in the subject. In embodiments of these methods, the I component in the lipoprotein targeting protease inhibitor peptide is selected to complement/treat the protease-mediated disease or defect of the subject.

Also provided are methods of producing HDL with enriched protease inhibitor (antiprotease) activity, comprising contacting HDL with a lipoprotein targeting protease inhibitor peptide as provided herein. In embodiments of such methods, the HDL is reconstituted HDL (rHDL) and the method is carried out ex vivo. In other embodiments of such methods, contacting HDL with the lipoprotein targeting protease inhibitor peptide occurs in the bloodstream of a subject. Also provided herein are protease inhibitor enriched HDL produced by these methods.

Yet additional embodiments are protease inhibitor enriched HDL, comprising HDL and a lipoprotein targeting protease inhibitor peptide as described herein. In examples of this embodiment, the protease inhibitor enriched HDL reconstituted HDL (rHDL).

IV. Passenger Protein-Enriched HDL and Uses Thereof

It has been shown that HDL particles can be "loaded" with therapeutic proteins, including native anti-proteases and antioxidants. Such therapeutic-protein enriched HDLs are proposed for use in various therapeutic contexts. See, for instance, International Application Publication No. WO2011006994 A1, entitled "HDL COMPRISING A THERAPEUTIC AGENT AND USE IN THERAPY", which teaches methods to make and use HDL that comprise an agent such as an antiprotease, antioxidant, anti-mitotic, iron metabolism agent, or anti-apoptotic agent, for use as a medicament. The teachings of that publication are hereby incorporated herein by reference in their entirety.

Conditions treatable with the A1AT-enriched HDL particles include, but are not limited to, hyperlipidemia (e.g., hypercholesterolemia), cardiovascular disease (e.g., atherosclerosis), restenosis (e.g., atherosclerotic plaques), peripheral vascular disease, acute coronary syndrome, reperfusion myocardial injury, asthma, A1AT deficiency, chronic pulmonary obstructive disorder and the like.

V. Lipoprotein-Targeting Protease Inhibitor Peptides (Fusions) and Uses Thereof Described herein is the discovery and development of lipoprotein-targeting protease inhibitor peptides, for instance which can target protease inhibitor peptides (rather than native, full-length protease proteins) to lipoproteins, including specifically HDL particles.

The prototypical lipoprotein-targeting protease inhibitor fusion protein includes a small peptide inhibitor of elastase (for instance, a small peptide derived from A1AT) attached via a hydrophillic linker molecule to a hydrophobic "targeting" moiety (having affinity for a lipoprotein, such as HDL) such as vitamin E, an acyl chain, or cholesterol or the like. The lipoprotein targeting protease inhibitor peptides provided herein present several significant advances upon the prior existing methods for treating A1AT deficiency. Full length A1AT protein is replaced with a known small peptide inhibitor of elastase (the natural target protease of A1AT), a small tetra-peptide with the sequence Ala-Ala-Pro-Val-chloromethyl ketone (CMK) (SEQ ID NO: 3). This peptide is conjugated to a lipoprotein targeting motif using amine reactive chemistry. By way of example, the peptide has been linked to a Vitamin E molecule with a polyethylene glycol spacer arm to distance the functional AAPV peptide from the targeting moiety and to provide improved solubility. This approach is expected to provide improved efficacy over the current standard of care (A1AT infusion) because, for instance, the binding of A1AT to HDL has been shown to provide greatly improved efficacy in animal models of COPD (Meilhac et al., *Handb Exp Pharmacol.* 224:509-526, 2015). This is because HDL facilitates the movement of AAT to sites of inflammation. This tissue targeting effect is expected to be recapitulated with the lipid-targeted fusion peptide structures described herein. Additionally, the resultant peptide is a small molecule of about 2.5 kDa, much smaller than the full length A1AT protein (52 kDa). An HDL particle can generally accommodate only one molecule of A1AT, whereas many copies of our VitE-PEG-AAPV peptide can reside on an HDL particle providing a significant increase in potency. Similar benefits are realized with additional embodiments of the provided lipoprotein-targeted antiprotease molecules, using alternative antiprotease peptides such as serpins and fragments thereof. Thus, the prototypical targeted antiprotease peptide can be modified to inhibit almost any protease by modifying its protease inhibitor moiety.

With the provision herein of a prototype lipoprotein-targeting protease inhibitor fusion peptide, there is now enabled an entire genus of such peptides. Thus, there are provided herein lipoprotein targeting protease inhibitors with the following generalized design:

T-I in which T (the targeting domain) is a hydrophobic component, such as Vitamin E (alpha, beta, gamma, or delta tocopherol or tocotrienol), an acyl chain (a fatty acid ranging in chain length from 4 to 24 carbon atoms with any degree of hydrogen saturation), or cholesterol; component I is a peptide inhibitor of a protease (an antiprotease peptide); and optionally included between T and I is a linker L (thus, T-L-I), which when present is a hydrophilic linker, for instance comprising or consisting of polyethylene glycol (PEG) or succinimide, which links the targeting (T) domain to the inhibitor (I) domain. Particularly contemplated are example constructed peptides in which the component I is a peptide derived inhibitor of Elastase, Matrix Metalloprotease, Cathepsin, Chymase, Thrombin, coagulation factors IX and X, Plasminogen activators, urokinase-type (uPA) and the tissue-type (tPA), or a proteolytic component of the complement cascade (C1r, C1s, MASPs 1-3, C2 and Factor B, Factor D and Factor I).

In some embodiments, the component I is a peptide inhibitor of (leukocyte) elastase; such peptide inhibitors are known in the art. These include peptide chloromethyl ketones described by Tuhy & Powers (*FEBS Lett* 50:359-362, 1975), including linear peptides containing electrophilic groups such as Ala-Ala-Pro-Val-Chloromethylketone (CMK) (SEQ ID NO: 3; available commercially for instance from MP Biomedicals, Santa Ana, CA). Also contemplated are peptides described in International Patent Publication WO/2010091893 ("Peptides Used in the Treatment and/or Care of the Skin, Mucous Membranes and/or Scalp and Their Use in Cosmetic or Pharmaceutical Compositions"), including those defined with the general formula (I):

$R_1$-$W_p$-$X_n$-$AA_1$-$AA_2AA_3$-$AA_4$-$Y_m$-$R_2$ (SEQ ID NO: 15) in which $AA_1$: -Arg-, -Phg- and -Nle- or is a bond; $AA_2$: -Ala-, -Phg-, -Cit- and -Nle-; $AA_3$: -Trp-, -Val- and -Tyr-; $AA_4$: -Phg- and -Gly-; W, X and Y are independently selected from the group consisting of coded or uncoded amino acids; p, n and m range between 0 and 1; $R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—; $R_2$ is selected from the group consisting of —$NR_3R_4$, —OR3 and —$SR_3$; wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl and substituted or unsubstituted aralkyl; wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl; and provided that when $AA_1$ is a bond, $AA_2$ is -Phg- and $AA_3$ is -Trp-. $R_1$ and $R_2$ groups are bound to the amino-terminal (N-terminal) and carboxy-terminal (C-terminal) of the peptide sequences respectively. Additional appropriate peptide inhibitors of elastase are described in Tsai & Hwang (*Expert Opin Ther Patents* 25:1145-1158, 2015), including the constrained or β-hairpin peptides provided in Table 2 of that paper (see also U.S. Pat. No. 8,658,604, "Template-Fixed Beta-Hairpin Peptidomimetics with Protease Inhibitory Activity").

In additional embodiments, the component I is a peptide inhibitor of matrix metalloprotease, such as those described by Ndinguri et al. (*Molecules* 17:14230-14248, 2012).

In additional embodiments, the component I is a peptide inhibitor of cathepsin. One example of such an inhibitor is Z-Phe-Gly-NHO-Bz (available commercially from Santa Cruz Biotechnology, for instance); another is Z-Phe-Phe-DK (available commercially from MP Biomedical). See also Schaschke et al. (*Biol. Chem* 383:849-852, 2002), describing epoxysuccinyl peptide-derived cathepsin B inhibitors.

In additional embodiments, the component I is a peptide inhibitor of plasmin, such as those described in Ding et al. (*Toxicon* 106:7-13, 2015).

In additional embodiments, component I is a peptide inhibitor of Chymase. On such inhibitor is Z-Arg-Glu-Thr-Phep$(OPh)_2$ (available commercially from MP Biomedical).

In additional embodiments, component I is a peptide inhibitor of Thrombin and/or coagulation factors IX and X. Such peptide inhibitors include hirudin (SEQ ID NO: 11) and derived peptides such as lepirudin and desirudin; see, for instance, Lee et al. (*Br J Clin Pharmacol* 72:581-592, 2011); Greinacher & Warkentin (*Thromb Haemost* 99:819-829, 2008).

In yet additional embodiments, component I is a peptide inhibitor of a Plasminogen activators, such as urokinase-type (uPA) and/or tissue-type (tPA). These include for instance Aprotinin (available commercially from Sigma-Aldrich), and the PAI-1-derived peptide EEIIMD (positions 3-8 of SEQ ID NO: 10) (Armstead et al., Am J Physiol Heart Circ Physiol 299:H76-H80, 2010)>

In additional embodiments, the component I is a peptide inhibitor of a proteolytic component of the complement cascade (C1r, C1s, MASPs 1-3, C2 and Factor B, Factor D and Factor I).

Specifically contemplated are lipoprotein targeting protease inhibitor peptides with the following components/structure: VitE-AAPV (SEQ ID NO: 4); VitE-PEG-AAPV (SEQ ID NO: 5); VitE-PEG-AAPV-CMK (SEQ ID NO: 6); VitE-AAPV-CMK (SEQ ID NO: 7); VitE-PEG-KRCCPDTCGIKCL (SEQ ID NO: 8); VitE-PEG-KRMMPDTMGIKML (SEQ ID NO: 9); VitE-PEG-EE-IIMD (SEQ ID NO: 10); VitE-PEG-hirudin; VitE-PEG-lepirudin; VitE-PEG-desirudin; SEQ ID NO: 13; or SEQ ID NO: 14.

Conditions treatable with A1AT-peptide (and other elastase inhibiting peptide) containing lipoprotein targeted antiprotease molecules and particles described herein include, but are not limited to, hyperlipidemia (e.g., hypercholesterolemia), cardiovascular disease (e.g., atherosclerosis), restenosis (e.g., atherosclerotic plaques), peripheral vascular disease, acute coronary syndrome, reperfusion myocardial injury, asthma, A1AT deficiency, chronic pulmonary obstructive disorder (COPD), emphysema, and the like. It is believed that HDL particles that are enriched with the herein described A1AT-peptide fusion will be directed for tissue uptake to sites of inflammation, including for instance the lung (Meilhac et al., *Handb Exp Pharmacol.* 224:509-526, 2015) (particularly useful in treating A1AT deficiency and COPD/Emphysema for instance), as well as vessel walls (Von Eckardstein et al., *Curr Opin Lipidol.* 27(3):264-273, 2016; Hazen et al., *Arterioscler Thromb Vasc Biol.* 30(2):138, 2010. doi: 10.1161/ATVBAHA.109.201897) (particularly useful for treating atherosclerosis, and unstable plaque).

The provided lipoprotein targeted antiprotease peptides can also be used in the treatment of other protease-mediated disease, including for instance HIV (Hazen et al., *Antimicrob Agents Chemother.* 51(9):3147-3154, 2007), hepatitis, and cancer. For instance, it is recognized that antiproteases are useful in the treatment of cancer. (Li et al., *Cancer Res.* 64(23):8657-65, 2004; Uetsuji, *Surg Today;* 22(5):439-442, 1992). It has also been reported that elastase is able to degrade intracellular substrates leading to increased tumor growth (Houghton et al., *Nat Med.* 16(2):219-223, 2010).

See also International Application Publication No. WO2011006994 A1 (INSERM, "HDL COMPRISING A THERAPEUTIC AGENT AND USE IN THERAPY"); Ortiz-Munoz et al., *FASEB J* 23:3129-3139, 2009; Tran-Dinh et al., *Br J Pharmacol* 169:493-511, 2013; Lapergue et al., *Stroke* 41:1536-1542, 2010; Mutharasan et al., *J Mater Chem B* 4:188-197, 2016;

Further, it is recognized that the lipoprotein targeted antiprotease peptide molecules described herein have utility in research, for instance to characterize the structure and/or function of lipoproteins as well as the peptide molecules and their component parts.

Construction or assembly of lipoprotein targeted antiprotease peptide molecules described herein can be carried out using readily available chemical synthesis processes and isolation techniques, as will be recognized by one of skill in the art. As demonstrated herein, commercially prepared and activated "T-L" conjugates (e.g. vitamin E-PEG-NHS) can be utilized in making fusion peptides of the discloser. In such examples, synthesis of the final desired "T-L-I" structure involves conjugation of the TL and I via NHS chemistry.

Methods for synthesis of cholesterol-derivatized (and other lipid-derivatized) peptides are known in the art. The cholesterol (or other lipid) moiety is generally attached to the peptide via a thioether linkage with the thiol group of an extra cysteine residue, added C-terminally to the select (protease inhibitory) sequence. A thioether bond is generally used as an attachment point, since it provides both for non hydrolyzable anchoring to the membrane, and for an easy preparation of the vaccine via chemoselective methods. Chemoselective reaction between bromoacetyl groups and free thiols are described, for instance, in Zeng et al., *Vaccine* 19, 3843-3852, 2001 (incorporated herein by reference).

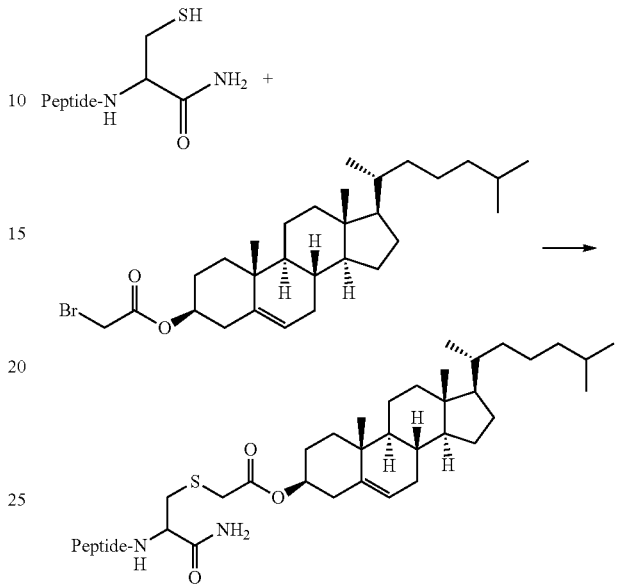

Bromoacetyl compounds can be made using commercially available compounds or by well-known methods from commercially available compounds. For instance, a method for synthesizing Bromoacetyl-cholesterol (below) is provided in International Application Publication No. WO2009053339 A2, which is incorporated herein by reference.

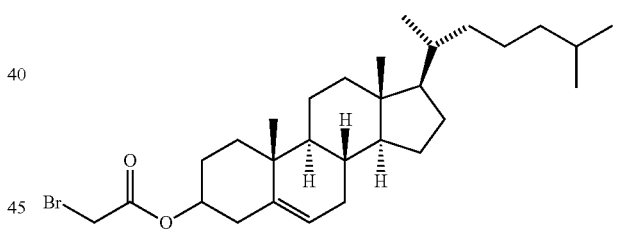

Similar techniques can be used to produce other bromoacetyl-lipids for use in fusion molecules as described herein.

As illustrated in the Examples with vitamin E-PEG-NHS starting materials, cholesterol is also commercially available as cholesterol-PEG-NHS for use in amine reactive chemistry, for instance from Nanocs Inc. (NY) and other commercial sources.

Optionally, additional embodiments of a linker for use with the disclosed conjugate peptides is a heterobifunctional polyalkyleneglycol linker having the general structure shown below:

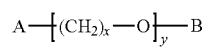

wherein A and B include different reactive groups, x is an integer from 2 to 10 (such as 2, 3 or 4), and y is an integer from 1 to 50, for example, from 2 to 30 such as from 3 to 20 or from 4 to 12. One or more hydrogen atoms can be substituted for additional functional groups such as hydroxyl groups, alkoxy groups (such as methoxy and ethoxy), halogen atoms (F, Cl, Br, I), sulfato groups and amino groups (including mono- and di-substituted amino groups such as dialkyl amino groups.

A and B of the linker can independently include a carbonyl-reactive group, an amine-reactive group, a thiol-reactive group or a photo-reactive group, but are not the same. Examples of carbonyl-reactive groups include aldehyde- and ketone-reactive groups like hydrazine derivatives and amines. Examples of amine-reactive groups include active esters such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like. Examples of thiol-reactive groups include non-polymerizable Michael acceptors, haloacetyl groups (such as iodoacetyl), alkyl halides, maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent. Examples of photo-reactive groups include aryl azide and halogenated aryl azides. Alternatively, A and/or B can be a functional group that reacts with a specific type of reactive group. For example, A and/or B can be an amine group, a thiol group, or a carbonyl-containing group that will react with a corresponding reactive group (such as an amine-reactive group, thiol-reactive group or carbonyl-reactive group, respectively) that has been introduced or is otherwise present on a hapten and/or a tyramine or tyramine derivative. Additional examples of each of these types of groups will be apparent to those skilled in the art. Further examples and information regarding reaction conditions and methods for exchanging one type of reactive group for another are provided in Hermanson, "Bioconjugate Techniques," Academic Press, San Diego, 1996, which is incorporated by reference herein.

VI. Synthesis and Purification of the Peptide Domain

The peptide/protein-derived protease inhibitor domain of the lipoprotein-targeted inhibitor peptides of the disclosure can be prepared using virtually any technique known to one of ordinary skill in the art for the preparation of peptides. For example, the peptides can be prepared using step-wise solution or solid phase peptide syntheses, or recombinant DNA techniques, or the equivalents thereof.

A. Chemical Synthesis

Peptides for use in the fusion molecules provided herein comprised of amino acids of either the D- or L-configuration can be readily synthesized by automated solid phase procedures well known in the art. Suitable syntheses can be performed by utilizing "T-boc" or "F-moc" procedures. Techniques and procedures for solid phase synthesis are described in *Solid Phase Peptide Synthesis: A Practical Approach*, by E. Atherton and R. C. Sheppard, published by IRL, Oxford University Press, 1989. Alternatively, the multi-domain peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116: 4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). This is particularly the case with glycine containing peptides. Other methods useful for synthesizing the multi-domain peptides of the disclosure are described in Nakagawa et al., *J. Am. Chem. Soc.* 107:7087-7092, 1985.

Additional exemplary techniques known to those of ordinary skill in the art of peptide and peptide analog synthesis are taught by Bodanszky, M. and Bodanszky, A., *The Practice of Peptide Synthesis*, Springer Verlag, New York, 1994; and by Jones, J., *Amino Acid and Peptide Synthesis*, 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups.

Peptides of the disclosure comprised of amino acids of either the D- or L-configuration can also be readily purchased from commercial suppliers of synthetic peptides. Such suppliers include, for example, Advanced ChemTech (Louisville, KY), Applied Biosystems (Foster City, CA), Anaspec (San Jose, CA), and Cell Essentials (Boston, MA). Specific inhibitor peptides are also available from other sources, as will be recognized by those of ordinary skill in the art.

B. Recombinant Synthesis

If the peptide is composed entirely of gene-encoded amino acids, or a portion of it is so composed, the multi-domain peptide or the relevant portion can also be synthesized using conventional recombinant genetic engineering techniques. For recombinant production, a polynucleotide sequence encoding the multi-domain peptide is inserted into an appropriate expression vehicle, that is, a vector which contains the necessary elements for the transcription and translation of the inserted coding sequence, or in the case of an RNA viral vector, the necessary elements for replication and translation. The expression vehicle is then transfected into a suitable target cell which will express the multi-domain peptide. Depending on the expression system used, the expressed peptide is then isolated by procedures well-established in the art. Methods for recombinant protein and peptide production are well known in the art (see, e.g., Sambrook et al. (ed.), *Molecular Cloning: A Laboratory Manual*, $2^{nd}$ ed., vol. 1-3, Cold Spring Harbor Laboratory Press, Cold Spring Harbor, NY, 1989, Ch. 17 and Ausubel et al. *Short Protocols in Molecular Biology*, $4^{th}$ ed., John Wiley & Sons, Inc., 1999).

To increase efficiency of production, the polynucleotide can be designed to encode multiple units of the multi-domain peptide separated by enzymatic cleavage sites. The resulting polypeptide can be cleaved (e.g., by treatment with the appropriate enzyme) in order to recover the peptide units. This can increase the yield of peptides driven by a single promoter. In one embodiment, a polycistronic polynucleotide can be designed so that a single mRNA is transcribed which encodes multiple peptides, each coding region operatively linked to a cap-independent translation control sequence, for example, an internal ribosome entry site (IRES). When used in appropriate viral expression systems, the translation of each peptide encoded by the mRNA is directed internally in the transcript, for example, by the IRES. Thus, the polycistronic construct directs the transcription of a single, large polycistronic mRNA which, in turn, directs the translation of multiple, individual peptides. This approach eliminates the production and enzymatic processing of polyproteins and can significantly increase yield of peptide driven by a single promoter.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus (CaMV) or tobacco mosaic virus (TMV)) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, can be used in the expression vector. For example, when cloning in bacterial systems, inducible promoters such as pL of bacteriophage $\lambda$, plac, ptrp, ptac (ptrp-lac hybrid promoter) and the like can be used. When cloning in insect cell systems, promoters such as the baculovirus polyhedron promoter can be used. When cloning in mammalian cell systems, promoters derived from the genome of mammalian cells (e.g., metallothionein promoter) or from mammalian viruses (e.g., the adenovirus late promoter, the vaccinia virus 7.5 K promoter) can be used.

C. Purification

The peptides of the disclosure can be purified by many techniques well known in the art, such as reverse phase chromatography, high performance liquid chromatography, ion exchange chromatography, size exclusion chromatography, affinity chromatography, gel electrophoresis, and the like. The actual conditions used to purify a particular multi-domain peptide or peptide analog will depend, in part, on synthesis strategy and on factors such as net charge, hydrophobicity, hydrophilicity, and the like, and will be apparent to those of ordinary skill in the art.

For affinity chromatography purification, any antibody which specifically binds the multi-domain peptide or peptide analog may be used. For the production of antibodies, various host animals, including but not limited to, rabbits, mice, rats, and the like, may be immunized by injection with a multi-domain peptide or peptide analog. The multi-domain peptide or peptide analog can be attached to a suitable carrier (e.g., BSA) by means of a side chain functional group or linker attached to a side chain functional group. Various adjuvants may be used to increase the immunological response, depending on the host species, including but not limited to, Freund's (complete and incomplete), mineral gels (e.g., aluminum hydroxide), surface active substances (e.g., lysolecithin, pluronic polyols, polyanions, and oil emulsions), keyhole limpet hemocyanin, dinitrophenol, and potentially useful human adjuvants such as BCG (bacilli Calmette-Guerin) and *Corynebacterium parvum*.

Booster injections can be given at regular intervals, and antiserum harvested when the antibody titer thereof, as determined semi-quantitatively, for example, by double immunodiffusion in agar against known concentrations of the antigen, begins to fall. See, e.g., Ouchterlony et al., *Handbook of Experimental Immunology*, Wier, D. (ed.), Chapter 19, Blackwell, 1973. A plateau concentration of antibody is usually in the range of 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

Monoclonal antibodies to a peptide (either a domain to be used in a lipoprotein-targeting protease inhibitor fusion peptide, or the fusion peptide molecule itself) may be prepared using any technique which provides for the production of antibody molecules by continuous cell lines in culture, for example the classic method of Kohler & Milstein (*Nature* 256:495-97, 1975), or a derivative method thereof. Briefly, a mouse is repetitively inoculated with a few micrograms of the selected protein immunogen (e.g., a multi-domain peptide or peptide analog) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as enzyme-linked immunosorbent assay (ELISA), as originally described by Engvall (*Meth. Enzymol.*, 70:419-39, 1980), or a derivative method thereof. Selected positive clones can be expanded and their monoclonal antibody product harvested for use. Detailed procedures for monoclonal antibody production are described in Harlow and Lane, *Using Antibodies: A Laboratory Manual*, CSHL, New York, 1999. Polyclonal antiserum containing antibodies can be prepared by immunizing suitable animals with a polypeptide comprising at least one multi-domain peptide or peptide analog, which can be unmodified or modified, to enhance immunogenicity.

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178: 476-96, 1989; Glockshuber et al., *Biochemistry* 29:1362-67, 1990; and U.S. Pat. No. 5,648,237 (Expression of Functional Antibody Fragments); U.S. Pat. No. 4,946,778 (Single Polypeptide Chain Binding Molecules); and U.S. Pat. No. 5,455,030 (Immunotherapy Using Single Chain Polypeptide Binding Molecules), and references cited therein. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., *Current Protocols in Immunology*, Wiley, NY, 1995), agglutination assays, flocculation assays, cell panning, etc., as are well known to one of skill in the art.

Optionally, peptides and fusion molecules produced as described herein may also be purified using HPLC or other chemical laboratory means.

VII. Activity of Lipoprotein Targeting Protease Inhibitor Peptides

Once a lipoprotein targeting protease inhibitor peptide (a lipoprotein-mediated antiprotease) is produced, including variants beyond the specific examples provided herein, the function(s) of the peptide can be assayed using methods such as those described herein, or methods readily recognized by those of skill in the relevant art. Representative methods for testing activity are also provided herein, including peptide affinity for and binding/complexing with lipoprotein as well as protease activity.

VIII. Incorporation of Lipoprotein Targeting Protease Inhibitor Peptides into Lipoprotein Particles It is contemplated that the lipoprotein targeting protease inhibitor peptides described herein can be loaded/assembled into lipoprotein particles, such as HDL particles, and the resultant enriched particles used as therapeutic agents. The production/assemble of such loaded particles is similar to the type of assembly that could be used in the preparation of any functionalized rHDL or nHDL. Representative methods are described or incorporated herein In general, HDL particles for use in such embodiments can be synthetic preparations such as those described herein composed of phospholipid and human purified or recombinant apoA-I (for instance, assembled by reconstitution of dried lipids using a sterile saline solution containing apoA-I); alternatively, they can be native HDL particles isolated for instance from healthy individuals.

By way of example, lipoprotein particles, such as HDL, may be loaded (complexed, enriched) with a lipoprotein targeted antiprotease as follows: incubate HDL (either reconstituted or native) with the selected peptide agent at an appropriate concentration under gentle agitation at 37° C. for an appropriate time, the concentration and time depending on the affinity of the selected agent (and specifically, the lipoprotein targeting component T of that agent) for the HDL; separate the resultant mixture using potassium bromide gradient ultracentrifugation; and collection and purification of the enriched HDL, for instance using dialysis against a saline solution or filtered using a centrifugal device.

Alternatively, HDL may be loaded by incubating with the selected peptide agent under gentle agitation at 37° C. for an appropriate time; followed by filtration using a cut-off centrifugal device. Free agent (not associated with the HLD) partitions into the flow-through whereas enriched HDL remain in the upper compartment.

A person having ordinary skill in the art will be aware of the conditions for carrying out lipoprotein particle (e.g., HDL) loading. For example, if the agent has a low affinity with the HDL, the HDL will be incubated with a higher concentration of said agent and for a longer time, than if the agent had a natural and high affinity for the HDL. Likewise, a person of ordinary skill in the art is able to select the appropriate molecular weight cutoff of the centrifugal device for carrying out the required filtrations.

IX. Incorporation of Lipoprotein Targeting Protease Inhibitor Peptide(s) or Lipoproteins Containing Such Peptides into Pharmaceutical Compositions Pharmaceutical compositions that comprise at least one lipoprotein targeting protease inhibitor peptide, or a lipoprotein particle containing such a peptide, as described herein as an active ingredient will normally be formulated with a solid, gel (e.g., Matrigel), or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Oral formulations will usually be solid (e.g., powders, pills, tablets, or capsules, including for instance enteric coated solid delivery forms), and preferentially will comprise peptides rather than peptide-loaded lipoprotein formulations. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise lipoprotein targeting protease inhibitor peptide(s), or lipoprotein particles containing such a peptide (e.g., a protease inhibitor enriched lipoprotein particle), may be formulated in unit dosage form, suitable for individual administration of precise dosages. One possible unit dosage contains approximately 50 μg of peptide or protease inhibitor enhanced lipoprotein; alternatively, a unit dose may contain 60 μg, 70 μg, 80 μg, 90 μg, 100 μg or more. The amount of active compound administered will be dependent on the subject being treated, the severity of the affliction, and the manner of administration, and is best left to the judgment of the prescribing clinician. Within these bounds, the formulation to be administered will contain a quantity of the active component(s) in an amount effective to achieve the desired effect in the subject being treated. However, dosages ranges comparable to those currently used in lipid-free A1AT replacement therapies (for instance, 60 mg/kg weekly) may provide guidance from which ranges could be optimized.

To extend the time during which the peptide is available in the subject's system, the peptide can be provided as an implant, an oily injection, or as a particulate system. The particulate system can be a microparticle, a microcapsule, a microsphere, a nanocapsule, or similar particle (Banga, "Parenteral Controlled Delivery of Therapeutic Peptides and Proteins," in *Therapeutic Peptides and Proteins*, Technomic Publishing Co., Inc., Lancaster, PA, 1995).

In some examples, the provided peptides are combined with a pharmaceutically acceptable carrier (e.g., a phospholipid or other type of lipid) or vehicle for administration to human or animal subjects. In some embodiments, more than one disclosed peptide can be combined to form a single preparation.

Additionally, in some embodiments the therapeutic agents may be incorporated in implantable devices, such as vascular stents placed directly in diseased blood vessels in the coronary, cerebral or peripheral circulation, for instance to provide slow release of the compound, thereby providing regional sustained release of the therapeutic agents.

For subjects with peripheral artery disease (and other systemic and arterial diseases), administration is, for example, by intra-arterial (particularly intracoronary), or intrapericardial injection. In some embodiments, the therapeutic agent is administered systemically, such as by intravenous injection. Additionally, in some embodiments the therapeutic agents may be incorporated into or on an implantable device, such as vascular stents placed directly in diseased blood vessels in the coronary or cerebral circulation, and undergo slow release providing regional sustained release of the therapeutic agents. Efficacy of treatment is demonstrated, for example, by a regression of symptoms, for example chest pressure or pain.

In another embodiment, it may be desirable to administer the pharmaceutical compositions locally to the area in need of treatment. This may be achieved by, for example, and not by way of limitation, local or regional infusion or perfusion during surgery, injection, catheter, suppository, or implant (e.g., implants formed from porous, non-porous, or gelatinous materials, including membranes, such as silastic membranes or fibers), and the like.

In a specific embodiment, one or more of the disclosed anti-protease peptides may be associated either by coating or impregnating an implant such as stent, for instance to treat a dyslipidemic or vascular disorder. These peptides are prepared and purified as described herein. In an example, the implant can be partially or completely coated with the peptide. For instance, the luminal surface of the implant may be coated with the peptide. Such configuration is believed to reduce atherosclerotic plaques in arteries often associated with atherosclerosis while minimizing the amount of coating material and time required to prepare the implant. The peptide may be attached to the implant by any chemical or mechanical bond or force, including linking agents. Alternatively, the coating may be directly linked (tethered) to the first surface, such as through silane groups. In other examples, the implant may be impregnated with at least one peptide by methods known to those of skill in the art so that multiple surfaces (such as the outer and inner surfaces) of the implant include the peptide.

In an additional embodiment, the implant may be coated or impregnated with materials in addition to the disclosed peptides to further enhance their bio-utility. Examples of suitable coatings are medicated coatings, drug-eluting coatings, hydrophilic coatings, smoothing coatings.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. An example of such a dosage range is 0.1 to 200 mg/kg body weight in single or divided doses. Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration. Those of ordinary skill in the art will know appropriate volumes for different routes of administration (for example, exemplary delivery methods include, but are not limited to, those provides by Malik et al., "Recent Advances in Protein and Peptide Drug Delivery Systems" *J. Curr. Drug Deliv.* 4(2): 141-151, 2007 which is hereby incorporated by reference in its entirety).

X. Pharmaceutical Compositions and Uses Thereof

The peptides or peptide-enhanced lipoproteins of the disclosure (and mixtures thereof) can be used to treat any disorder in animals, especially mammals (e.g., humans), for which inhibiting a target protease is beneficial. Appropriate conditions will be dependent on the protease inhibitor component used in the peptide, and in fact the antiprotease peptide molecule is designed (and the protease inhibitor component chosen) with the end use in mind. Thus, for instance, conditions involving an over-abundance or undesired activity of elastase (including A1AT deficiency) are treated using a peptide that includes an elastase inhibitor component. Other proteases mentioned herein have art-recognized implications in diseases, such as inflammatory diseases, including atherosclerosis and cancer.

The peptides, peptide analogs, and loaded lipoprotein particles (such as HDL particles) can be used alone or in combination therapy with other therapeutic compositions or drugs used to treat the foregoing conditions. Such combination therapies include, but are not limited to simultaneous or sequential administration of the drugs involved. For example, in the treatment of hypercholesterolemia or atherosclerosis, the peptide, peptide analog, or lipoprotein formulations can be administered with any one or more of known cholesterol lowering therapies, for example, bile-acid resins, niacin, CETP inhibitors, reconstituted HDL therapy, fibrates, PCSK9 related therapies, and statins.

In another embodiment, it may be desirable to administer the pharmaceutical compositions locally to the area in need of treatment. This may be achieved by, for example, and not by way of limitation, local or regional infusion or perfusion during surgery, topical application (e.g., wound dressing), injection, catheter, suppository, or implant (e.g., implants formed from porous, non-porous, or gelatinous materials, including membranes, such as silastic membranes or fibers), and the like. Weekly or bi-weekly administration via intravenous infusion or subcutaneous injection is contemplated for representative embodiments.

In one embodiment, administration can be by direct injection at the site (or former site) of a tissue that is to be treated, such as the heart or the peripheral vasculature, lung, and so forth. In another embodiment, the pharmaceutical compositions are delivered in a vesicle, in particular liposomes (see, e.g., Langer, *Science* 249:1527-1533, 1990; Treat et al., in *Liposomes in the Therapy of Infectious Disease and Cancer*, Lopez-Berestein and Fidler (eds.), Liss, N.Y., pp. 353-365, 1989).

In yet another embodiment, the pharmaceutical compositions can be delivered in a controlled release system. In one embodiment, a pump can be used (see, e.g., Langer *Science* 249:1527-1533, 1990; Sefton *Crit. Rev. Biomed. Eng.* 14:201-240, 1987; Buchwald et al., *Surgery* 88:507-516, 1980; Saudek et al., *N. Engl. J. Med.* 321:574-579, 1989). In another embodiment, polymeric materials can be used (see, e.g., Ranger et al., *Macromol. Sci. Rev. Macromol. Chem.* 23:61-64, 1983; Levy et al., *Science* 228:190-192, 1985; During et al., *Ann. Neurol.* 25:351-356, 1989; and Howard et al., *J. Neurosurg.* 71:105-112, 1989). Other controlled release systems, such as those discussed in the review by Langer (Science 249:1527-1533, 1990), can also be used.

XI. Kits

The peptides, peptide analogs, and lipoprotein particles disclosed herein can be supplied in the form of a kit for use in prevention and/or treatment of diseases (e.g., a protease inhibitor-deficiency). In such a kit, a clinically effective amount of one or more of the peptides or peptide-loaded/enhanced lipoprotein particles is provided in one or more containers. The peptides or particles may be provided suspended in an aqueous solution or as a freeze-dried or lyophilized powder, for instance. In certain embodiments, the peptides will be provided in the form of a pharmaceutical composition.

Kits can also include instructions, usually written instructions, to assist the user in treating a disease (e.g., such as a protease inhibitor deficiency) with a lipoprotein-targeting protease inhibitor peptides. Such instructions can optionally be provided on a computer readable medium.

The container(s) in which the protein(s) are supplied can be any conventional container that is capable of holding the supplied form, for instance, microfuge tubes, ampoules, or bottles. In some applications, chimeric proteins may be provided in pre-measured single use amounts in individual, typically disposable, tubes or equivalent containers.

The amount of a peptide (or peptide loaded lipoprotein) supplied in the kit can be any appropriate amount, depending for instance on the market to which the product is directed. For instance, if the kit is adapted for research or clinical use, the amount of each peptide or peptide loaded lipoprotein provided would likely be an amount sufficient for several treatments.

The following examples are provided to illustrate certain particular features and/or embodiments. These examples should not be construed to limit the invention to the particular features or embodiments described.

EXAMPLES

Example 1: Rosuvastatin Alters the Proteome of High Density Lipoproteins: Generation of Alpha-1-Antitrypsin (A1AT) Enriched Particles with Anti-Inflammatory Properties At least some of the research described in this Example was published Oct. 19, 2015 as Gordon et al. (*Mol & Cell Proteomics* 14:3247-3257, 2015), which is incorporated herein by reference in its entirety including supplemental material.

Statins lower plasma cholesterol by as much as 50%, thus reducing future cardiovascular events. However, the physiological effects of statins are diverse and not all are related to LDL-C lowering.

This Example describes a small clinical pilot study which assessed the impact of statins on lipoprotein-associated proteins in healthy individuals (n=10) with normal LDL-C (<130 mg/dL), who were treated with the statin rosuvastatin (available commercially as Crestor®) (20 mg/day) for 28 days. Proteomic analysis of size-exclusion chromatography isolated LDL, HDL-L (large) and HDL-S (small) fractions and spectral counting was used to compare relative protein detection before and after statin therapy. Significant protein changes were found in each lipoprotein pool and included both increases and decreases in several proteins involved in lipoprotein metabolism, complement regulation, and acute phase response.

The most dramatic effect of the rosuvastatin treatment was an increase in alpha-1-antitrypsin (A1AT) spectral counts associated with HDL-L particles. Quantitative measurement by ELISA confirmed an average 5.7-fold increase in HDL-L associated A1AT. Molecular modeling predictions indicated that the hydrophobic reactive center loop of A1AT, the functional domain responsible for its protease inhibitor activity, is likely involved in its lipid binding and its association with HDL was found to protect A1AT against oxidative inactivation. Cell culture experiments, using J774 macrophages, demonstrated that the association of A1AT with HDL enhances its anti-protease activity, preventing elastase induced production of tumor necrosis factor alpha (TNF-α).

Thus, this Example demonstrates that statins can significantly alter the protein composition of both LDL and HDL. Further, described here is a novel functional relationship between A1AT and HDL: the upregulation of A1AT on HDL enhances its anti-inflammatory functionality, which may contribute to the non-lipid lowering beneficial effects of statins.

Experimental Procedures

Subject Selection.

Fasting blood samples were obtained from ten healthy volunteers participating in a study of the NIH Center for Human Immunology, intended to evaluate effects of a statin on the immune system. This protocol was approved by the institutional review board of the National Heart, Lung, and Blood Institute (NHLBI) and registered at clinicaltrials.gov (NCT01200836); all participants provided written informed consent. Three males and seven females were enrolled, with an average age of 44.1±11 years. Participants were selected to have normal LDL-C (<130 mg/dL) and were not on any lipid modification therapy prior to the study. Recruited participants were given rosuvastatin (20 mg/day) for 28 days. Blood was collected by venipuncture at the following time points: baseline, 14 and 28 days after rosuvastatin treatment, and 14 days after stopping treatment (washout). Samples were stored at −20° C. Because samples were taken from each participant at baseline and on-treatment, each subject acted as their own control.

Lipoprotein Analysis.

Lipid and lipoprotein assays were performed on a Siemens Dimension Vista analyzer, using standard enzymatic assays. HDL-C was measured by a direct assay (Siemens) and LDL-C was determined by the Friedewald equation. Lipoprotein particle numbers and average particle sizes were determined from heparinized plasma on a Vantera Clinical Analyzer (LipoScience).

Lipoprotein Isolation by Size Exclusion Chromatography.

Collected plasma from each subject at baseline (n=10) and after 28 days of rosuvastatin treatment (n=10) was applied to two Superdex 200 columns (GE Healthcare) arranged in series on an Akta FPLC system. The flow rate was set to 0.5 mL/min and 0.5 mL fractions were collected. Fractions were assayed for phosphatidylcholine, total cholesterol, free cholesterol and triglyceride by enzymatic assays (Wako Diagnostics) to determine position of elution for lipoproteins. For each subject, fractions were combined to make LDL (elution vol. 17.5-20 mL), HDL-large (HDL-L; elution vol. 21-23 mL) and HDL-small (HDL-S; elution vol. 23-25 mL) pools, generating a total of 60 samples for MS analysis.

Lipoprotein Proteomics—Experimental Design and Statistics.

Pooled FPLC fractions were applied to a phospholipid binding resin and washed to isolate lipid bound protein components, as previously described (Gordon et al., *J Proteome Res* 9: 5239-5249, 2010). Resin bound proteins were then subjected to overnight trypsin digestion at 37° C. Resulting peptides were collected and then reduced with dithiothreitol (200 mM; 30 min at 37° C.) and carbamidomethylated with iodoacetamide (800 mM; 30 min at 25° C.). Digest solutions were dried, reconstituted in 100 µL of water+0.1% formic acid and desalted using ZipTips (Millipore), and stored at −20° C. until MS analysis.

Desalted samples were dried and reconstituted in 20 µL of water+0.1% formic acid and 10 µL was analyzed on a Thermo Orbitrap Velos Mass Spectrometer instrument. Blank runs were performed between each sample to prevent carry over. Peak lists were generated using Proteome Discoverer (version 1.3.0.339) and resulting spectra were searched against the SwissProt database (version 012214), using Mascot (version 2.4.0) to identify protein components of the lipoprotein fractions (fragment ion mass tolerance of 0.80 Da and a parent ion tolerance of 20 PPM). Search criteria included: human taxonomy, fixed modification: carbamidomethylation (C), variable modifications: oxidation (M), deamidation (N, Q) and up to two missed trypsin cleavage sites were allowed. Validation of peptide and protein identifications was performed using Scaffold software (version 4.1.1) and a 1.0% false discovery rate (FDR) for both peptide and protein thresholds and a minimum of 2 identified peptides were required per protein. Calculated decoy FDR for peptide and protein identifications were 0.03% and 0.7%, respectively. Spectral counting was used as a semi-quantitative comparison of protein abundance between baseline and on-treatment samples using normalized spectrum count calculated by the Scaffold software. Comparisons were only performed to estimate the relative abundance of the same protein in the same lipoprotein pool before and after rosuvastatin treatment; no comparisons were made between lipoprotein fractions. Data was analyzed by student's T-test to identify proteins with statistically significant (p<0.05) changes in normalized spectral counts. Because this MS analysis was intended primarily for screening purposes, to identify candidates for hypothesis driven functional experiments, the data analysis was not corrected for multiple comparisons. All MS data have been deposited to the ProteomeXchange Consortium (Vizcaino et al., *Nat Biotechnol* 32: 223-226, 2014) via the PRIDE partner repository with the dataset identifier PXD002633.

Preparation of Alpha-1-Antitrypsin Enriched HDL.

Reconstituted HDL was prepared by cholate dialysis method, using human purified apolipoprotein A-I and 1-palmitoyl-2-oleoyl-sn-glycero-3-phosphocholine (Avanti) as previously described (Matz & Jonas, *J Biol Chem* 257: 4535-4540, 1982). Native human HDL was isolated from plasma by sequential density gradient ultracentrifugation (Chapman et al., *J Lipid Res* 22: 339-358, 1981). Reconstituted or native HDL was co-incubated with alpha-1-antitrypsin protein (Human, Sigma Aldrich) overnight at 37° C. Unbound A1AT was removed by filtration, using Amicon Ultra 100 kDa centrifugal filter units (Millipore). Elastase activity assays were performed with the EnzChek® elastase assay kit (Life Technologies).

Cell Culture Experiments.

J774 mouse macrophages were used to examine the potential functional role of alpha-1-antitrypsin enriched HDL in inflammation. For these experiments, cells were plated in 12-well culture plates at a density of $1 \times 10^5$ cells/well two days prior to the experiment. Cells were washed twice with PBS and placed in serum-free media for 1 hour prior to addition of treatment. Treatments (PBS, nHDL, A1AT-HDL or A1AT) were added to serum-free culture media: HDL protein was matched for nHDL and A1AT-nHDL at a final concentration of 200 µg/mL. A1AT concentration was matched between free A1AT and A1AT-nHDL at a final concentration of 2 µM. Cells were then incubated with elastase (porcine pancreas, Sigma Aldrich, 500 nM) for 4 hours and media was collected and centrifuged at 3,000×g for 5 min to pellet any loose cells or debris and supernatant was transferred to fresh tubes and stored at −80° C. until further analysis. Elisa assays for mouse TNF-α (BioLegend) were performed on cell culture media.

Results

Effect of Rosuvastatin on Lipoprotein Lipid Composition and Particle Numbers.

Figure 1B:
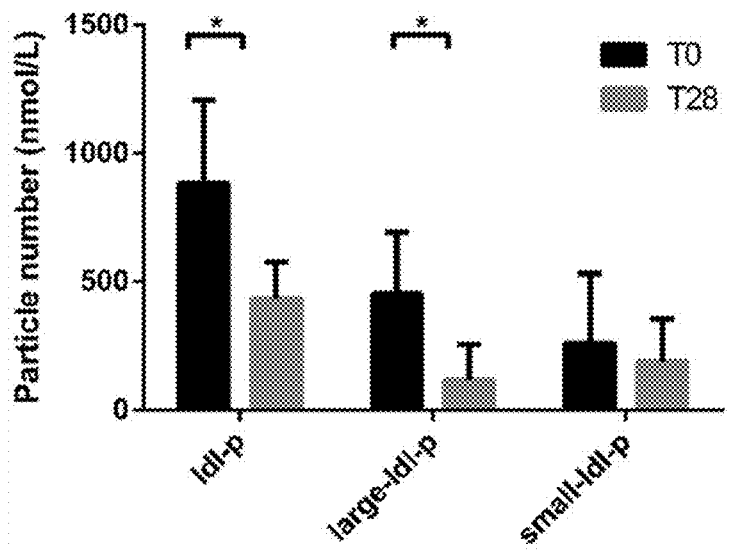
Figure 1C:
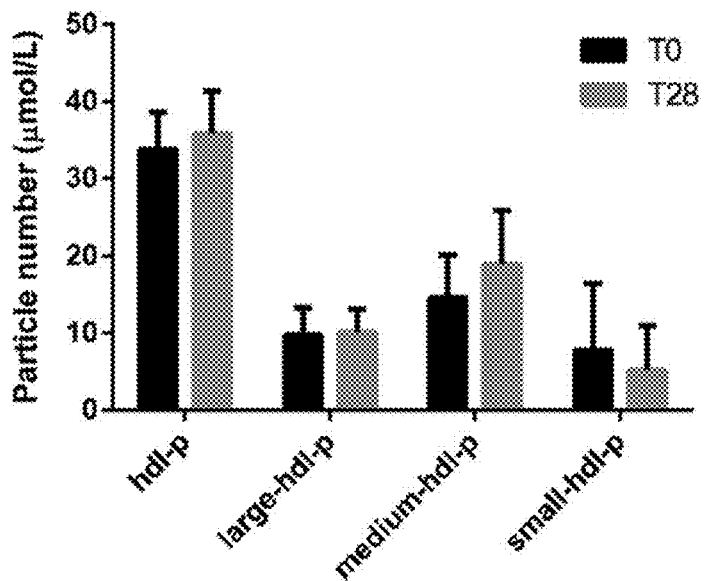

Serum samples from subjects at baseline and after 28 days of rosuvastatin therapy were analyzed for plasma lipids (FIG. 1A). As expected, treatment with rosuvastatin resulted in reductions in total cholesterol (−28%; p<0.001), LDL-C (−50%; p<0.001) and triglyceride (−29%; p<0.01) (FIG. 1A). There was a modest 3.6% increase of HDL-C that was not statistically significant, although this effect of statins has been confirmed in larger studies (McTaggart & Jones, *Cardiovasc Drugs Ther* 22: 321-338, 2008). The effect of rosuvastatin on lipoprotein particle numbers mirrored the effects on the lipid levels. LDL particle number (LDL-p) was reduced by 51% (p<0.001), which was predominantly due to reduction of large LDL (FIG. 1B). HDL-p was increased by 6.2% but was not statistically significant (FIG. 1C).

Figure 2:
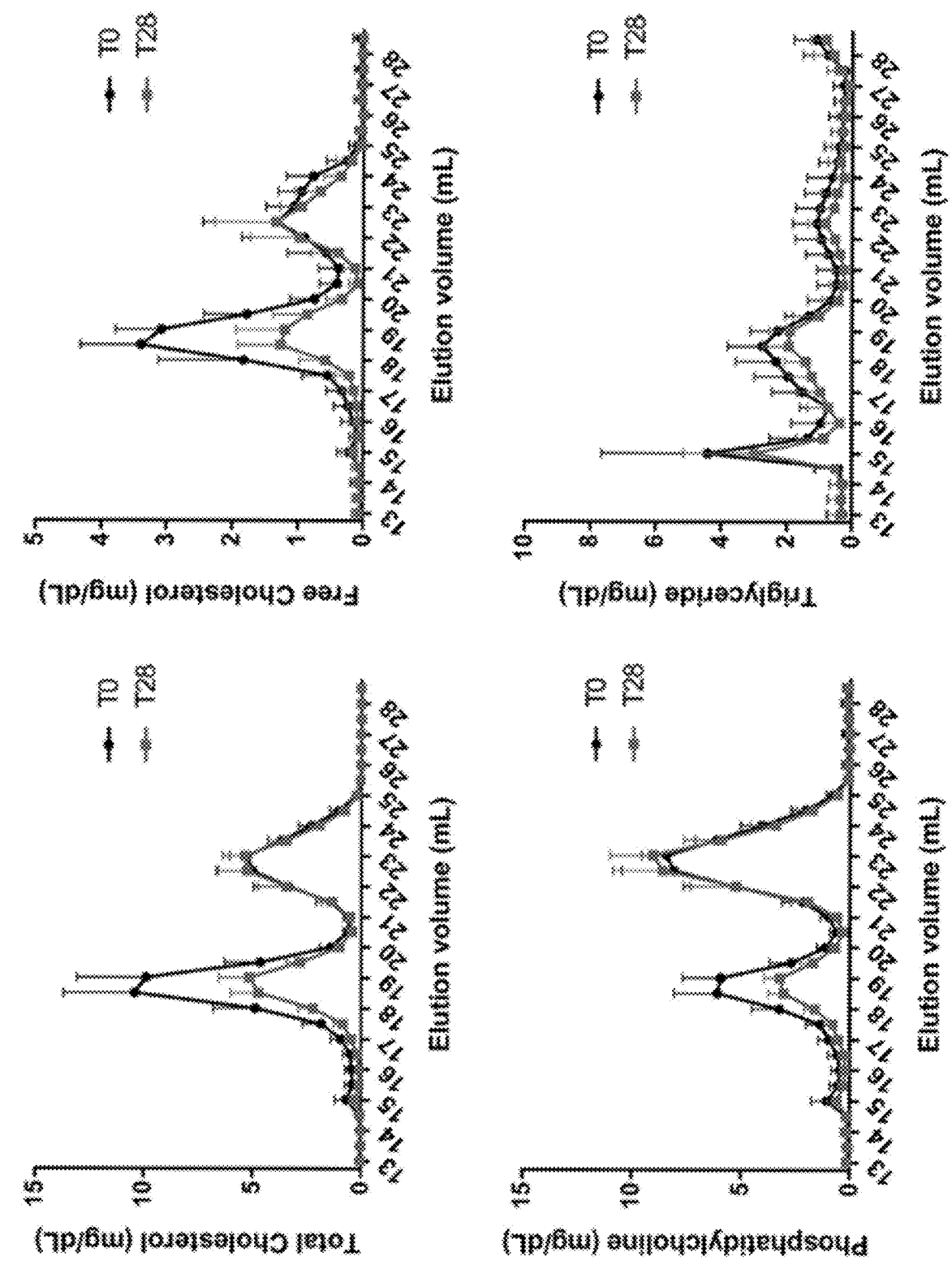
FIG. 2. Effect of rosuvastatin on plasma lipid distributions by size exclusion chromatography. Plasma from patients at baseline (T0) and after 28 days (T28) of rosuvastatin treatment was separated on two Superose 6 columns arranged in series. Collected fractions were analyzed for total cholesterol, free cholesterol, phosphatidylcholine and triglyceride. Data are mean±standard deviation.

Serum was separated by gel exclusion chromatography to isolate lipoproteins by size. Collected fractions were analyzed for total cholesterol, free cholesterol, phosphatidylcholine, and triglycerides (FIG. 2). Results from this analysis, indicate a reduction in lipids associated with the LDL peak (Elution volume=17-20 mL). This is consistent with the clinical lipid measures presented in FIG. 1. As before, no major effect on HDL lipids (Elution volume=21-25 mL) was observed.

Mass Spectrometry Analysis of Lipoprotein Proteome.

Figure 3:
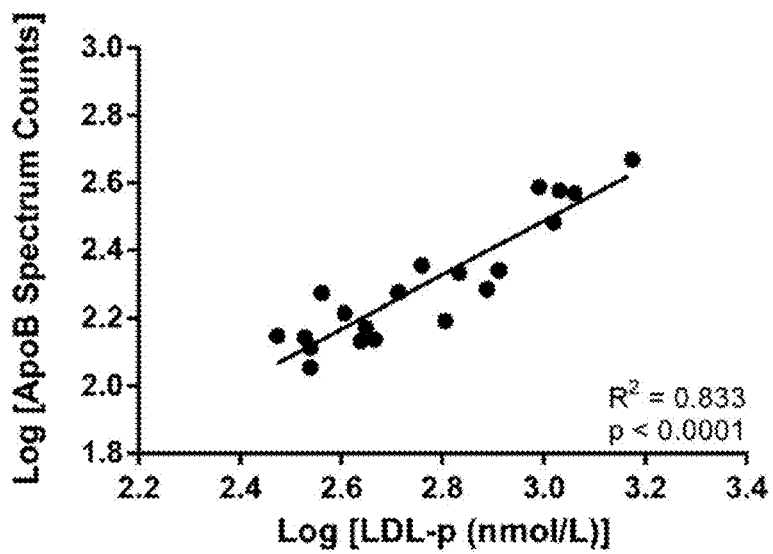
FIG. 3. ApoB spectral counts correlate with LDL particle number. As validation of the semi-quantitative potential of spectral counting under our experimental conditions we compared spectral counts for apolipoprotein B (apoB) vs. LDL particle number. ApoB is a core protein of LDL and has a well-established 1:1 (mol apoB:mol LDL) stoichiometry.

To test our hypothesis that rosuvastatin alters the lipoprotein proteome, we pooled fractions containing LDL and HDL and used mass spectrometry (MS) to analyze the lipid associated protein content of each of these lipoproteins in each subject at baseline and after 28 days on rosuvastatin. The HDL peak was divided into two halves, representing large and small HDL, to gain additional insight given the proteomic complexity of HDL. Spectral counting was used as a semi-quantitative screen to identify proteins whose abundance changed due to rosuvastatin treatment, an experimental approach that has been validated in previous studies (Gordon et al., *J Proteome Res* 9: 5239-5249, 2010; Gordon et al., *Diabetes* 62: 2958-2967, 2013). As additional validation of the spectral counting approach, we also determined the correlation between spectral counts for apolipoprotein B and LDL-p. The stoichiometry on LDL is one molecule of apoB per particle so a linear relationship would be expected between a quantitative measure of apoB and LDL particle number, which was observed in FIG. 3 (R=0.884, p<0.0001).

Figure 4A:
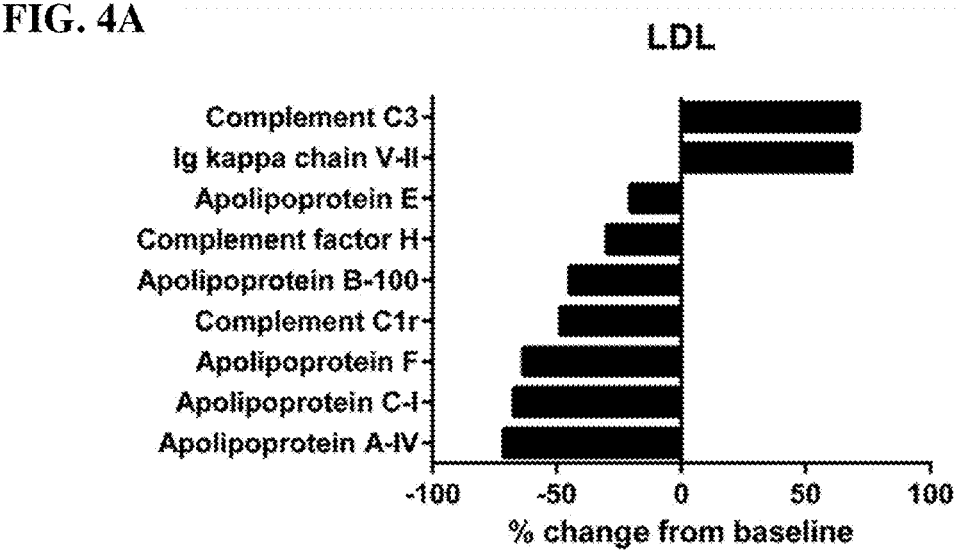
FIG. 4A-4B. Rosuvastatin alters the lipoprotein proteome. Statistically significant changes to the LDL (FIG. 4A) and HDL (FIG. 4B) proteomes resulting from rosuvastatin treatment are displayed as percent change compared to baseline. HDL-L=large HDL; HDL-S=small HDL; PGRP-L=N-acetylmuramoyl-L-alanine amidase. Statistical comparisons were made using student's T test. All displayed data are p<0.05.
Figure 4B:
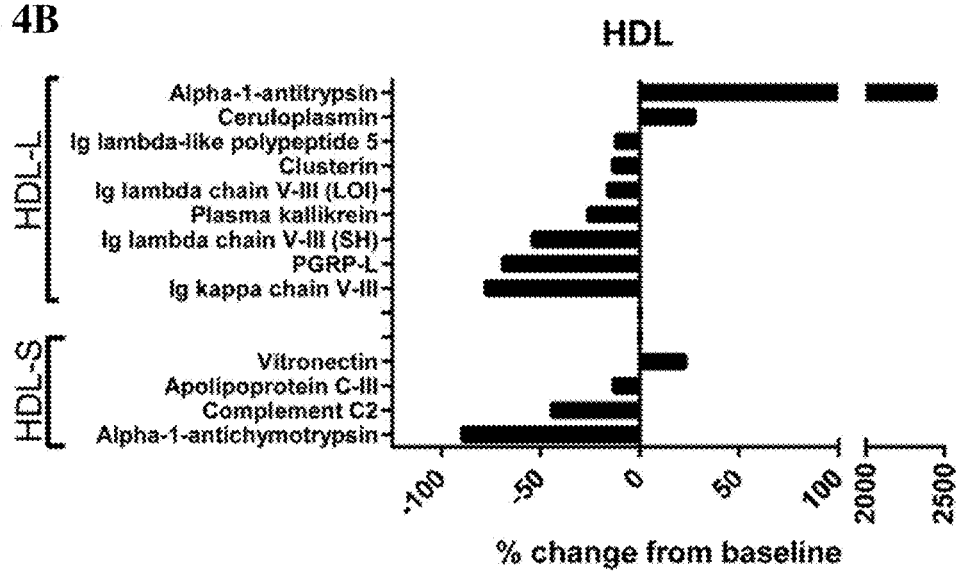

A total of 154 proteins were identified by MS analysis of all samples. The large number of identified proteins and the relatively small sample size of this study resulted in few statistically significant results after correction for multiple comparisons; however, because the objective of this study was strictly focused on screening to identify candidates for hypothesis driven studies, statistical comparisons between spectral counts from baseline and rosuvastatin treated samples were performed without correction for multiple comparisons. In the LDL fraction, nine proteins were found to display changes in abundance by spectral counting as a result of the rosuvastatin treatment (FIG. 4A). The majority of these were decreases, indicating reductions in total protein mass of LDL from the treatment. Additionally, the magnitude of these reductions in spectral counts ranged from −20 to −71%, which is similar to the degree of LDL particle number lowering achieved in this study and suggests that these results are largely a result of the LDL lowering effect of the rosuvastatin. It is interesting, however, that complement C3 (+71%) and Ig kappa chain V-II (+68%) demonstrated increased spectral counts in the LDL fraction, despite the significant reduction in LDL particle number and apoB. This relationship has not been previously described nor is the functional importance of these changes known.

Although rosuvastatin had minimal effect on HDL lipids and caused only a small increase in HDL particle number, several changes were observed in the HDL proteome (FIG. 4A). Most notably, on the large HDL, there was a marked elevation in alpha-1-antitrypsin (A1AT) spectral counts (+2438%). In addition, ceruloplasmin also showed an increase in spectral counts (+27%). Reductions in spectral counts were also observed for the following proteins: several immunoglobulin chains (variable), N-acetylmuramoyl-L-alanine amidase (−69%), kallikrein (−26%), clusterin (−13%) and Ig lambda like polypeptide 5 (−12%). Overall, there were fewer changes in spectral counts in the small HDL fraction: (alpha-1-antichymotrypsin (−89%), complement C2 (−44%), apolipoprotein C-III (−13%) and vitronectin (+23%).

Quantitation of Alpha-1-Antitrypsin Raising Effect of Rosuvastatin.

Of the numerous changes in the HDL proteome following rosuvastatin treatment, we focused on A1AT because it showed the largest change and the function of A1AT is relatively well understood. In fact, the magnitude of the increase of HDL bound A1AT in this study was much greater than changes found in previous studies that examined the effect of various diseases or therapy on lipoprotein proteome (Vaisar et al., *J Clin Invest* 117: 746-756, 2007; Gordon et al., *Diabetes* 62: 2958-2967, 2013; Green et al., *Circulation* 118: 1259-1267, 200). Additionally, A1AT has been shown to be involved in cardiovascular disease by modulating various inflammatory processes (Gilutz et al., *Br Heart J* 49: 26-29, 1983; Duckers et al., *Respir Res* 11: 173, 2010).

Figure 5A:
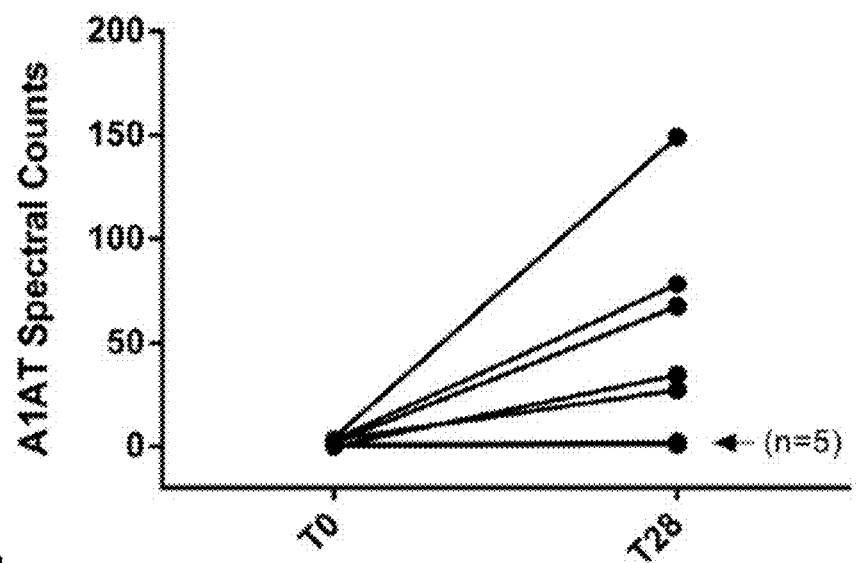
FIG. 5A-5C. Quantitative measurement of alpha-1-antitrypsin on HDL and in plasma.
Figure 5B:
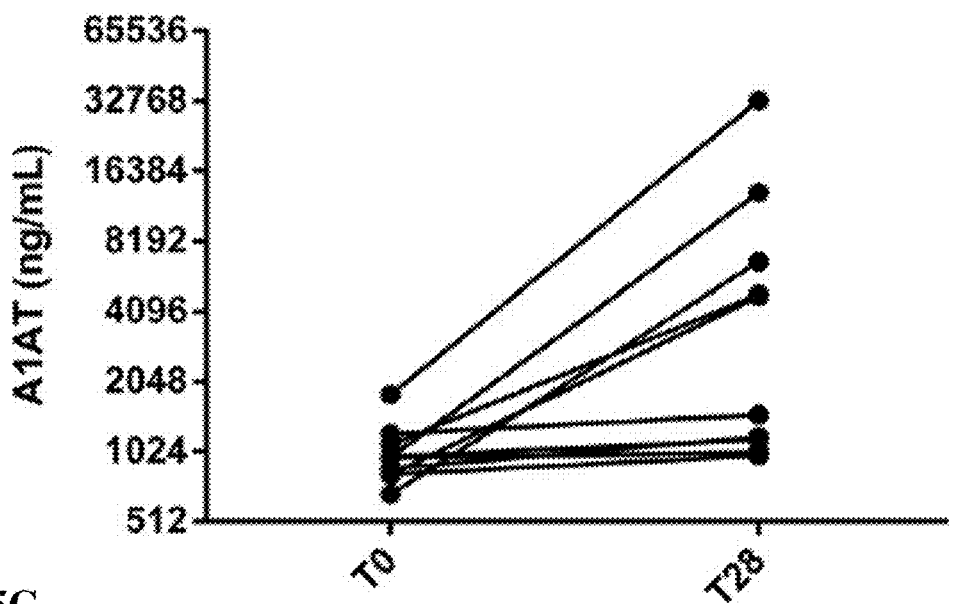

To more quantitatively evaluate the change in A1AT levels observed in the MS data, we performed ELISA assays to measure A1AT in the large HDL fractions from all subjects. There was a distinct segregation of the subjects into two groups: high responders that showed a marked elevation of A1AT (range: 5-18 fold) in their large HDL fraction in response to rosuvastatin therapy and low-responders that only showed a modest increase in A1AT levels (range: 6-36%) after therapy. This segregation was consistent with our MS data (FIGS. 5A and 5B) and did not appear to be associated with baseline plasma lipid measures or C-reactive protein (CRP).

Figure 5C:
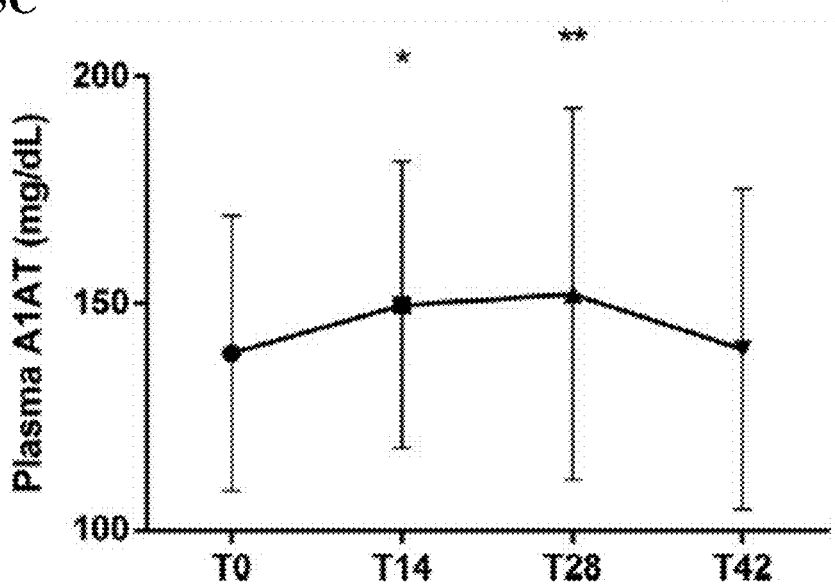

In addition to measuring the A1AT content of large HDL, we also measured total A1AT in plasma. There was a clear trend of increasing plasma A1AT while on treatment and a return to baseline after a two week treatment washout, this effect was relatively small, approximately 10% (FIG. 5c). The change in total A1AT did not appear to correlate with the change observed in A1AT on large HDL after rosuvastatin therapy. Based on the content of AAT on HDL-L and in plasma, we estimate that on average approximately 4.54±1.73% of total A1AT was bound to HDL after rosuvastatin therapy, whereas only 0.84±0.037% was bound at baseline before treatment. We calculated an A1AT:HDL-particle ratio (mol:mol) of about 1:100 at baseline and 1:25 after rosuvastatin treatment.

A1AT Binds to Lipids with its Reactive Center Loop.

Figure 6A:
FIG. 6A-6B. Structural prediction of lipid binding by alpha-1-antitrypsin.
Figure 6B:
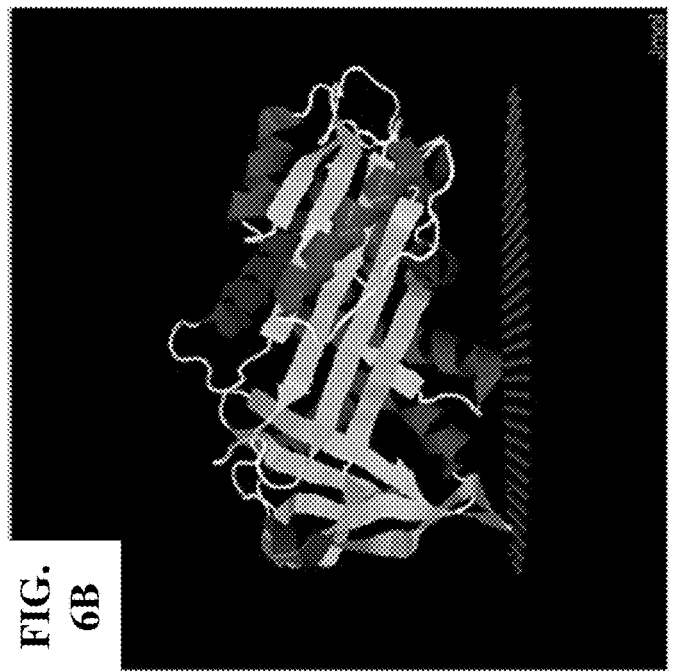

To examine the potential structural basis for the interaction of AAT with lipoproteins, we used modeling software that calculated the optimum thermodynamic orientation for a protein to interact with a phospholipid bilayer, using their 3D structures. The crystal structure for A1AT was downloaded from Protein Data Bank (available on the World Wide Web at resb.org; structure ID: 3NE4) and used as input for the lipid binding prediction in the position of proteins in membranes server (available online at opm.phar.umich.edu/) (Lomize et al., *Nucleic Acids Res* 40: D370-376, 2012). From this analysis, an exposed random coil region of the A1AT protein was predicted to insert into the outer leaflet of a phospholipid bilayer (FIG. 6A). This region of AAT corresponds to the reactive center loop (RCL) of A1AT, which contains the active site responsible for the ability of this protein to inhibit proteolytic activity, and is relatively hydrophobic. In this binding model, two methionine residues critical to the function of AAT (Met351 & Met358) are predicted to be buried in the lipid surface. These methionine residues are highly susceptible to oxidation to methionine sulfoxide. Previous studies have shown that oxidative modification of either of these residues will result in the loss of anti-elastase activity (Taggart et al., *J Biol Chem* 275: 27258-27265, 2000). If the RCL region of the protein is removed from the protein structure (A1ATΔ346, FIG. 6B), the protein is predicted to have markedly reduced affinity for the lipid surface, as indicated by decreased calculated insertion depth and decreased $\Delta G_{transfer}$ energy.

Figure 7A:
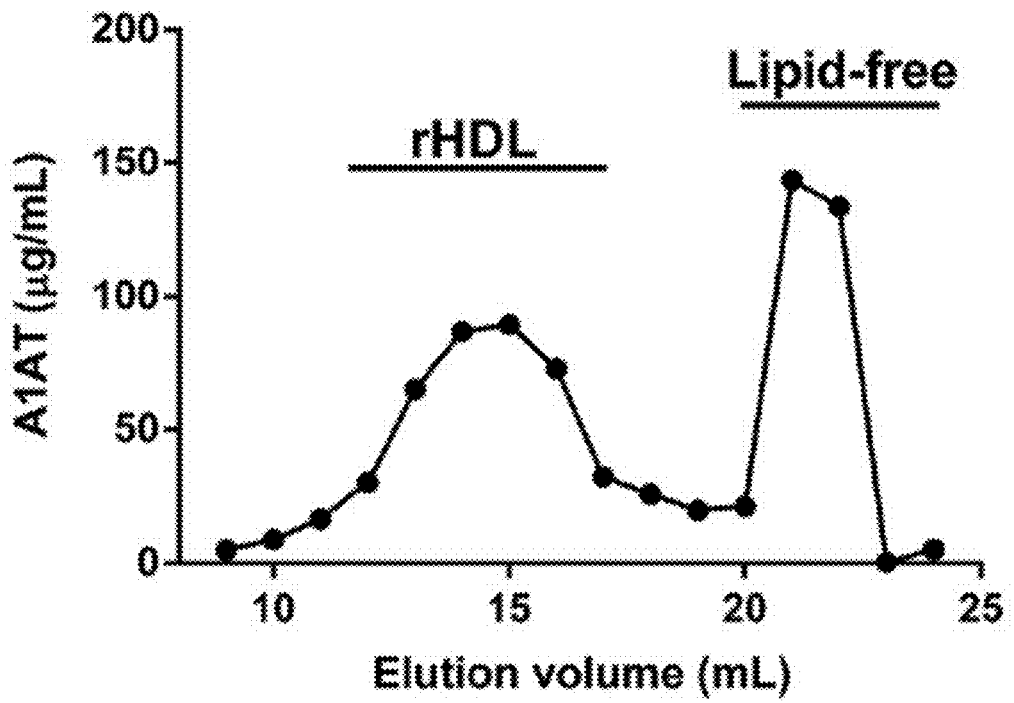
FIG. 7A-7B. Alpha-1-antitrypsin has reduced anti-elastase activity when bound to reconstituted HDL. Reconstituted HDL (rHDL) were prepared from apoA-I and phospholipids by cholate dialysis and then co-incubated with alpha-1-antitrypsin (A1AT) to generate A1AT enriched rHDL.

Based on this lipid binding model for A1AT, we hypothesized that the burying of the RCL domain into the lipids surface of HDL would affect its capacity to inhibit elastolytic activity. To test this, we made reconstituted HDL containing A1AT by cholate dialysis. As can be seen by the gel filtration profile, when A1AT was incubated with discoidal HDL, containing apoA-I and phospholipids, a significant fraction of A1AT associates with HDL (FIG. 7A). Similarly, and consistent with previous studies, when native HDL isolated from plasma was incubated with A1AT, it became enriched in A1AT (Moreno et al., *Am J Respir Cell Mol Biol* 51: 536-549, 2014).

Figure 7B:
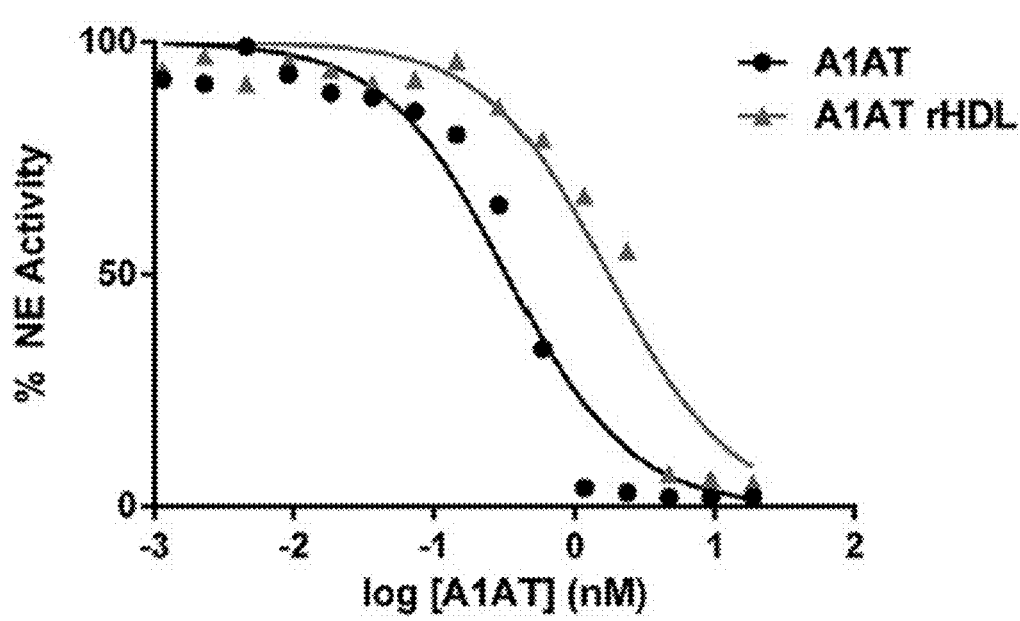

Next, we compared the ability of A1AT bound to HDL versus free A1AT to inhibit elastase activity. The HDL particle bound A1AT showed a 5-fold reduction in elastase inhibitor capacity (FIG. 7B), suggesting that the active site in the RCL is sterically blocked from interacting with elastase when bound to HDL. Overall, this data supports our model of lipid binding and suggests several possible functional implications of the interaction between A1AT and HDL, which we tested below.

HDL Binding Protects A1AT Anti-Elastase Activity from Inactivation by $H_2O_2$.

Figure 8:
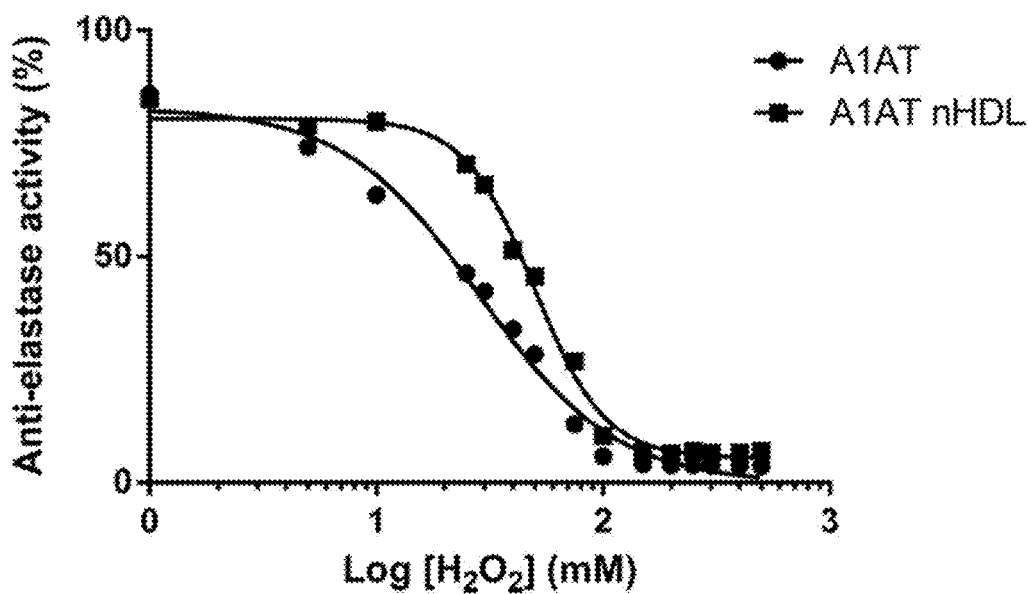
FIG. 8. Binding to HDL protects alpha-1-antitrypsin anti-elastase activity from oxidation by $H_2O_2$. HDL isolated from healthy human donors was co-incubated with alpha-1-antitrypsin (A1AT) to generate A1AT enriched nHDL. Lipid free A1AT and A1AT nHDL were exposed to varying concentrations of $H_2O_2$ for 30 minutes before measurement of anti-elastase activity by fluorometric assay. Nonlinear regression analysis was used for comparison of curve fits and found the two curves to be significantly different (p<0.0001).

In atherosclerotic plaque, activated neutrophils and macrophages create an oxidizing environment by generating reactive oxygen species, such as hydrogen peroxide ($H_2O_2$) (Nathan & Root, *J Exp Med* 146: 1648-1662, 1977; Rajagopalan et al., *J Clin Invest* 98: 2572-2579, 1996). Based on the binding model of A1AT to HDL, we predicted that submersion of the critical Met351 & Met358 residues, which are susceptible to $H_2O_2$ oxidation, in the lipid surface may confer protection of these residues in the RCL against oxidation and therefore promote the preservation of anti-elastase activity in an oxidizing environment. To test this hypothesis, we generated A1AT enriched native HDL (nHDL) by co-incubating A1AT with isolated human HDL and then removed unbound A1AT. Either free A1AT or A1AT-nHDL was exposed to $H_2O_2$ at various concentrations and remaining anti-elastase activity was measured. Nonlinear regression analysis of the dose response curves of anti-elastase activity versus [$H_2O_2$] indicated a shift in $IC_{50}$ (28.09 vs 46.42 mM $H_2O_2$ for A1AT and A1AT-HDL, respectively; p<0.0001), indicating that HDL bound A1AT was more resistant to inactivation by $H_2O_2$ (FIG. 8). This finding suggested that although binding of AAT to reconstituted HDL resulted in a reduction of A1AT activity, the interaction of A1AT with HDL may be beneficial in stabilizing its activity in a pro-oxidant environment, such as an atherosclerotic plaque.

Effects of A1AT Enriched HDL on Elastase Induced Macrophage Activation.

An early event in the initiation of atherosclerosis is the infiltration of circulating neutrophils and monocytes into the sub-endothelial space. Upon activation, neutrophils and macrophages in this environment produce oxygen radicals and also secrete neutrophil elastase, a proteolytic enzyme, which can cause degradation of the extracellular matrix and activation of proinflammatory signaling pathways in nearby cells via protease activated receptors. We used the J774 macrophage cell line to examine the proinflammatory response induced by elastase exposure and to determine the effect A1AT enriched HDL would have on this response.

Figure 9A:
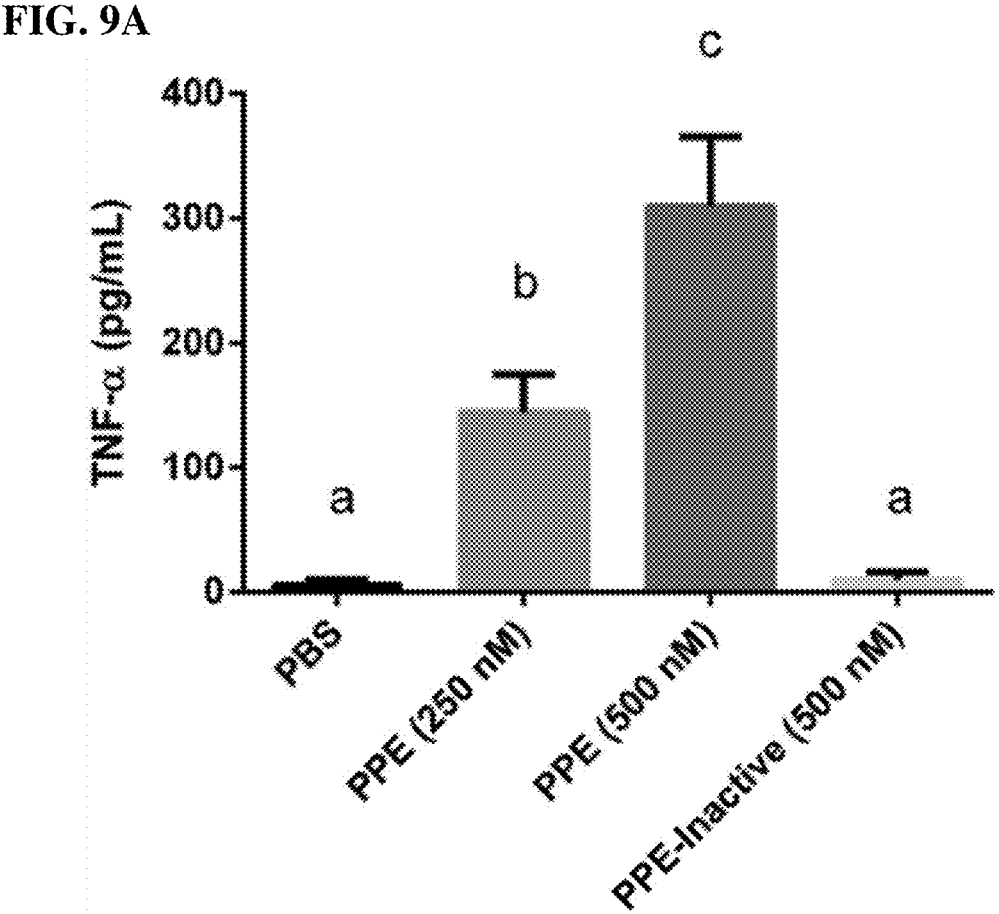
FIG. 9A-9E. Alpha-1-antitrypsin enriched HDL prevents elastase induced TNF-α production by macrophages.
Figure 9B:
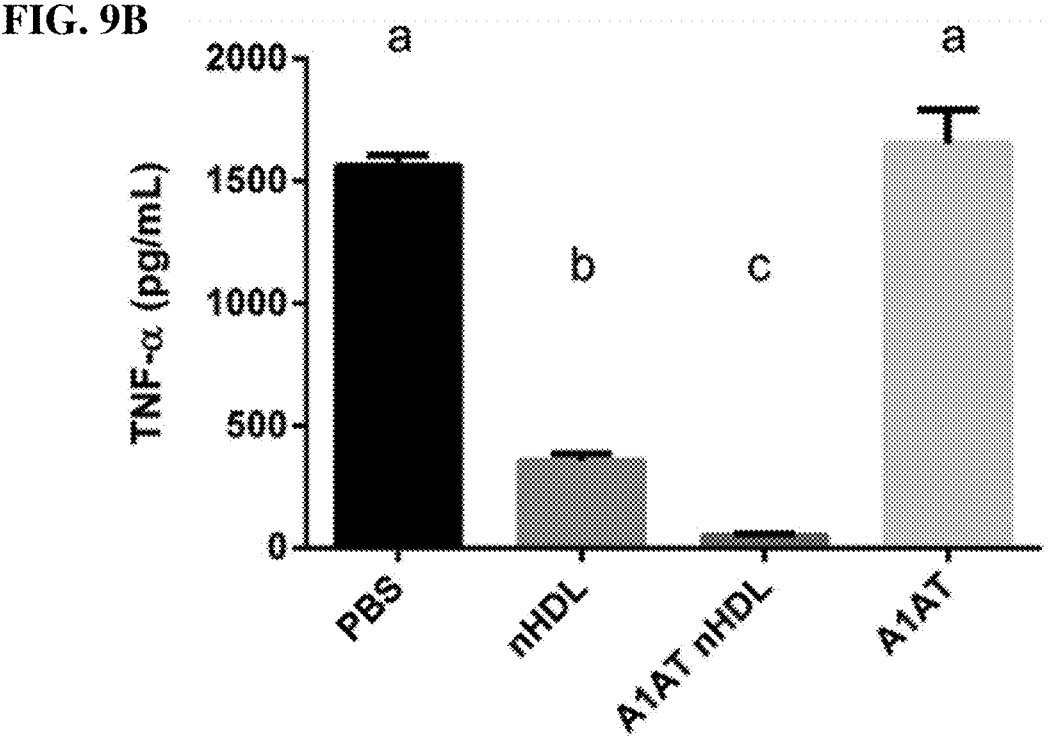

We first demonstrate that, in the J774 cell system, exposure to elastase induces a strong proinflammatory cytokine response, with increased TNF-α in the cell media in a dose-dependent manner and this effect is absent when treated with heat-inactivated elastase (FIG. 9A). Next, J774 cells were pre-incubated with PBS, native HDL (nHDL), A1AT enriched nHDL, or lipid-free A1AT for 1 hour prior to the addition of elastase to the culture media to allow for inactivation of A1AT. Upon elastase addition, cells pretreated with PBS displayed a robust production of TNF-α. Native HDL had a strong anti-inflammatory effect, significantly reducing TNF-α production by −77.2% compared to PBS pretreatment (FIG. 9B). This already impressive effect was further amplified and TNF-α production was almost completely suppressed (−97%) when cells were pretreated with HDL further enriched in A1AT. In contrast, pretreatment with lipid-free A1AT had no significant protection against elastase induced TNF-α production. The almost complete lack of effect with lipid-free A1AT was unexpected but suggests that in the lipid-free form, A1AT may be quickly degraded or inactivated when cultured with macrophages.

Figure 9C:
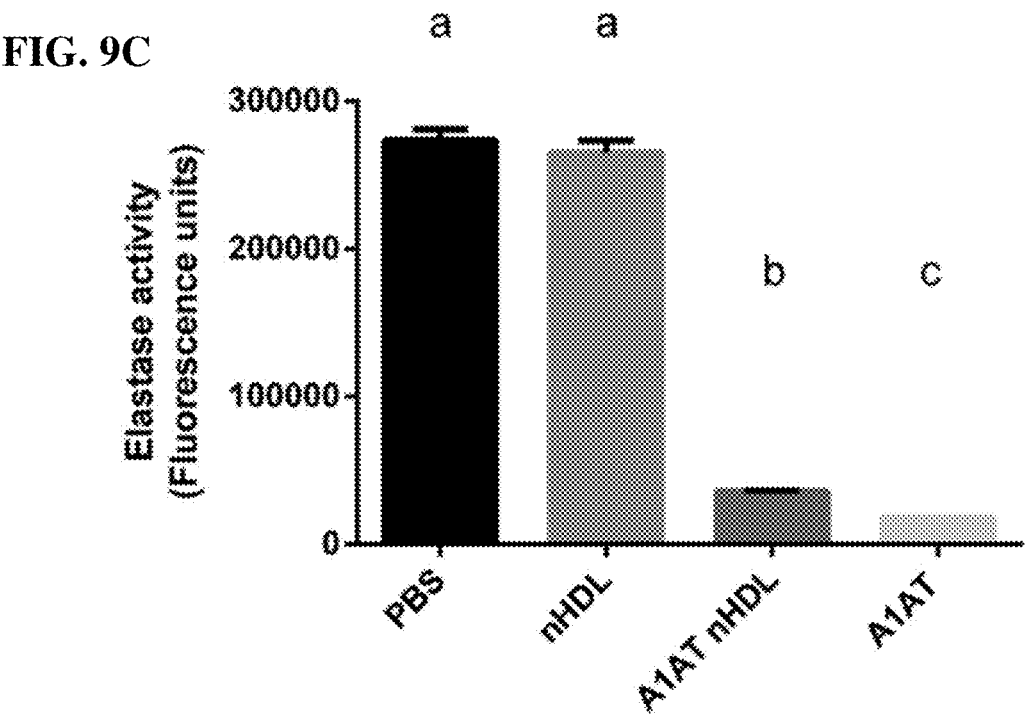
Figure 9D:
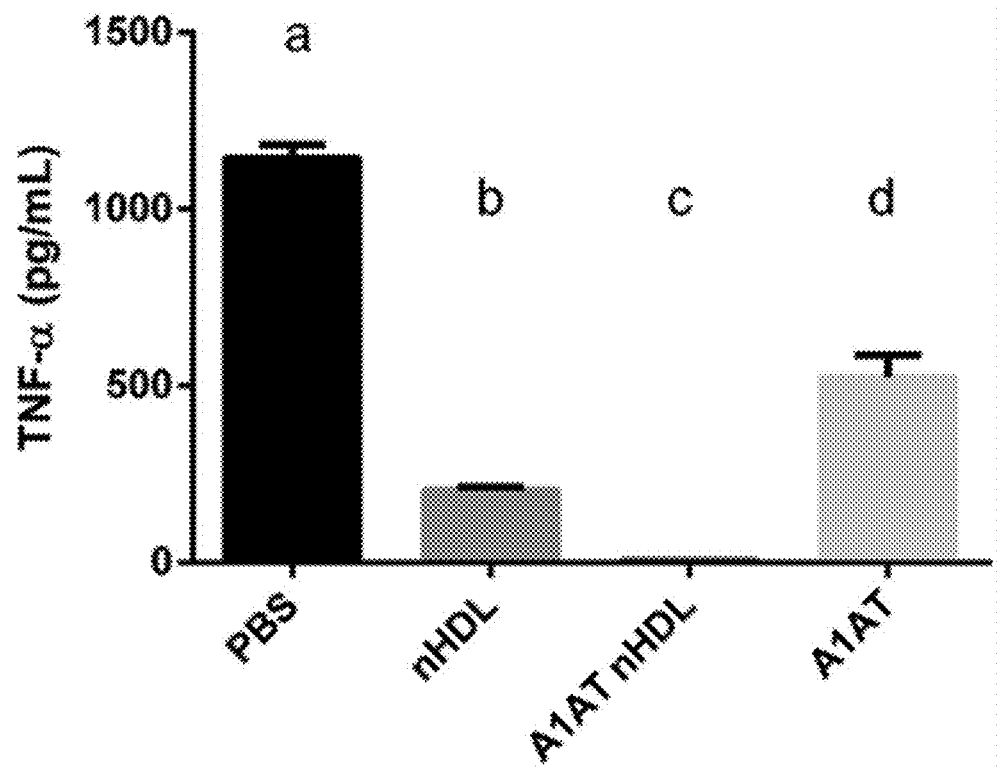

To determine if degradation was responsible for the loss of AAT activity, we performed western blot for A1AT on the cell culture media and found no evidence of proteolytic degradation of A1AT. This suggested to us that the loss of anti-protease activity in the lipid-free A1AT treatment may be due to another inactivating protein modification. We then performed elastase inhibition assays on each of the treatments in FIG. 9B, but in a cell-free system. The results of this experiment demonstrated that the PBS and nHDL treatments did not inhibit elastase activity, however, both A1AT HDL and lipid-free A1AT showed significant anti-elastase activity, indicating that the cell culture environment inactivated the lipid-free A1AT but did not affect the HDL bound A1AT (FIG. 9C). In further support of this model, when each of the treatments was pre-incubated with elastase prior to addition to the cells, free A1AT was then readily able to inhibit elastase induced TNF-α production (FIG. 9D).

Figure 9E:
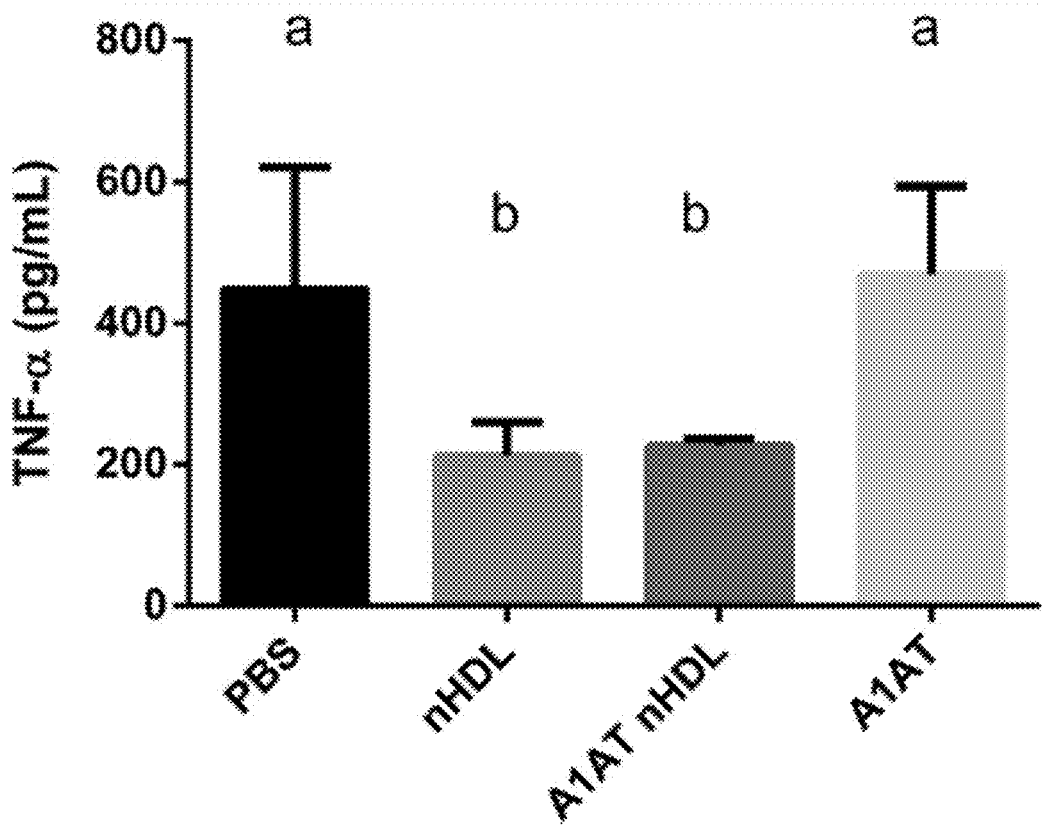

In another experiment, J774 cells were pretreated in the same manner as for FIG. 9B, except that the cell media was removed and the cells were washed prior to addition of fresh serum free media containing elastase. Under these conditions, the nHDL pretreatment still provided significant protection against elastase induced TNF-α production (FIG. 9E), indicating that the effect of native HDL is occurring via an intracellular or signaling pathway. However, the additional protection conferred by A1AT enrichment was lost, indicating that the mechanism of action for A1AT HDL is by direct inhibition of elastase in the culture media. Treatment with lipid-free A1AT still had no effect.

Overall, this data supports a mechanism whereby lipid-free A1AT is rapidly inactivated in macrophage culture media and is unable to inhibit elastase induced cytokine production by macrophage cells. However, when associated with HDL, A1AT retains its anti-elastase activity and efficiently inhibits elastase induced TNF-α production. Based on our lipid binding model, we predict that the preservative effect of HDL binding on A1AT activity may be a result of the interaction of the RCL with the lipid surface conferring protection in an oxidizing environment.

Discussion

In this Example, we report the impact of rosuvastatin treatment on the lipoprotein proteome in humans and found that several protein components of both LDL and HDL particles were affected by treatment. The majority of proteome effects on LDL were reductions in protein content, which likely reflect the overall reduction in LDL particle number associated with statin therapy. However, despite this reduction in particle number, there were two proteins that displayed increased abundance on LDL with statin treatment, namely complement C3 and Ig kappa chain V-II. We found no existing reports of direct functional relationships between these proteins and LDL, but their elevation on the background of dramatic LDL lowering may indicate the presence of a subpopulation of LDL that is either resistant to lowering by rosuvastatin or perhaps is generated as a consequence of the treatment. Whether or not these particles have any influence on lipoprotein metabolism or cardiovascular disease is an area of interest for future studies.

Although rosuvastatin treatment had little or no impact on HDL particle number, total HDL-C, or HDL lipid profile by FPLC, there were several major proteome changes observed. Among these was a dramatic 24-fold increase in A1AT spectral counts associated with large HDL, a protein change much greater than typically observed in other similar lipoprotein proteome studies. Because of this and the known function of A1AT, we chose to focus our attention on this protein change and to investigate its functional consequences. A1AT is an acute phase reactive plasma protein with a typical plasma concentration below 1.5 mg/mL. It belongs to the serine protease inhibitor (SERPIN) family of proteins of which there are 36 members in humans, 29 of which have anti-protease activity. A1AT is one of the most abundant SERPINs and is the primary physiological inhibitor of neutrophil elastase (NE) (Gettins, *Chem Rev* 102: 4751-4804, 2002). NE is produced by activated neutrophils and macrophages in atherosclerotic lesions where it degrades components of the extracellular matrix (i.e. elastin, collagen and fibronectin) (Weiss, *N Engl J Med* 320: 365-376, 1989; Dollery et al., *Circulation* 107: 2829-2836, 2003). Additionally, cholesterol loaded monocyte-derived macrophages, such as those found in atherosclerotic plaque, express elevated elastolytic activity (Rouis et al., *Arteriosclerosis* 10: 246-255, 1990). Besides degrading extracellular matrix, elastase can also stimulate production of pro-inflammatory cytokines and trigger pro-apoptotic signaling via protease activated receptors expressed on most cells (Shpacovitch et al., *J Leukoc Biol* 83: 1309-1322, 2008; Ramachandran et al., *J Biol Chem* 286: 24638-24648, 2011). These combined activities of elastase within the vessel wall likely contribute to atherosclerotic progression by promoting smooth muscle cell migration, endothelial cell apoptosis, and plaque instability (Garcia-Touchard et al., *Arterioscler Thromb Vasc Biol* 25: 1119-1127, 2005).

It has been demonstrated that HDL is actively transported across the vascular endothelium at the site of atherosclerotic plaque (Rohrer et al., *Circ Res* 104: 1142-1150, 2009), thus delivering HDL to this inflammatory, proteolytic environment. The fate of the protein cargo (such as non-apoA-I proteins) of HDL during this process has not yet been examined. However, it seems possible that the process of endothelial transcytosis of HDL may act as a mechanism for delivery of HDL's largely anti-inflammatory and anti-proteolytic cargo to a site of inflammatory distress. A1AT is fairly abundant in plasma, but it may need to reach the sub-endothelial space, where elastolytic proteases are produced by activated neutrophils and macrophages, to effectively inhibit protease mediated damage to the vessel wall. Although some small plasma proteins are capable of relatively rapid movement across the vascular endothelium, A1AT is similar to albumin in size and negative charge (pI≈4), and thus it is likely not capable of passive diffusion across the endothelium and may require active transport or a chaperone such as HDL.

Our findings expand significantly upon existing studies by first showing that A1AT binding to HDL is induced by rosuvastatin and by identifying a previously unidentified functional benefit of this association. Our data support a protective role for HDL, whereby the anti-elastase activity of AAT is preserved by interaction with HDL. Although our experiments with reconstituted HDL demonstrate that A1AT activity is reduced upon binding to HDL, a significant amount of anti-protease activity remains. Furthermore, it has recently been shown, in atherosclerotic plaques, that HDL particles eventually disassemble when they enter tissue and therefore may release free A1AT (Huang et al., *Nat Med* 20: 193-203, 2014). Based on our HDL binding model and our experiments with hydrogen peroxide, one possible mechanism for the preservation of A1AT activity when bound to HDL may be through shielding of oxidation susceptible methionine residues in the RCL, which when oxidized result in loss of A1AT activity. Other possible mechanisms may involve the protection of A1AT from degradation by other macrophage secreted proteases or HDL-directed cellular uptake and intracellular anti-proteolytic activity. Detailed mechanistic and structural investigations of these hypotheses are underway.

The association of A1AT with both LDL and HDL particles has been previously demonstrated by biochemical and proteomics based techniques. Binding to LDL occurs when A1AT has been oxidized and is inactivated (Mashiba et al., *Arterioscler Thromb Vasc Biol* 21: 1801-1808, 2001), but a change in the oxidation status of A1AT has not been previously implicated in altering its binding to HDL. There have been no reports on the mechanism of A1AT binding to HDL. It is currently unclear whether A1AT becomes associated with HDL during particle generation or is in a state of equilibrium, constantly exchanging to and from preformed HDL particles. Our data suggest only a minimal increase in total plasma A1AT while on rosuvastatin, an amount that is likely insufficient to account for a simple equilibrium driven shift onto HDL of the magnitude seen in this study. This suggests the possibility of increased de novo generation of A1AT containing HDL or that an additional plasma factor or a change in some physical property of HDL in response to statin treatment that may be responsible for the increased binding of A1AT. There have been only a limited number of functional investigations of A1AT on HDL. Studies by Meilhac et al first suggested a possible functional role for HDL bound A1AT in preventing apoptosis in vascular smooth muscle cells (Ortiz-Munoz et al., *FASEB J* 23: 3129-3139, 2009). A second study from the same group demonstrated a role for HDL in the selective transport of functional A1AT from the circulation to the lung, where it can prevent elastase induced morphological and functional damage in a rat model (Moreno et al., *Am J Respir Cell Mol Biol* 51: 536-549, 2014). These findings suggest a possible important role of A1AT bound HDL for the treatment of chronic obstructive pulmonary disease (COPD) or emphysema, where excessive elastolytic activity causes destruction of lung tissue and is often not adequately treated by replacement therapy with just A1AT (Abusriwil & Stockley, *Curr Opin Pulm Med* 12: 125-131, 2006).

Although the focus of this study is on A1AT, nine other members of the SERPIN family are consistently identified in proteomics studies of HDL (Davidson, The HDL Proteome Watch. available on-line at homepages.uc.edu/~davidswm/HDLproteome, 2015). The complete structural information is not available for all of these, but all of the well characterized SERPINs have structural organizations similar to that of A1AT with an exposed hydrophobic meta-stable RCL domain. It may be that many of these other SERPINs also bind HDL by a similar mechanism involving the RCL and similar functional relationships exist for this entire class of proteins.

Additional questions raised by the present report include whether the observed effects of rosuvastatin on the lipoprotein proteome are similar among all statins and whether this accounts for some of the known anti-inflammatory effect of statins (Antonopoulos et al., *Curr Pharm Des* 18: 1519-1530, 2012). One study of the HDL proteome, in patients receiving combination therapy of atorvastatin and niacin, found reduced apoE content in $HDL_3$, however no effect on A1AT was detected (Green et al., *Circulation* 118: 1259-1267, 2008). The absence of effect on A1AT in this study may be explained by several factors including the use of a different statin, addition of niacin treatment, or differences in HDL isolation (ultracentrifugation vs. gel filtration). Some of the anti-inflammatory effects of statins have been attributed to the ability to block the Rho signaling pathway (Martin et al., *J Clin Invest* 107: 1423-1432, 2001) but based on the results of this study their ability to also modulate A1AT levels on HDL may also be relevant. It is interesting to note that there have been several recent reports of statins (i.e. Simvastatin and atorvastatin) having protective effects on lung injury induced by elastase (Takahashi et al., *Am J Physiol Lung Cell Mol Physiol* 294: L882-890, 2008; Boiati et al., *Drug Res (Stuttg)*. 65(10):540-544, 2014) or by cigarette smoke (Lee et al., *Chest* 128: 574S, 2005; Wright et al., *Am J Respir Crit Care Med* 183: 50-58, 2011), which could potentially also be mediated by A1AT enriched HDL.

Studies of the lipoprotein proteome have gained increasing interest due to their clear potential for identifying functionally relevant lipoprotein subspecies. However, the list of lipoprotein associated proteins is growing faster than our understanding of the functional relevance of these complexes. New insight into the diagnostic or therapeutic implications of HDL sub-fractions with specific protein content will likely require direct experimental investigation as was done in this study. Although much still needs to be done in regard to the role of AAT interaction with HDL, to our knowledge this is the first report of a newly identified protein on HDL by LC-MS that has been shown to have a possible functional role in the pathogenesis of atherosclerosis.

Example 2: Alpha-1-Antitrypsin Protects High Density Lipoprotein from Functional Inactivation by Elastase High density lipoproteins (HDL) are complexes of lipid and protein with several known atheroprotective functions. These functions are driven by specific lipids and proteins contained on the HDL particle and include reverse cholesterol transport, suppression of inflammation, and modulation of endothelial function. These activities are most important within atherosclerotic plaque, a harsh environment where HDL interact with macrophage foam cells, activated neutrophils, and dysfunctional endothelial cells. Neutrophils and macrophages secrete proteases such as elastase, which damage structural components and soluble proteins and propagate inflammatory signaling. It has been suggested that, in plaque, HDL become damaged and dysfunctional.

We recently characterized a subspecies of HDL which carries the protein alpha-1-antitrypsin (A1AT), an abundant plasma serine protease inhibitor (Gordon et al., *Mol & Cell Proteomics* 14:3247-3257, 2015). In the current Example, we test the hypothesis that A1AT enriched HDL are protected from proteolytic damage and functional inactivation that is caused by elastase, the main protease inhibited by A1AT. Human HDL was isolated by ultracentrifugation, and was enriched with A1AT by co-incubation then unbound A1AT was removed. Treatment of native HDL with elastase resulted in significant proteolytic degradation of both apoA-I and apoA-II, visualized by Coomassie stained SDS-PAGE. Analysis of lipoprotein size by one dimensional native gel electrophoresis revealed that pre-beta HDL were completely destroyed by elastase. Compared to native HDL, A1AT enriched HDL samples were protected from protein and pre-beta particle degradation by elastase.

We next tested the effect of elastase treatment on HDL function. In native HDL, elastase had damaging effects on ABCA1 mediated cholesterol efflux (−32%; $p<0.0001$) and the ability to esterify free cholesterol (−14%; $p<0.02$). A1AT enriched HDL displayed no loss of functionality upon treatment with elastase. Both of these activities are required for HDL to perform what is thought to be its most important function, reverse cholesterol transport.

In conclusion, the data presented here indicate that HDL particles which contain A1AT may represent a functionally important species of HDL which have an advantage in the protease-rich plaque environment.

Methods:

Isolation of human HDL and enrichment with alpha-1-antitrypsin. HDL was isolated from human plasma by density gradient ultracentrifugation (1.063-1.21 g/mL). Isolated HDL was enriched with full length A1AT protein (Sigma, purified from human plasma) by co-incubation overnight at 37° C. HDL was re-purified by size-exclusion chromatography to remove unbound A1AT.

Elastase treatment of HDL. Native HDL or A1AT enriched HDL were treated with various doses of elastase (0, 0.25, or 0.5 units) for 60 min. at 37° C. To examine the effect of elastase treatment on individual HDL proteins, samples were analyzed by SDS-PAGE and Coomassie blue staining. Additionally, samples treated at the highest dose of elastase (0.5 units) were analyzed by one dimensional native gel electrophoresis to examine the effect of elastase treatment on intact lipoprotein particles. The gel was transferred to PVDF membrane and western blotting was used to detect apoA-I protein. The approach allows for detection of α and pre-β lipoprotein particles.

Functional Analysis of Elastase Treated HDL.

Cholesterol Efflux. BHK cell lines stably transfected with either MOCK (control), ABCA1, or ABCG1 cholesterol transporters were used to measure cholesterol efflux to elastase treated HDL. Briefly, cells were loaded with radioactive 3H labeled free-cholesterol by co-incubation and unincorporated cholesterol was removed by washing. Samples were added to the cell culture media and incubated for 6 hours. After incubation, the transfer of radiolabeled cholesterol from the cells to media was measured by scintillation counting and the amount of cholesterol efflux was calculated.

Activation of Lecithin Cholesterol Acyltransferase (LCAT). The assay for LCAT activity involves incorporation of $^3$H-labeled free cholesterol into isolated human HDL followed by incubation at 37° C. to activate endogenous LCAT. After incubation, lipids were extracted and thin layer chromatography was used to separate free cholesterol from esterified cholesterol (the product of LCAT activity). The spots for free cholesterol and esterified cholesterol were collected and radioactivity associated with each measured to determine their ratio, which indicates the level of LCAT activity.

Paraoxonase (PON1) activity. HDL associated PON1 activity (arylesterase) was measured using a commercially available kit (Zeptometrix) that measures the cleavage of phenyl acetate to produce phenol. The activity was measured by monitoring light absorbance at 270 nm.

Figure 10A:
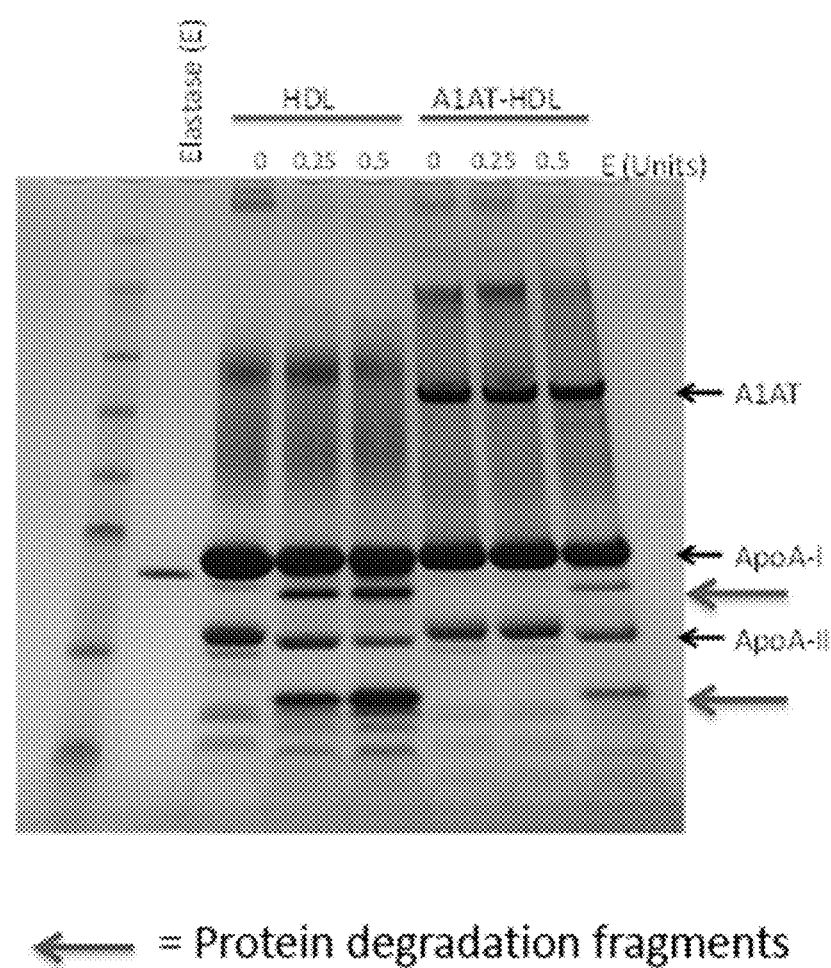
FIG. 10A-10B. Elastase treatment of HDL. Enrichment of HDL with A1AT protects HDL proteins (apoA-I and apoA-II) from degradation by elastase, SDS-PAGE with Coomassie blue stain for total protein (FIG. 10A). Additionally, elastase treatment results in degradation of pre-beta HDL and this is also protected by A1AT, one-dimensional native gel electrophoresis with western blot for apoA-I (FIG. 10B).
Figure 10B:
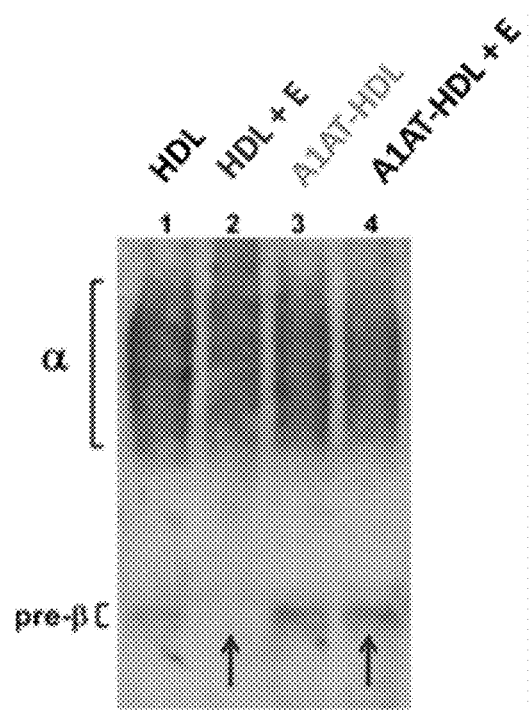

Results:

Elastase treatment of HDL. FIG. 10 shows that enrichment of HDL with A1AT protects HDL proteins (apoA-I and apoA-II) from degradation by elastase (FIG. 10A). Additionally, elastase treatment results in degradation of pre-beta HDL and this is also protected by A1AT (FIG. 10B). Pre-beta HDL is an important subpopulation of HDL which functions to perform cholesterol efflux from cells via the ABCA1 transporter. This function is believed to be one of the most important protective functions of HDL.

Figure 11A:
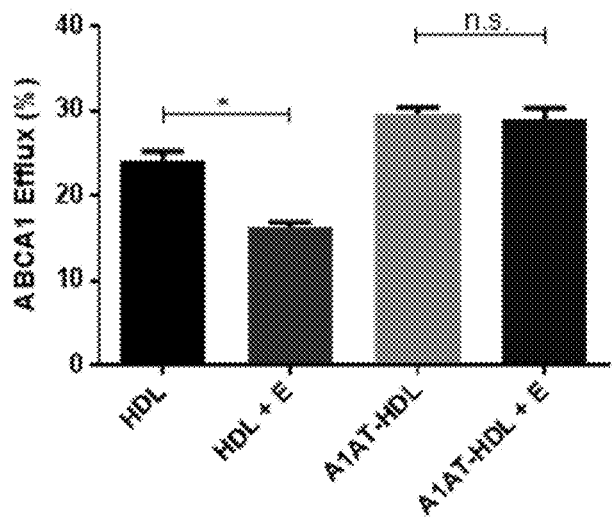
FIG. 11A-11C. Functional analyses of elastase treated HDL. The activity of three common HDL functions was measured in native HDL or A1AT-HDL with or without treatment with elastase. For native HDL, elastase treatment resulted in reduced cholesterol efflux (FIG. 11A), PON1 activity (FIG. 11B), and LCAT activity (FIG. 11C). A1AT-HDL was protected from elastase mediated reductions of all of these functions.
Figure 11B:
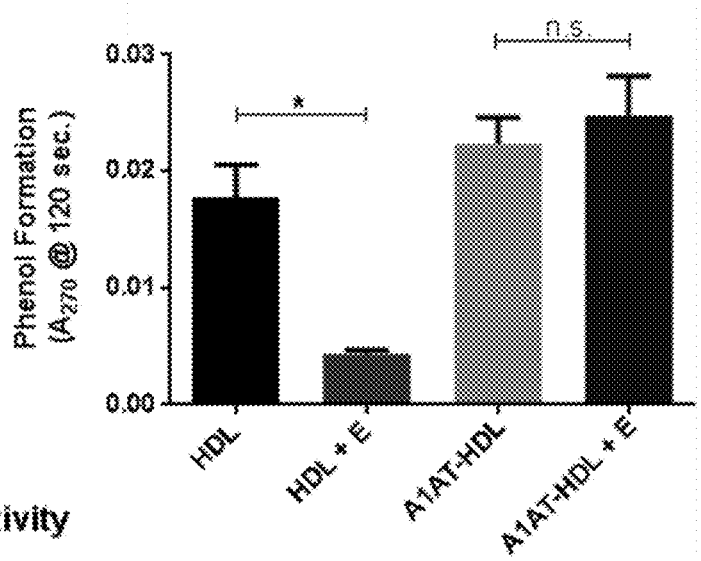
Figure 11C:
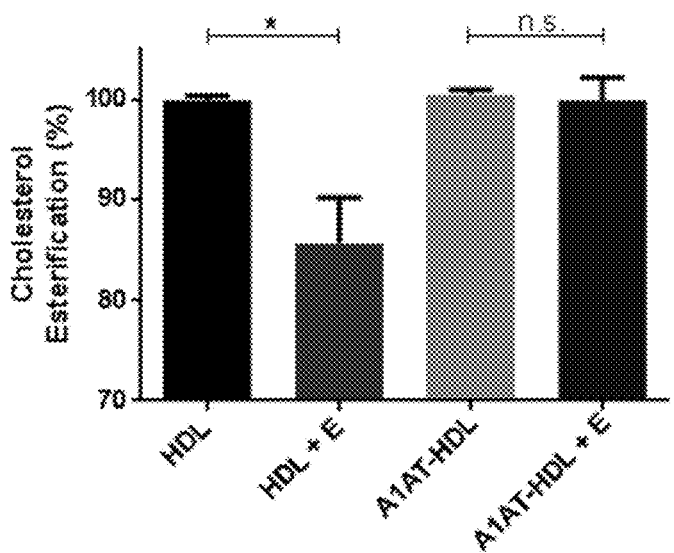
Figure 12:
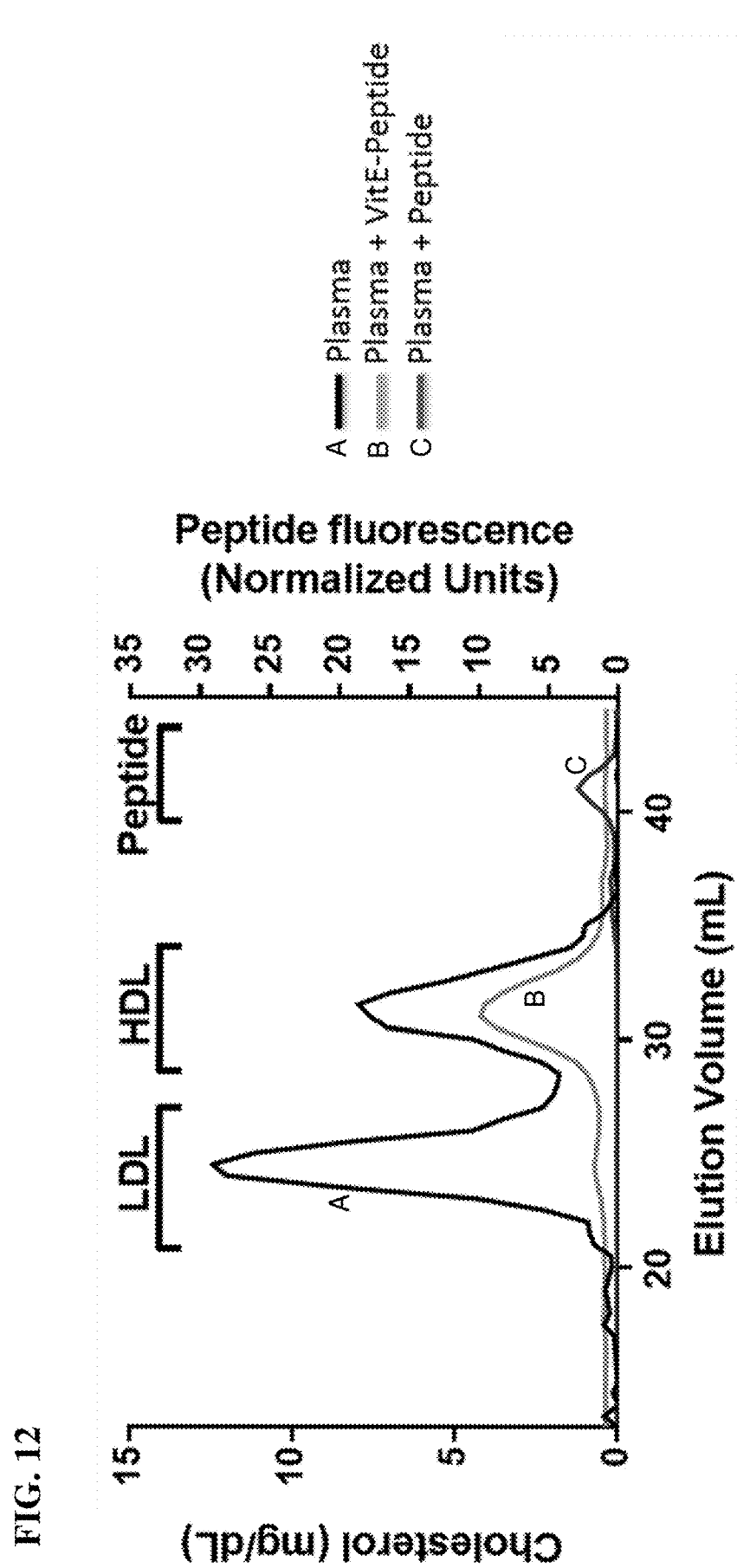
FIG. 12 is a graph showing that peptides conjugated to vitamin E bind HDL in plasma. The black line shows the FPLC elution profile of cholesterol indicating the distribution pattern of plasma lipoproteins in collected fractions. The red and green lines represent the elution profile of a fluorescent peptide without (red) or with (green) VitE conjugation. This data indicates that, when conjugated to Vitamin E, small peptides preferentially bind to HDL in human plasma.

Functional analysis of elastase treated HDL. We tested the effect of elastase treatment on three different HDL functions: cholesterol efflux (FIG. 11A), PON1 Activation (FIG. 11B) and LCAT activity (FIG. 11C). In each case, elastase treatment of HDL resulted in a reduction of activity (first and second bars in each panel). However, A1AT enrichment protected HDL from elastase treatment (third and fourth bars in each panel). A1AT enriched HDL exist naturally in the circulation in humans but represent only about 1% of the total HDL population.

Additionally, Example 1 indicates that statin treatment may increase the amount of A1AT containing HDL. Overall, these data support the concept that A1AT enriched HDL are protected from functional inactivation which, evidence suggests, can happen within atherosclerotic plaques, where HDL function is needed most.

Example 3: HDL Targeting Protease Inhibitor

This example describes production and characterization of a representative lipoprotein targeting protease inhibitor fusion molecule, referred to as E-AAPV peptide (a.k.a. vitE-PEG-AAPV; SEQ ID NO: 5) (vitamin E linked to the A1AT linear peptide AAPV (SEQ ID NO: 1) via a PEG$_{2000}$ linker). This peptide molecule (shown pictorially in FIG. 13A) is a mimetic of A1AT and is designed to bind to HDL (shown pictorially in FIG. 13B) and to inhibit elastase activity similarly to full length A1AT.

Construction of VitE-PEG$_{2000}$-AAPV peptide. AAPV-CMK (2.5 mg; SEQ ID NO: 3) was dissolved in 0.5 ml of 0.1 M Na—Bo buffer, pH 8.9. While stirring at room temperature, solid VitE-PEG-NHS (5-fold molar excess over AAPV-CMK) was added stepwise into the vial. The pH was monitored and adjusted to maintain pH 8.9 as needed, by addition of 0.5 M NaOH. See FIG. 14 for an overview of the reaction.

Figure 15:
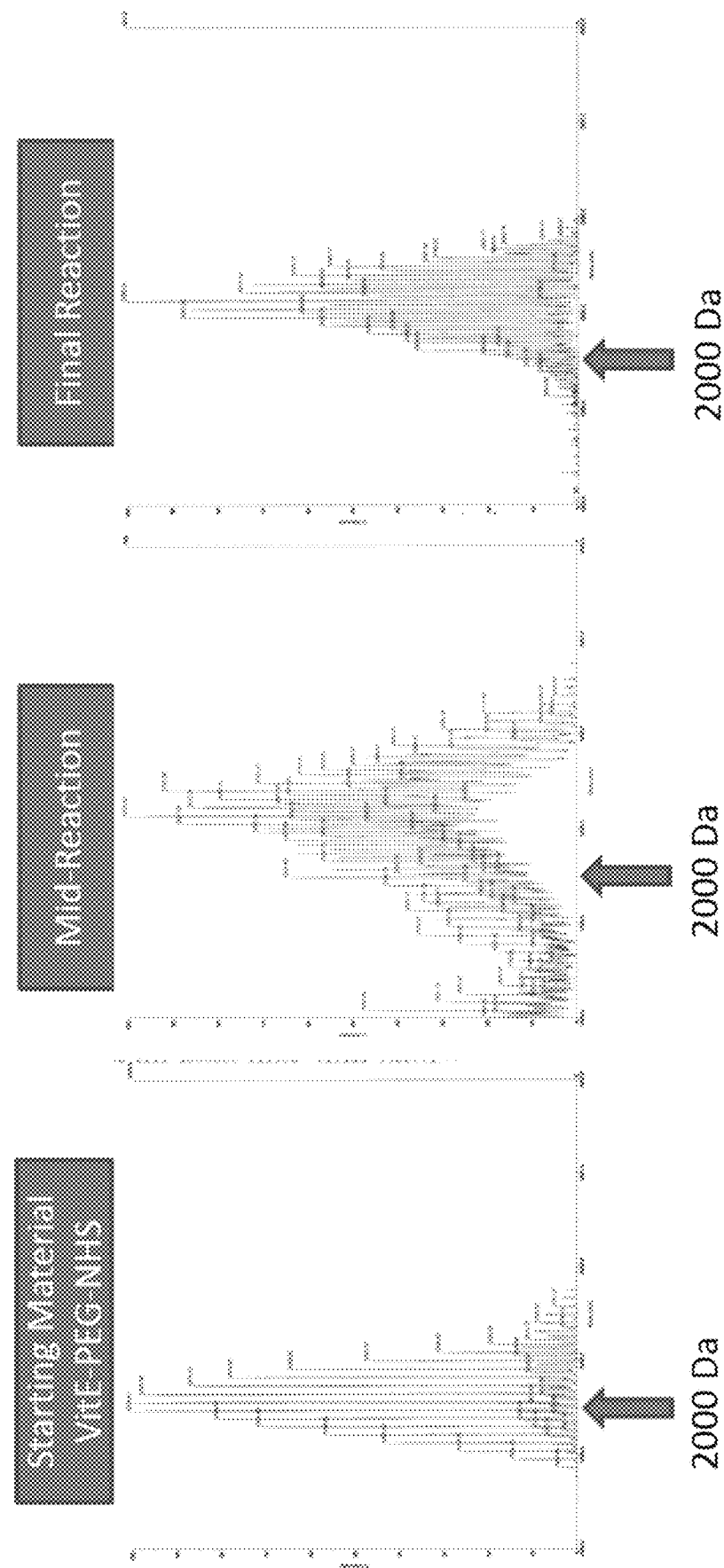
FIG. 15 is a series of three mass spectrometer traces, showing the change of molecular weight of the compound during reaction between VitE-PEG-NHS with the elastase inhibitor peptide, AAPV-CH$_2$Cl (SEQ ID NO: 2).

Assessment of peptide production reaction. Reaction progress was monitored by MALDI mass spectrometry of ZipTip desalted samples at various points during the reaction (FIG. 15). The PEG linker produces a mass envelope with an average mass of 2000 daltons. The shift in the mass envelope to an average mass of about 2300 daltons (FIG. 15, third panel) is consistent with conjugation of the AAPV-CMK peptide. Additionally, reaction completion was confirmed using ninhydrin reaction to indicate that all available amines (peptide N-terminus) had been conjugated.

Figure 16:
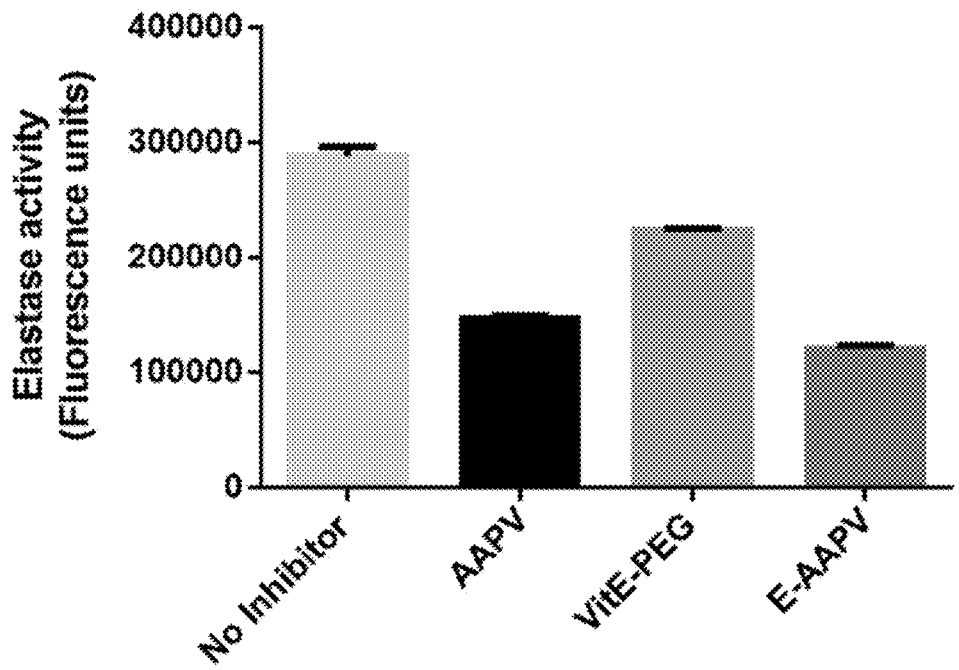
FIG. 16 is a graph showing elastase inhibitor activity of the reactants AAPV (SEQ ID NO: 1) and VitE-PEG and the product fusion peptide, E-AAPV (VitE-PEG$_{2000}$-AAPV; SEQ ID NO: 5). This data shows that VitE-PEG molecule alone does not convey elastase inhibition and that Vitamin E conjugation to the AAPV (SEQ ID NO: 1) peptide does not affect elastase inhibition activity.

Elastase Inhibitor Assay. Elastase inhibitor activity was evaluated using the commercially available EnzChek Elastase Assay Kit (Molecular Probes, Cat. #E-12056) and manufacturer suggested protocols. FIG. 16 shows elastase inhibitor activity of the reactants AAPV (SEQ ID NO: 1) and VitE-PEG and the product fusion peptide, E-AAPV (VitE-PEG$_{2000}$-AAPV; SEQ ID NO: 5). This data shows that VitE-PEG molecule alone does not convey elastase inhibition and that Vitamin E conjugation to the AAPV (SEQ ID NO: 1) peptide does not affect elastase inhibition activity.

E-AAPV peptide binds HDL and confers elastase inhibitor activity. The reaction product (E-AAPV; SEQ ID NO: 5) was coincubated with purified human HDL for 30 minutes at 37° C. followed by repurification of HDL by size-exclusion chromatography to remove unbound E-AAPV (SEQ ID NO: 5) peptide. The repurified HDL was then tested for elastase inhibitor activity using the assay described above.

Figure 17:
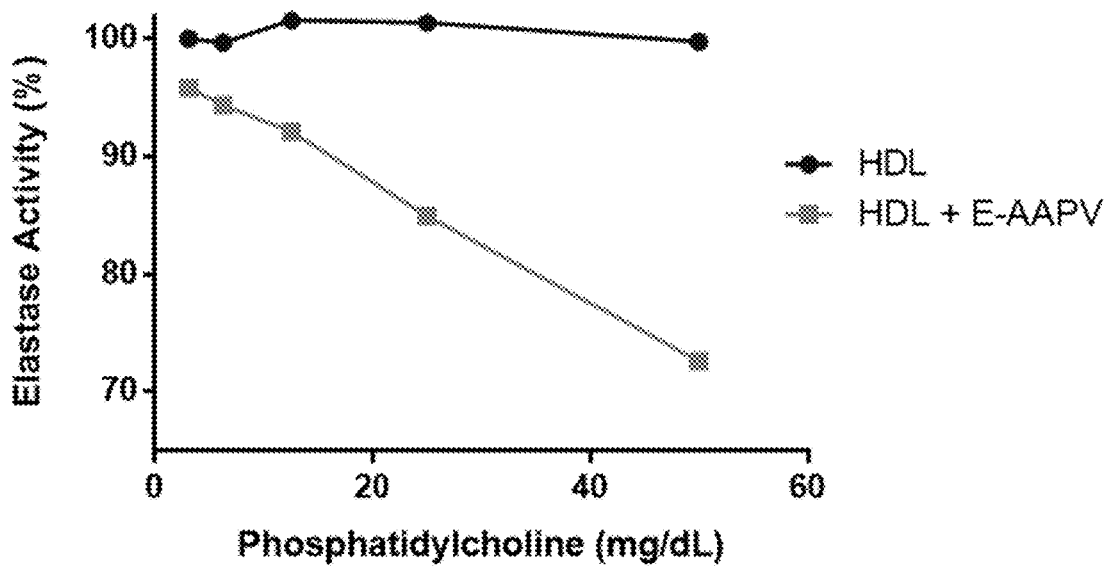
FIG. 17 is a graph showing that the E-AAPV (SEQ ID NO: 5) peptide binds HDL and confers dose-dependent elastase inhibitor activity. Isolated Human HDL was co-incubated with the E-AAPV (SEQ ID NO: 5) peptide for 30 minutes at 37° C. and then HDL was reisolated by FPLC to remove unbound E-AAPV (SEQ ID NO: 5). The HDL was then tested for elastase inhibition activity and compared to control HDL which was coincubated with PBS (no peptide) and repurified. Sampes were matched based on phospholipid content.

E-AAPV (SEQ ID NO: 5)-loaded HDL was compared to the same HDL that was coincubated with buffer only (No peptide). The HDL and HDL+E-AAPV (SEQ ID NO: 5) were normalized based on phospholipid content, determined by colorimetric assay, prior to measurement of elastase activity. FIG. 17 shows that the E-AAPV (SEQ ID NO: 5) peptide binds HDL and confers dose-dependent elastase inhibitor activity.

Discussion

Described above is the design and production of a lipoprotein targeting protease inhibitor peptide with potential therapeutic application, for instance, in patients with alpha-1-antitrypsin deficiency. This design is the result of the conjugation of two readily available components using amine reactive chemistry (N-hydroxysuccinimide) (FIG. 14) to generate the final product. We have demonstrated that the VitE-PEG-AAPV peptide retains elastase inhibitor activity and that this activity will associate with Human HDL after a brief co-incubation.

Example 4: Method of Treating A1AT Deficiency in a Subject

According to the teachings herein, one or more of the disclosed lipoprotein targeting protease inhibitor peptide comprising an elastase-inhibiting portion can be used to overcome, treat or inhibit A1AT deficiency and related symptoms in a subject. A method of overcome, treat or inhibit A1AT deficiency and related symptoms in a subject includes administering to the subject a therapeutically effective amount of a pharmaceutical composition including one or more of the peptides disclosed herein. In one example, a therapeutically effective amount of the pharmaceutical composition is provided by injecting intravenously 30 mg/kg of one or more of the disclosed peptides once a week. In certain representative examples, a pharmaceutical composition includes one of the following peptides: VitE-AAPV (SEQ ID NO: 4); VitE-PEG-AAPV (SEQ ID NO: 5); VitE-PEG-AAPV-CMK (SEQ ID NO: 6); VitE-AAPV-CMK (SEQ ID NO: 7); VitE-PEG-KRCCPDTCGIKCL (SEQ ID NO: 8); VitE-PEG-KRMMPDTMGIKML (SEQ ID NO: 9); VitE-PEG-EEIIMD (SEQ ID NO: 10); VitE-PEG-hirudin; VitE-PEG-lepirudin; VitE-PEG-desirudin; SEQ ID NO: 13; or SEQ ID NO: 14.

In another particular example, a method of treating A1AT deficiency or a symptom associated therewith is disclosed in which a pharmaceutical composition includes a peptide selected from among VitE-AAPV (SEQ ID NO: 4); VitE-PEG-AAPV (SEQ ID NO: 5); VitE-PEG-AAPV-CMK (SEQ ID NO: 6); VitE-AAPV-CMK (SEQ ID NO: 7); VitE-PEG-KRCCPDTCGIKCL (SEQ ID NO: 8); VitE-PEG-KRMMPDTMGIKML (SEQ ID NO: 9); VitE-PEG-EEIIMD (SEQ ID NO: 10); VitE-PEG-hirudin; VitE-PEG-lepirudin; VitE-PEG-desirudin; SEQ ID NO: 13; and SEQ ID NO: 14, and such composition is administered intraperitoneally at 150 mg/kg.

Example 5: Associating a Lipoprotein Targeting Protease Inhibitor Peptide with an Implant According to the teachings herein, one or more peptides comprising a lipoprotein targeting domain and a protease inhibitor domain, optionally further including therebetween a linker, can be placed in a suitable container, such as a tissue microcapsule implant, and placed within a subject to allow continuous, slow release of one or more of the disclosed peptides. Such peptides can either be provided in the free state or after complexation with lipid (e.g., in the form of a loaded or enriched nHDL or rHDL).

Example 6: Production of Additional Lipoprotein Targeting Protease Inhibitor Peptides This example describes the production of additional inhibitor peptides useful in the methods described herein.

Peptides were prepared (without C-terminal Valine-CMK) by solid phase synthesis using standard amino acids. After addition of the PEG, FITC (in the fluorescent labeled peptide), and VitE entities, valine chloromethylketone (CMK) was added to C-terminus by condensation reaction (Thompson, Biochemistry. 1973, PMID: 4734223). The following three peptides were produced:

Shortened PEG linker peptide:

VitE-(PEG)₂-Ala-Ala-Pro-Val-CMK
(SEQ ID NO: 6) (VitE-PEG$^{short}$-AAPV-CMK)

Non-Fluorescent Control peptide:

VitE-(PEG)₂-Lys-Gly-Ser-Gly-Ala-Ala-Pro-Val-CMK
(SEQ ID NO: 13) (VitE-PEG-KGSGAAPV-CMK)

Fluorescent Labeled peptide:

VitE-(PEG)₂-Lys-Gly-Ser-Gly-Ala-Ala-Pro-Val-CMK
|
FITC (SEQ ID NO: 14) (VitE-PEG-K$^{(F)}$GSGAAPV-CMK)

In the above formulae, (PEG)₂=Fmoc-NH-(PEG)₂-COOH (20 atoms) (Cat. #851031, from Novabiochem®; now EMD Millipore, Billerica, MA); FITC=Fmoc-K(FAM)-OH (from AnaSpec, Fremont, CA), which was selectively conjugated to the e group of Lys residue in fluorescent peptide; and VitE=Vitamin E.

This disclosure provides lipoprotein targeting protease inhibitor peptides, compositions comprising such peptides (including protease inhibitor enriched HDL), and methods of their use. The disclosure further provides A1AT-enriched HDL particles, and methods of making and using such particles. It will be apparent that the precise details of the compositions, preparations, and methods described may be varied or modified without departing from the spirit of the described invention. We claim all such modifications and variations that fall within the scope and spirit of the claims below.

We claim:

1. A method of treating alpha-1-antitrypsin (A1AT) deficiency or atherosclerosis, comprising administering to a subject in need thereof a composition comprising: Vitamin E (VitE)-PEG-AAPV (SEQ ID NO: 5); or VitE-PEG-AAPV-CMK (SEQ ID NO: 6); wherein the composition is administered to the subject by injection or infusion.

2. The method of claim 1, wherein the vitamin E (VitE) is selected from the group consisting of alpha-tocopherol, beta-tocopherol, gamma-tocopherol, delta-tocopherol, alpha-tocotrienol, beta-tocotrienol, gamma-tocotrienol, and delta-tocotrienol.

3. The method of claim 1, wherein the composition further comprises a pharmaceutically acceptable carrier.

4. The method of claim 3, wherein the pharmaceutically acceptable carrier is a lipid.

5. The method of claim 1, wherein the composition is administered in a liposome or reconstituted high density lipoprotein.

6. The method of claim 1, wherein the composition is administered to the subject intravenously, subcutaneously, intra-arterially, or intrapericardially.

7. A method of treating alpha-1-antitrypsin (A1AT) deficiency or atherosclerosis, comprising administering to a subject in need thereof a composition comprising:

```
                                    (SEQ ID NO: 5)
            VitE-PEG-AAPV; or (SEQ ID NO: 6)
            VitE-PEG-AAPV-CMK;
``` wherein the composition is incorporated in an implantable device.

8. The method of claim 7, wherein the implantable device is a stent.

* * * * *

SEQUENCE LISTING

```
<160> NUMBER OF SEQ ID NOS: 15

<210> SEQ ID NO 1
<211> LENGTH: 4
<212> TYPE: PRT
<213> ORGANISM: artificial sequence
<220> FEATURE:
<223> OTHER INFORMATION: synthetic peptide

<400> SEQUENCE: 1

Ala Ala Pro Val
1

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: modified with CH2Cl

<400> SEQUENCE: 2

Ala Ala Pro Val
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: mod_res
<222> LOCATION: (4)..(4)
<223> OTHER INFORMATION: modified with CMK

<400> SEQUENCE: 3

Ala Ala Pro Val
1

<210> SEQ ID NO 4
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: mod_res
```

```
<222> LOCATION: (1)..(1)
<223> OTHER INFORMATION: Modified with vitamin E (alpha tocopherol)

<400> SEQUENCE: 4

Ala Ala Pro Val
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: mod_res
<222> LOCATION: (1)..(1)
<223> OTHER INFORMATION: Modified with poly(ethylene) glycol modified
      with vitamin E (alpha tocopherol)

<400> SEQUENCE: 5

Ala Ala Pro Val
1

<210> SEQ ID NO 6
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: mod_res
<222> LOCATION: (1)..(1)
<223> OTHER INFORMATION: Modified with poly(ethylene) glycol modified
      with vitamin E (alpha tocopherol)
<220> FEATURE:
<221> NAME/KEY: Mod_Res
<222> LOCATION: (4)..(4)
<223> OTHER INFORMATION: Modified with CMK (Chloromethyl ketone)

<400> SEQUENCE: 6

Ala Ala Pro Val
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: mod_res
<222> LOCATION: (1)..(1)
<223> OTHER INFORMATION: Modified with vitamin E (alpha tocopherol)
<220> FEATURE:
<221> NAME/KEY: mod_res
<222> LOCATION: (4)..(4)
<223> OTHER INFORMATION: Modified with CMK (chloromethyl ketone)

<400> SEQUENCE: 7

Ala Ala Pro Val
1

<210> SEQ ID NO 8
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: Mod_res
<222> LOCATION: (1)..(1)
```

```
<223> OTHER INFORMATION: Modified with poly(ethylene) glycol modified
      with vitamin E (alpha tocopherol)

<400> SEQUENCE: 8

Lys Arg Cys Cys Pro Asp Thr Cys Gly Ile Lys Cys Leu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: mod_res
<222> LOCATION: (1)..(1)
<223> OTHER INFORMATION: Modified with poly(ethylene) glycol modified
      with vitamin E (alpha tocopherol)

<400> SEQUENCE: 9

Lys Arg Met Met Pro Asp Thr Met Gly Ile Lys Met Leu
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: mod_res
<222> LOCATION: (1)..(1)
<223> OTHER INFORMATION: Modified with poly(ethylene) glycol modified
      with vitamin E (alpha tocopherol)

<400> SEQUENCE: 10

Glu Glu Ile Ile Met Asp
1               5

<210> SEQ ID NO 11
<211> LENGTH: 65
<212> TYPE: PRT
<213> ORGANISM: Hirudo medicinalis

<400> SEQUENCE: 11

Met Thr Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 12
<211> LENGTH: 58
<212> TYPE: PRT
<213> ORGANISM: Bos taurus

<400> SEQUENCE: 12

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
```

```
                20                  25                  30
Phe Val Tyr Gly Gly Cys Arg Ala Lys Arg Asn Asn Phe Lys Ser Ala
                35                  40                  45
Glu Asp Cys Met Arg Thr Cys Gly Gly Ala
                50                  55
```

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: mod_res
<222> LOCATION: (1)..(1)
<223> OTHER INFORMATION: Modified with poly(ethylene) glycol modified
      with vitamin E (alpha tocopherol)
<220> FEATURE:
<221> NAME/KEY: mod_res
<222> LOCATION: (8)..(8)
<223> OTHER INFORMATION: Modified with CMK (chloromethyl ketone)

<400> SEQUENCE: 13

```
Lys Gly Ser Gly Ala Ala Pro Val
1               5
```

<210> SEQ ID NO 14
<211> LENGTH: 8
<212> TYPE: PRT
<213> ORGANISM: artificial sequence
<220> FEATURE:
<223> OTHER INFORMATION: Synthetic peptide
<220> FEATURE:
<221> NAME/KEY: mod_res
<222> LOCATION: (1)..(1)
<223> OTHER INFORMATION: Modified with poly(ethylene) glycol modified
      with vitamin E (alpha tocopherol)
<220> FEATURE:
<221> NAME/KEY: mod_res
<222> LOCATION: (1)..(1)
<223> OTHER INFORMATION: Further modified with attached FITC
      (Fmoc-K(FAM)-OH) group
<220> FEATURE:
<221> NAME/KEY: Mod_res
<222> LOCATION: (8)..(8)
<223> OTHER INFORMATION: Modified with CMK (chloromethyl ketone)

<400> SEQUENCE: 14

```
Lys Gly Ser Gly Ala Ala Pro Val
1               5
```

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is Arginine, Phenylglycine, or Norleucine
<220> FEATURE:
<221> NAME/KEY: MISC_FEATURE
<222> LOCATION: (2)..(2)
<223> OTHER INFORMATION: X is Alanine, Phenylglycine, Citrulline, or
      Norleucine
<220> FEATURE:
<221> NAME/KEY: MISC_FEATURE
<222> LOCATION: (3)..(3)
<223> OTHER INFORMATION: X is Trp, Val, or Tyr
<220> FEATURE:
<221> NAME/KEY: MISC_FEATURE

```
<222> LOCATION: (4)..(4)
<223> OTHER INFORMATION: X is Phenylglycine or Glycine

<400> SEQUENCE: 15

Xaa Xaa Xaa Xaa
1
```